United States Patent

Albright et al.

[11] Patent Number: 5,849,735
[45] Date of Patent: Dec. 15, 1998

[54] TRICYCLIC BENZAZEPINE VASOPRESSIN ANTAGONISTS

[75] Inventors: Jay D. Albright, Nanuet; Aranapakam M. Venkatesan, Elmhurst; Efren G. Delos Santos, Nanuet, all of N.Y.

[73] Assignee: American Cyanamid Company, Madison, N.J.

[21] Appl. No.: 548,805

[22] Filed: Dec. 22, 1995

Related U.S. Application Data

[63] Continuation-in-part of Ser. No. 373,169, Jan. 17, 1995, abandoned.

[51] Int. Cl.⁶ .................... A61K 31/55; A61K 31/675; C07D 243/38
[52] U.S. Cl. .................. 514/220; 514/80; 514/219; 540/542; 540/555; 540/557
[58] Field of Search .................. 514/80, 219, 220; 540/542, 555, 557

[56] References Cited

U.S. PATENT DOCUMENTS

| | | | |
|---|---|---|---|
| 4,766,108 | 8/1988 | Ali | 514/16 |
| 5,055,448 | 10/1991 | Manning et al. | 514/16 |
| 5,070,187 | 12/1991 | Gavras et al. | 530/315 |
| 5,258,510 | 11/1993 | Ogawa et al. | 540/476 |
| 5,512,563 | 4/1996 | Albright et al. | 514/217 |

FOREIGN PATENT DOCUMENTS

| | | |
|---|---|---|
| 0382185 | 2/1990 | European Pat. Off. . |
| 0470514 | 8/1991 | European Pat. Off. . |
| 0514667 | 4/1992 | European Pat. Off. . |
| 0533240 | 9/1992 | European Pat. Off. . |
| 0533242 | 9/1992 | European Pat. Off. . |
| 0533243 | 9/1992 | European Pat. Off. . |
| 0533244 | 9/1992 | European Pat. Off. . |
| 0620216 | 4/1994 | European Pat. Off. . |
| 9105549 | 5/1991 | WIPO . |
| 9404525 | 3/1994 | WIPO . |
| 9414796 | 7/1994 | WIPO . |
| 9412476 | 9/1994 | WIPO . |
| 9420473 | 9/1994 | WIPO . |

OTHER PUBLICATIONS

J. Med. Chem., 1992,35, 3905–3918, Williams et al.
J. Med. Chem., 1992, 35, 3895–3904—Manning et al.
J. Med. Chem., 1992, 35, 382–388, Manning et al.
From Vasopressin Antagonist to Agonist, DN+P 4 (4), May 1991, Ruffolo et al.
Br. J. Pharmacol. (1992), 105, 787–791, Yamamura et al.
Science, vol. 252, pp. 572–574, Yamamura et al. (1991).
J. Med. Chem., 1992, 35, 3919–3927, Evans et al.
J. Med. Chem., 1993, 36, 3993–4005, Evans et al.

Primary Examiner—Mukund J. Shah
Assistant Examiner—Brenda Coleman
Attorney, Agent, or Firm—Steven R. Eck

[57] ABSTRACT

Tricyclic compound of the general Formula I:

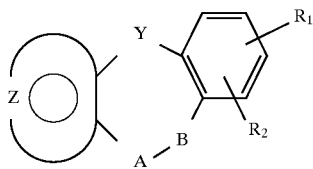

Formula I as defined herein which exhibit antagonist activity at $V_1$ and/or $V_2$ receptors and exhibit in vivo vasopressin antagonist activity, methods for using such compounds in treating diseases characterized by excess renal reabsorption of water, and process for preparing such compounds.

40 Claims, No Drawings

TRICYCLIC BENZAZEPINE VASOPRESSIN ANTAGONISTS

This application is a continuation-in-part of application Ser. No. 08/373,169 filed Jan. 17, 1995, now abandoned.

FIELD OF THE INVENTION

This invention relates to new tricyclic non-peptide vasopressin antagonists which are useful in treating conditions where decreased vasopressin levels are desired, such as in congestive heart failure, in disease conditions with excess renal water reabsorption and in conditions with increased vascular resistance and coronary vasoconstriction.

BACKGROUND OF THE INVENTION

Vasopressin is released from the posterior pituitary either in response to increased plasma osmolarity detected by brain osmoreceptors or decreased blood volume and blood pressure sensed by low-pressure volume receptors and arterial baroreceptors. The hormone exerts its action through two well defined receptor subtypes: vascular $V_1$ and renal epithelial $V_2$ receptors. Vasopressin-induced antidiuresis, mediated by renal epithelial $V_2$ receptors, helps to maintain normal plasma osmolarity, blood volume and blood pressure.

Vasopressin is involved in some cases of congestive heart failure where peripheral resistance is increased. $V_1$ antagonists may decrease systemic vascular resistance, increase cardiac output and prevent vasopressin induced coronary vasoconstriction. Thus, in conditions with vasopressin induce increases in total peripheral resistance and altered local blood flow, $V_1$-antagonists may be therapeutic agents. $V_1$ antagonists may decrease blood pressure, induced hypotensive effects and thus be therapeutically useful in treatment of some types of hypertension.

The blockage of $V_2$ receptors is useful in treating diseases characterized by excess renal reabsorption of free water. Antidiuresis is regulated by the hypothalamic release of vasopressin (antidiuretic hormone) which binds to specific receptors on renal collecting tubule cells. This binding stimulates adenylyl cyclase and promotes the cAMP-mediated incorporation of water pores into the luminal surface of these cells. $V_2$ antagonists may correct the fluid retention in congestive heart failure, liver cirrhosis, nephritic syndrome, central nervous system injuries, lung disease and hyponatremia.

Elevated vasopressin levels occur in congestive heart failure which is more common in older patients with chronic heart failure. In patients with hyponatremic congestive heart failure and elevated vasopressin levels, a $V_2$ antagonist may be beneficial in promoting free water excretion by antagonizing the action of antidiuretic hormone, On the basis of biochemical and pharmacological effects of the hormone, antagonists of vasopressin are expected to be therapeutically useful in the treatment and/or prevention of hypertension, cardiac insufficiency, coronary vasospasm, cardiac ischemia, renal vasospasm, liver cirrhosis, congestive heart failure, nephritic syndrome, brain edema, cerebral ischemia, cerebral hemorrhage-stroke, throinbosis-bleeding and abnormal states of water retention.

The following prior art references describe peptide vasopressin antagonists: M. Manning et al., *J. Med. Chem.*, 35, 382(1992); M. Manning et al., *J. Med. Chem.*, 35, 3895 (1992); H. Gavras and B. Lammek, U.S. Pat. No. 5,070,187 (1991); M. Manning and W. H. Sawyer, U.S. Pat. No. 5,055,448(1991) F. E. Ali, U.S. Pat. No. 4,766,108(1988); R. Ruffolo et al., *Drug News and Perspective*, 4(4), 217, (May)(1991). P. D. Williams et al., have reported on potent hexapeptide oxytocin antagonists [*J. Med. Chem.*, 35, 3905 (1992)] which also exhibit weak vasopressin antagonist activity in binding to $V_1$ and $V_2$ receptors. Peptide vasopressin antagonists suffer from a lack of oral activity and many of these peptides are not selective antagonists since they also exhibit partial agonist activity.

Non-peptide vasopressin antagonists have recently been disclosed, Y. Yamamura et al., *Science*, 252, 579(1991); Y. Yamamura et al., *Br. J. Pharmacol*, 105. 787(1992); Ogawa et al., (Otsuka Pharm Co., LTD.) EP 0514667-A1; EPO 382185-A2; WO9105549 and U.S. Pat. No. 5,258,510; WO 9404525 Yamanouchi Pharm.Co., Ltd., WO 9420473; WO 9412476; WO 9414796; Fujisawa Co. Ltd., EP 620216-A1 Ogawa et al, (Otsuka Pharm. Co.) EP 470514A disclose carbostyril derivatives and pharmaceutical compositions containing the same. Non-peptide oxytocin and vasopressin antagonist have been disclosed by Merck and Co.; M. G. Bock and P. D. Williams, EP 0533242A; M. G. Bock et al., EP 0533244A; J. M. Erb, D. F. Verber, P. D. Williams, EP 0533240A; K. Gilbert et al., EP 0533243A.

Premature birth can cause infant health problems and mortality and a key mediator in the mechanism of labor is the peptide hormone oxytocin. On the basis of the pharmacological action of oxytocin, antagonists of this hormone are useful in the prevention of preterm labor, B. E. Evans et al., *J. Med. Chem.* 35, 3919(1992), *J. Med. Chem.*, 36, 3993 (1993) and references therein. The compounds of this invention are antagonists of the peptide hormone oxytocin and are useful in the control of premature birth.

The present invention relates to novel tricyclic derivatives which exhibit antagonist activity at $V_1$ and/or $V_2$ receptors and exhibit in vivo vasopressin antagonist activity. The compounds also exhibit antagonist activity at oxytocin receptors.

SUMMARY OF THE INVENTION

This invention relates to new compounds selected from those of the general formula I:

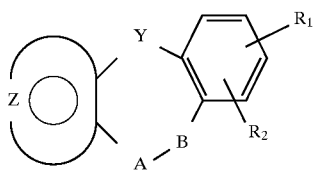

Formula I

Wherein Y is $(CH_2)_n$, O, S, NH, $NCOCH_3$, N-lower alkyl $(C_1-C_3)$, CH-lower alkyl $(C_1-C_3)$, CHNH-lower alkyl $(C_1-C_3)$, $CHNH_2$, CHN[lower alkyl $(C_1-C_3)]_2$, CHO-lower alkyl$(C_1-C_3)$, CHS-lower alkyl $(C_1-C_3)$, wherein n is an integer from 0–2: A—B is

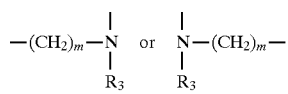

wherein m is an integer from 1–2, provided that when Y is —$(CH_2)_n$— and n=2, in may also be zero and when n is zero, in may also be three, provided also that when y is —$(CH_2)_n$ and n is 2, m may not also be two.

$R_1$ is hydrogen, halogen (chlorine, bromine, fluorine, iodine), OH, —S-lower alkyl$(C_1-C_3)$, —SH, —SO lower alkyl$(C_1-C_3)$, —$SO_2$-lower alkyl$(C_1-C_3)$, —CO-lower alkyl$(C_1-C_3)$, —$CF_3$; lower alkyl ($C_1$–$C_3$); O-lower alkyl($C_1$–$C_3$), —$NO_2$, —$NH_2$, —NHCO lower alkyl ($C_1$–$C_3$), —N-[lower alkyl ($C_1$–$C_3$)]$_2$, —$SO_2NH_2$; —$SO_2NH$ lower alkyl($C_1$–$C_3$) or —$SO_2N$[lower alkyl($C_1$–$C_3$)]$_2$;

$R_2$ is hydrogen, Cl, Br, F, I. —OH, lower alkyl($C_1$–$C_3$), O-lower alkyl($C_1$–$C_3$), or $R_1$ and $R_2$ taken together are methylenedioxy or ethylenedioxy;

$R_3$ is the moiety:

wherein Ar is a moiety selected from the moiety

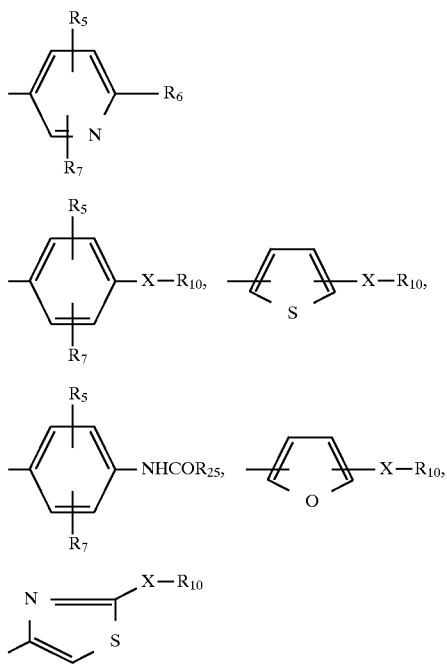

$R_4$ is hydrogen, lower alkyl($C_1$–$C_3$); —CO-lower alkyl ($C_1$–$C_3$);

$R_5$ and $R_7$ are selected from hydrogen, ($C_1$–$C_3$) lower alkyl, ($C_1$–$C_3$) lower alkoxy and halogen;

$R_6$ is selected from (a) moieties of the formula:

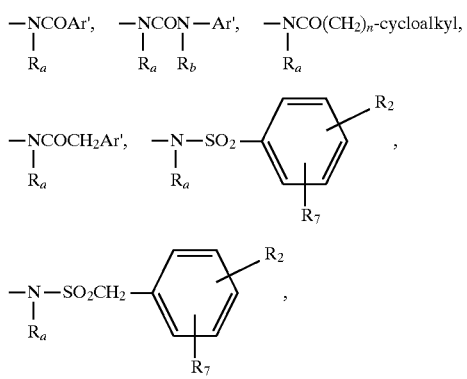

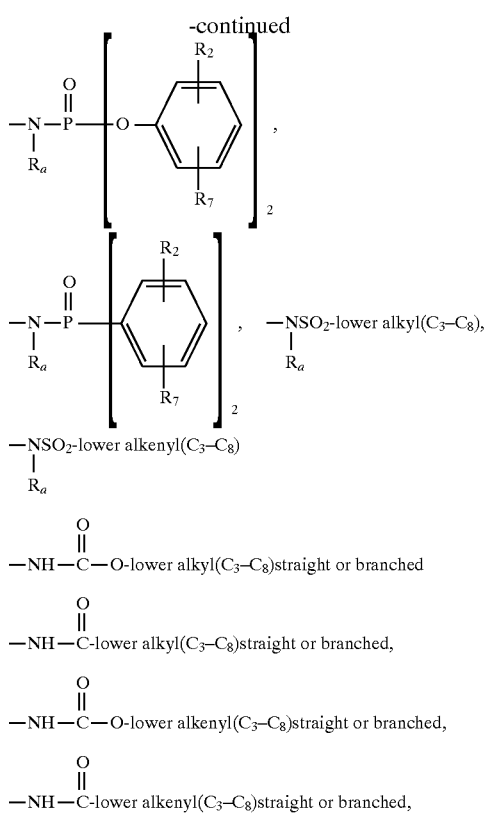

wherein cycloalkyl is defined as $C_3$ to $C_6$ cycloalkyl, cyclohexenyl or cyclopentenyl; $R_a$ is hydrogen, $CH_3$, $C_2H_5$, moieties of the formulae:

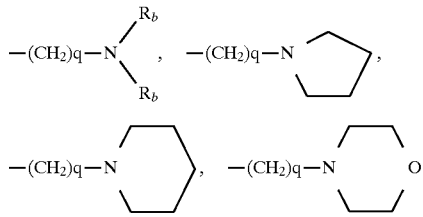

—$(CH_2)_2$O-lower alkyl($C_1$–$C_3$) or —$CH_2CH_2OH$; q is one, two or three; $R_b$ is hydrogen, $CH_3$ or —$C_2H_5$;

(b) a moiety of the formula:

—X—$R_{10}$; wherein $R_{10}$ is lower alkyl($C_3$–$C_8$), lower alkenyl ($C_3$–$C_8$), –$(CH_2)_p$-cycloalkyl ($C_3$–$C_6$),

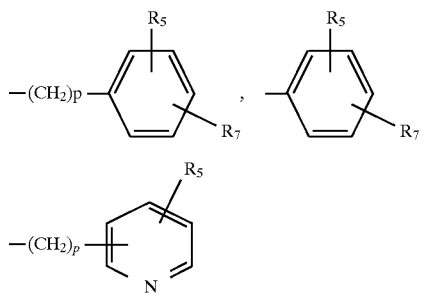

-continued

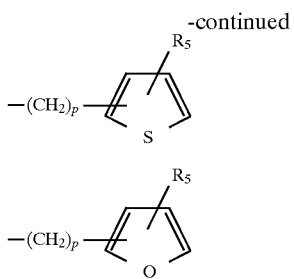

and p is zero to three:

X is O, S, NH, NCH$_3$,

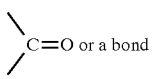 or a bond and R$_5$ and R$_7$ are as previously defined (c) a moiety of the formula:

wherein J is R$_a$, lower alkyl(C$_3$—C$_8$) branched or unbranched, lower alkenyl(C$_3$—C$_8$) branched or unbranched, O-lower alkyl(C$_3$—C$_8$) branched or unbranched, —O-lower alkenyl(C$_3$—C$_8$) branched or unbranched, tetrahydrofuran, tetrahydrothiophene, the moieties

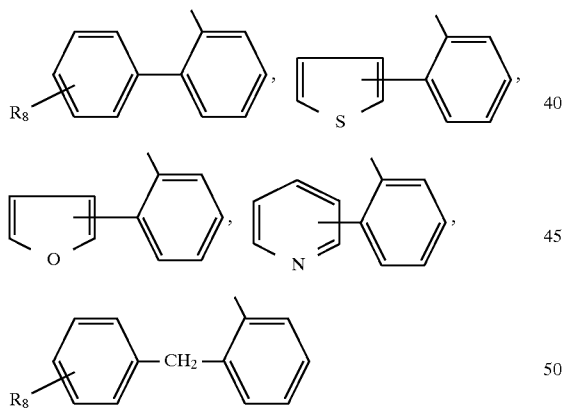

or —CH$_2$—K' wherein K' is halogen, —OH, tetrahydrofuran, tetrahydrothiophene or the heterocyclic ring moiety:

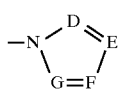

wherein D, E, F and G are selected from carbon or nitrogen and wherein the carbon atoms may be optionally substituted with halogen, (C$_1$-C$_3$)lower alkoxy, —CO-lower alkyl (C$_1$-C$_3$), CHO, (C$_1$-C$_3$)lower alkoxy, —CO$_2$-lower alkyl (C$_1$-C$_3$), and R$_a$ and R$_b$ are as hereinbefore defined;

(d) a moiety selected from those of the formulae:

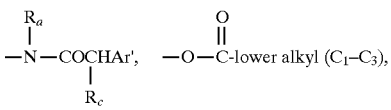

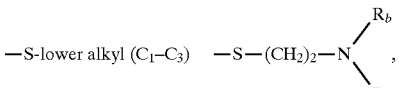

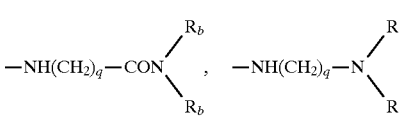

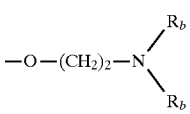

wherein R$_c$ is selected from halogen, (C$_1$-C$_3$)lower alkyl, —O-lower alkyl(C$_1$-C$_3$) and OH, R$_b$ is as hereinbefore defined;

Ar' is a moiety selected from the group

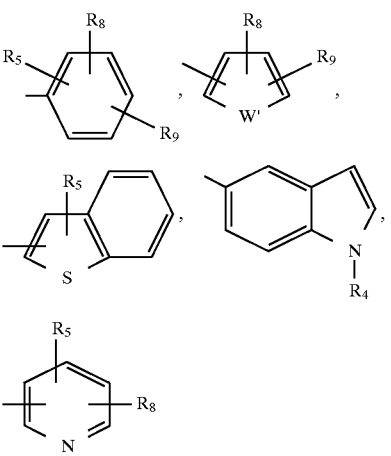

R$_8$ and R$_9$ are independently hydrogen, lower alkyl (C$_1$-C$_3$); O-lower alkyl(C$_1$-C$_3$); S-lower alkyl(C$_1$-C$_3$), —CF$_3$, —CN, —OH, —SCF$_3$, —OCF$_3$, halogen, NO$_2$, amino or NH lower alkyl(C$_1$-C$_3$), —N-[lower alkyl (C$_1$-C$_3$)]$_2$, —N(R$_b$)(CH$_2$)$_q$—N(R$_b$)$_2$;

W' is O, S NH, N-lower alkyl(C$_1$-C$_3$), NCO-lower alkyl (C$_1$-C$_3$) or NSO$_2$-lower alkyl(C$_1$-C$_3$) or NSO$_2$lower alkyl(C$_1$-C$_3$);

R$_{25}$ is selected from the moieties

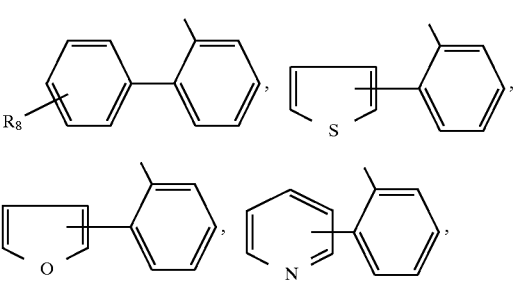

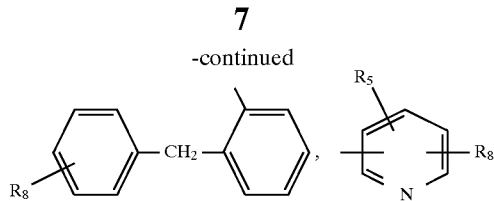

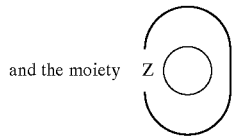

represents: (1) phenyl or substituted phenyl optionally substituted by one or two substituents selected from $(C_1-C_3)$ lower alkyl, halogen, amino, $(C_1-C_3)$ lower alkoxy, or $(C_1-C_3)$ lower alkyl amino; (2) a 5-membered aromatic (unsaturated) heterocyclic ring having one heteroatom selected from O, N or S; (3) a 6-membered aromatic (unsaturated) heterocyclic ring having one nitrogen atom; (4) a 5 or 6-membered aromatic (unsaturated) heterocyclic ring having two nitrogen atoms; (5) a 5-membered aromatic (unsaturated) heterocyclic ring having one nitrogen atom together with either one oxygen or one sulfur atom; wherein the 5 or 6-membered heterocyclic rings are optionally substituted by $(C_1-C_3)$ lower alkyl, formyl, a moiety of the formula:

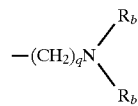

halogen or $(C_1-C_3)$ lower alkoxy. For example, the fused heterocyclic ring may be represented by furan, pyrrole, pyrazole, thiophene, thiazole, oxazole, imidazole, pyrimidine or pyridine ring which may be substituted or unsubstituted.

DETAILED DESCRIPTION OF THE INVENTION

Within the group of the compounds defined by Formula I, certain subgroups of compounds are broadly preferred. Broadly preferred are those compounds wherein $R_3$ is a moiety:

and Ar is selected from the moiety:

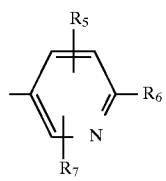

wherein $R_5$, $R_6$ and $R_7$ are as hereinbefore defined.

Especially preferred are compounds wherein $R_3$ is the moiety:

and Ar is selected from the moiety:

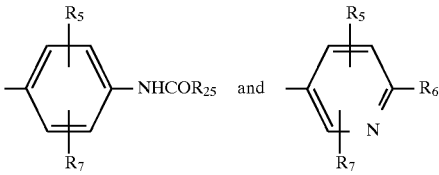

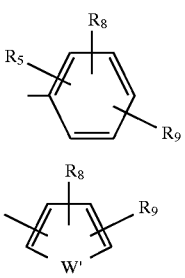

wherein $R_8$, $R_9$, $R_{25}$ and W' are as hereinbefore defined.

Also especially broadly preferred are compounds wherein Y in Formula I is $-(CH_2)_n-$ and n is zero or one; A—B is

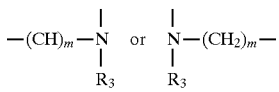

and $R_4$, $R_5$, $R_6$, $R_7$, $R_8$, $R_9$ and $R_{10}$ are as hereinbefore defined; and m is an integer from 1–2.

The most broadly preferred of the compounds of Formula I are those wherein Y is $-(CH_2)_n-$ and n is one; A—B is

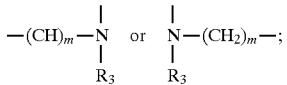

m is one or two $R_3$ is the moiety:

Ar is

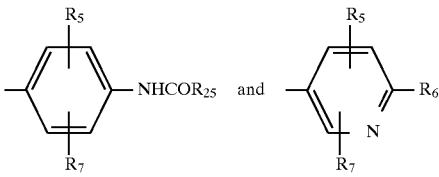

$R_6$ is

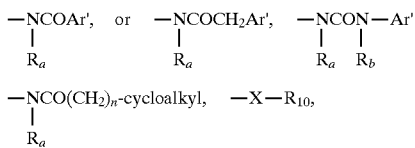

and Ar' is a moiety:

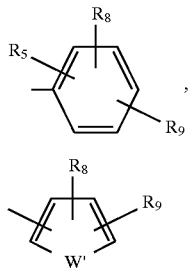

Cycloalkyl $R_a$, $R_b$ and W' are as previously defined and $R_8$ and $R_9$ are preferably ortho $CF_3$, Cl, $OCH_3$, $CH_3$, $SCH_3$ or $OCF_3$ substituents or Ar' is a disubstituted derivative wherein $R_8$ and $R_9$ are independently Cl, $OCH_3$, $CH_3$ and F.

The most highly broadly preferred of the compounds of Formula I are those wherein Y is —$(CH_2)_n$—, n is zero or one and the moiety

represents a phenyl, substituted phenyl, thiophene, furan, pyrrole or a pyridine ring; A—B is

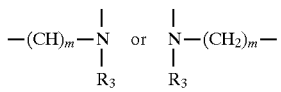

m is one when n is one and m is two when n is zero; $R_3$ is the moiety:

wherein Ar is

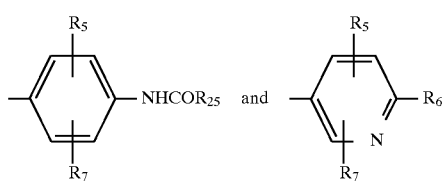

and $R_6$ is selected from the group

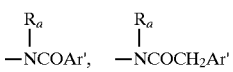

where Ar' is selected from the moieties:

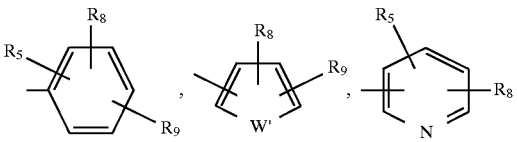

and $R_a$, $R_b$, $R_1$, $R_2$, $R_4$, $R_5$, $R_6$, $R_7$, $R_8$, $R_9$, $R_{25}$ and W' are as previously defined.

Most particularly preferred are compounds of the formulae:

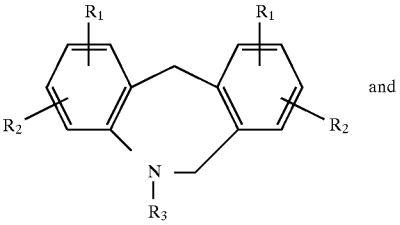

and

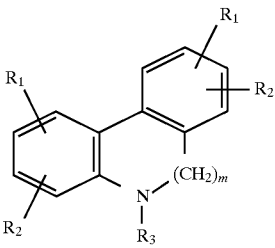

wherein m is an integer one or two; $R_1$ and $R_2$ are as previously defined;

$R_3$ is the moiety:

wherein Ar is selected from moieties of the formulae:

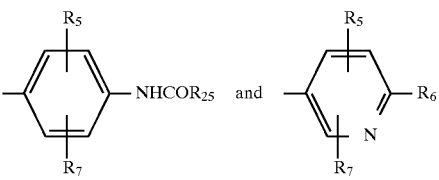

$R_6$ is

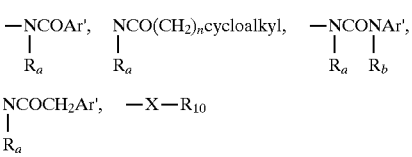

wherein cycloalkyl is defined as $C_3$–$C_6$ cycloalkyl, cyclohexenyl or cyclopentenyl and wherein Ar' is selected from the moieties:

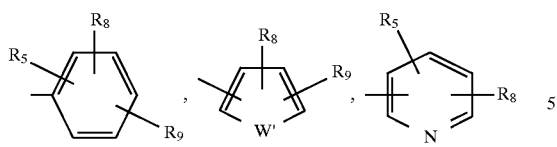

$R_a$ is independently selected from hydrogen, $CH_3$ or $—C_2H_5$; and $R_5$, $R_7$, $R_8$, $R_9$, $R_{10}$, $R_{25}$, X and W' are as hereinbefore defined.

Also particularly preferred are compounds of the formulae:

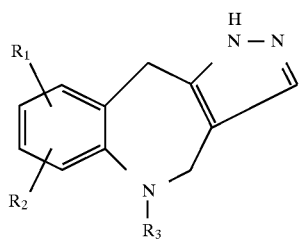

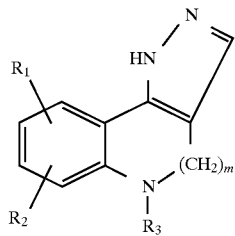

wherein m is an integer one or two; $R_1$ and $R_2$ are as previously defined;

$R_3$ is the moiety:

—CAr wherein Ar is selected from moieties of the formulae:

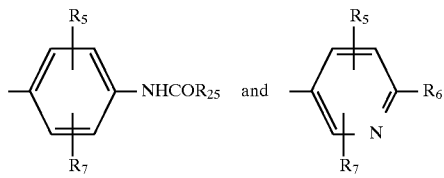

$R_6$ is

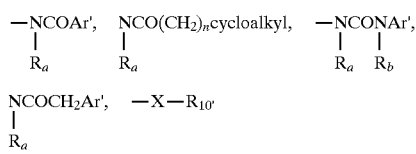

-continued

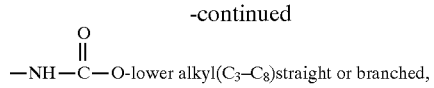
—NH—C—O-lower alkyl($C_3$–$C_8$)straight or branched,

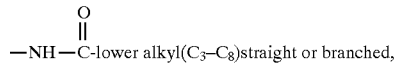
—NH—C-lower alkyl($C_3$–$C_8$)straight or branched,

—NH—C—O-lower alkenyl($C_3$–$C_8$)straight or branched,

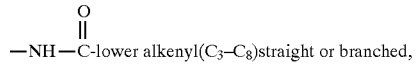
—NH—C-lower alkenyl($C_3$–$C_8$)straight or branched, wherein cycloalkyl is defined as $C_3$ to $C_6$ cycloalkyl, cyclohexenyl or cyclopentenyl and wherein Ar' is selected from the moieties:

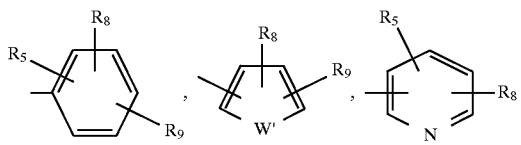

Ra is independently selected from hydrogen, $CH_3$ or $—C_2H_5$; and $R_5$, $R_7$, $R_8$, $R_9$, $R_{10}$, $R_{25}$, X and W' are as hereinbefore defined.

Compounds of this invention may be prepared as shown in Scheme I by reaction of tricyclic derivatives of Formula 3a and 3b with a substituted or unsubstituted 6-nitropyridine-3-carbonyl chloride 4 to give the intermediates 5a and 5b. Reduction of the nitro group in intermediates 5a and 5b gives the 6-amino-3-pyridinylcarbonyl derivatives 6a and 6b. The reduction of the nitro group in intermediates 5a and 5b may be carried out under catalytic reduction conditions (hydrogen-Pd/C; Pd/C-hydrazine-ethanol) or under chemical reduction conditions (SnCl2-ethanol; Zn-acetic acid; $TiCl_3$) and related reduction conditions known in the art for converting a nitro group to an amino group. The conditions for conversion of the nitro group to the amino group are chosen on the basis of compatibility with the preservation of other functional groups in the molecule. Reaction of compounds of Formula 6a and 6b with aroyl chlorides, heteroaroyl chlorides, arylsulfonyl chlorides, diarylphlosphinyl chlorides, diphenoxyphosphinyl chlorides, alkyl ($C_3$–$C_8$) carbonyl chlorides, alkenyl ($C_3$–$C_8$)carbonyl chlorides, alkoxy($C_3$–$C_8$)carbonyl chlorides, alkenyloxy($C_3$–$C_8$)carbonyl chlorides, alkyl ($C_3$–$C_8$)sulfonyl chlorides, alkenyl($C_3$–$C_8$)sulfonyl chlorides cycloalkylcarbonyl chlorides, arylcarbamoyl chlorides or heteroarylcarbamoyl chlorides as illustrated in Scheme 1, gives the novel compounds 8a and 8b of this invention. The reactions may be carried out in solvents such as chloroform, dichloromethane, dioxane, tetrahydrofuran, toluene and the like in the presence of a tertiary base such as triethylamine, diisopropylethylamine or pyridine at 0° C. to 50° C. If more than one aroyl, heteroaroyl or arylsulfonyl group, etc. is introduced during the reaction, mild base treatment (NaOH, KOH etc.) in a lower alkanol removes the second such group to give the products 8a and 8b.

Scheme 1
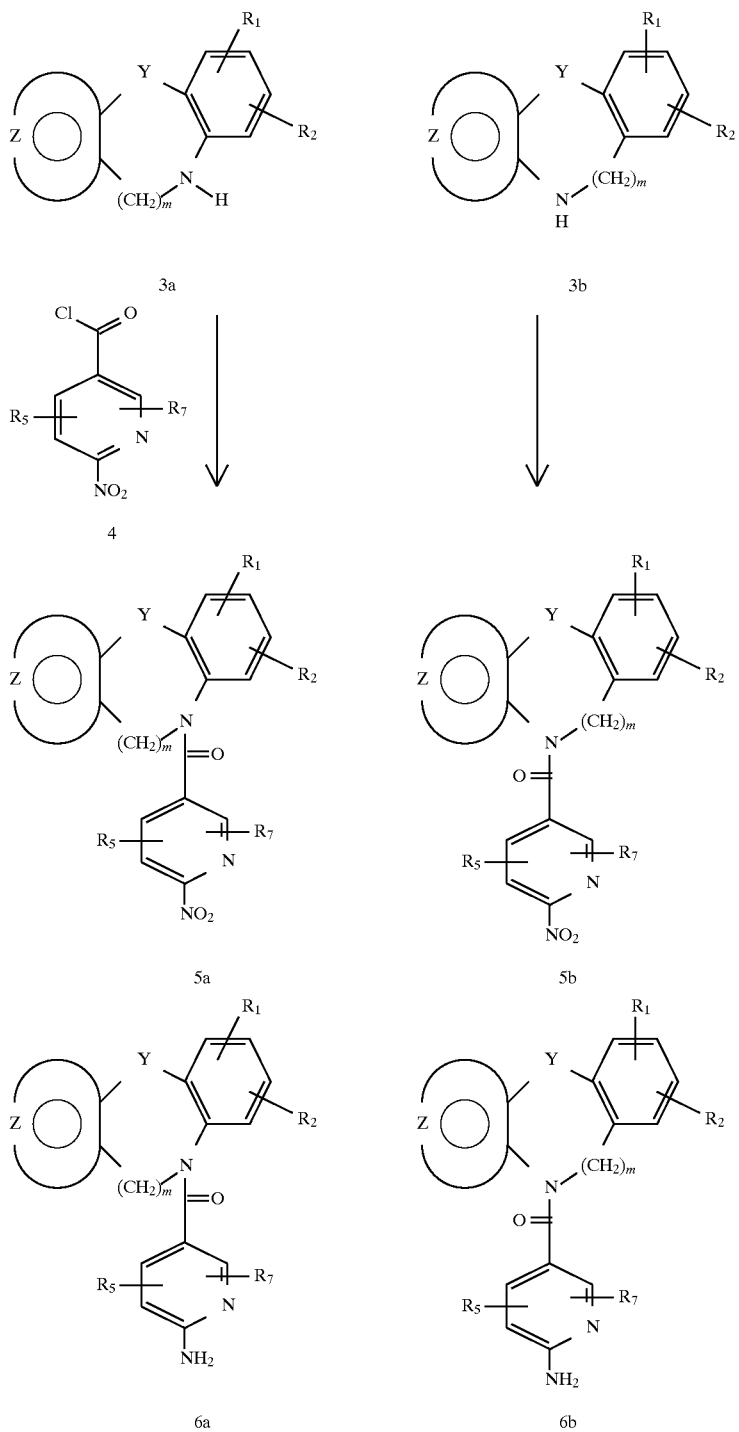

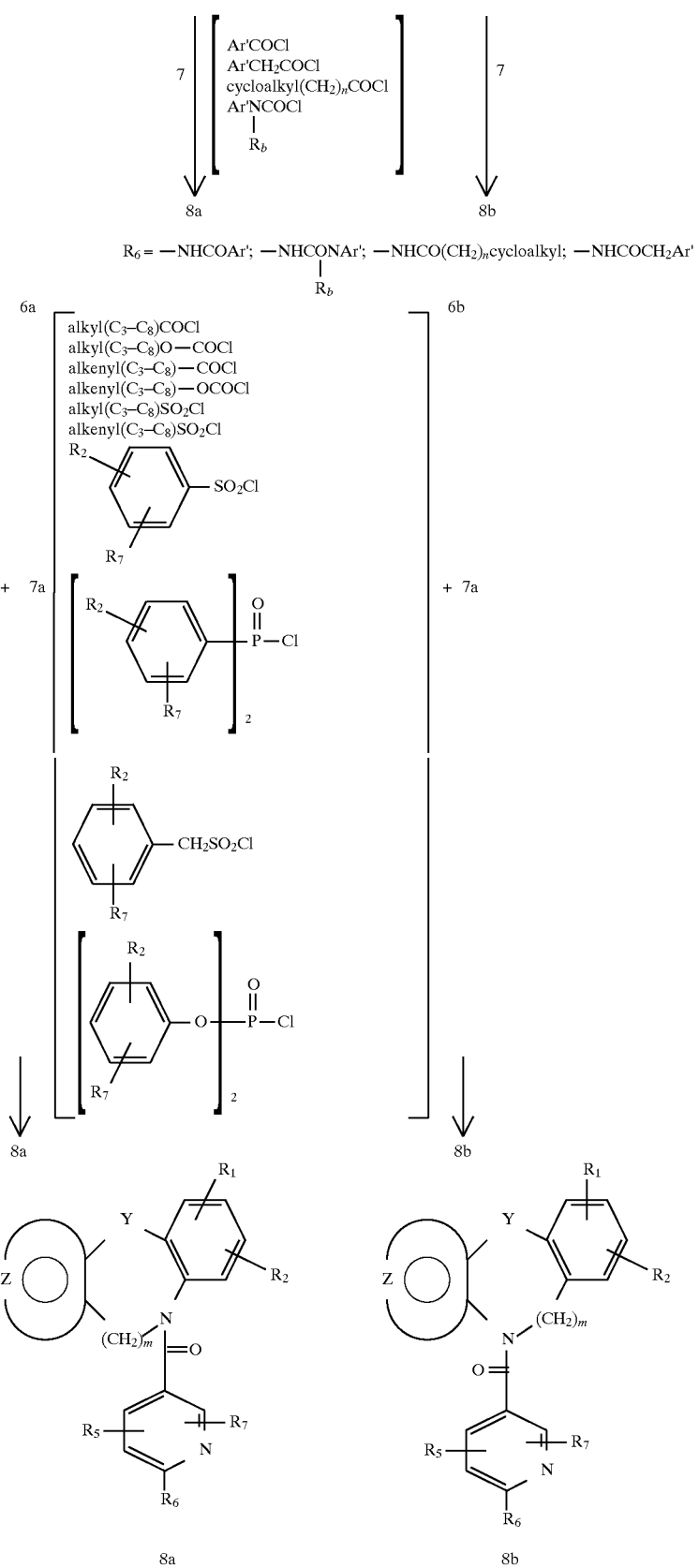

-continued
Scheme 1

$R_6 =$ —NHCOalkenyl($C_3$–$C_8$), —NHCOalkyl($C_3$–$C_8$), —NHCO$_2$alkyl($C_3$–$C_8$), —NHSO$_2$alkyl($C_3$–$C_8$), —NHCO$_2$alkenyl($C_3$–$C_8$) —NHSO$_2$alkenyl($C_3$–$C_8$)

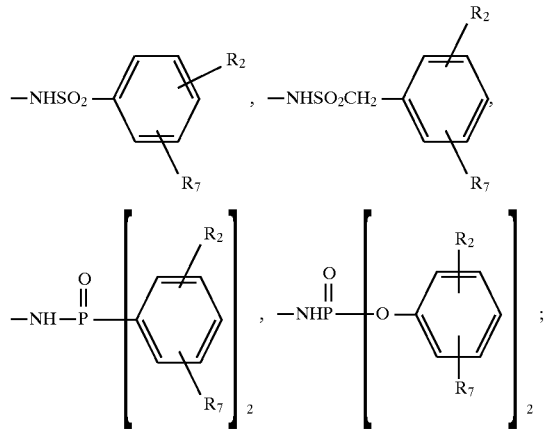

Reaction of tricyclic derivatives of Formula 6a and 6b with either a carbamoyl derivative 9 or a isocyanate derivative 10 gives compounds (Scheme 2) of Formula 11a and 11b which are vasopressin antagonists and/or oxytocin antagonists of Formula I wherein $R_6$ is

and $R_b$ is H, $CH_3$ or $C_2H_5$.

Scheme 2

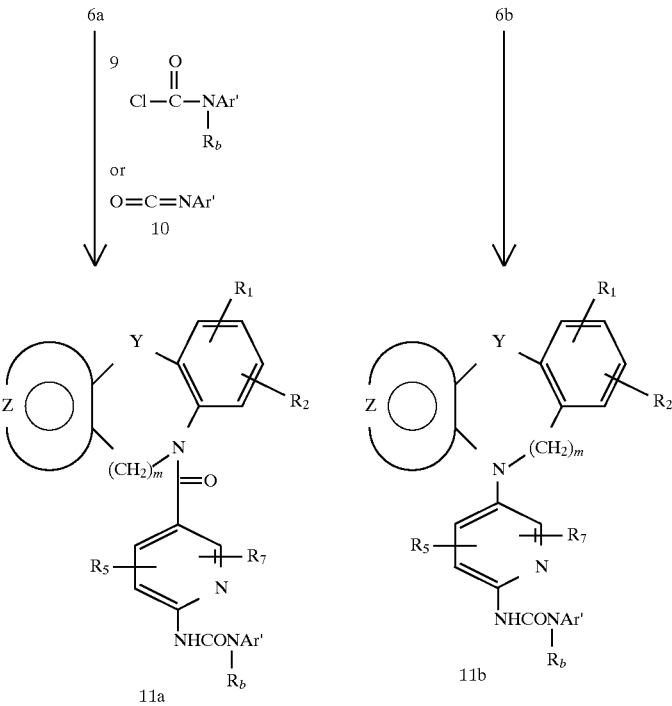

Reaction of tricyclic derivatives of Formula 3a and 3b with a 6-chloro or a 6-fluoropyridinine-3-carbonyl chloride 12 gives intermediates 13a and 13b (Scheme 3).
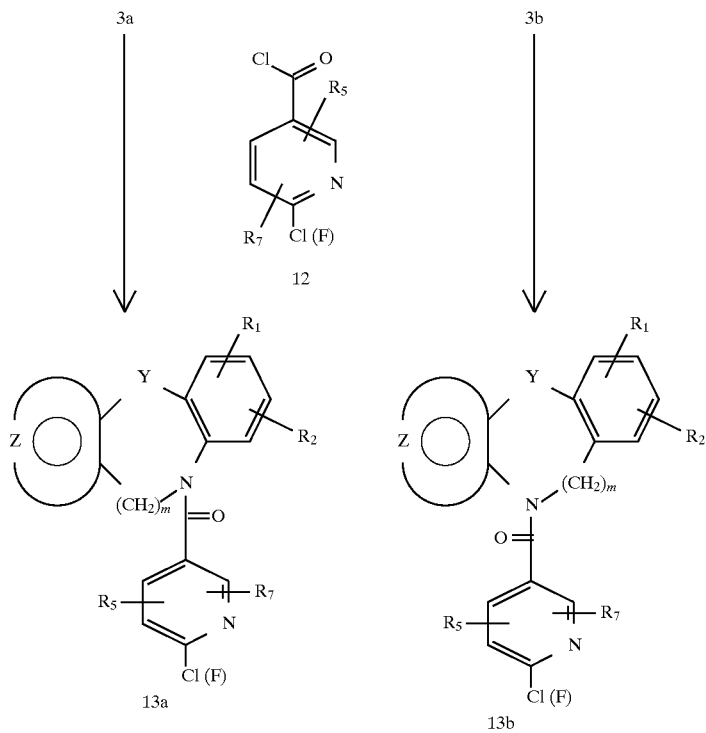
The intermediates 13a and 13b may be reacted with $R_{10}X^-$ (14) wherein $R_{10}$ is as previously defined and X is O, S, NH or $NCH_3$ to give derivatives of 15a and 15b as shown in Scheme 4.
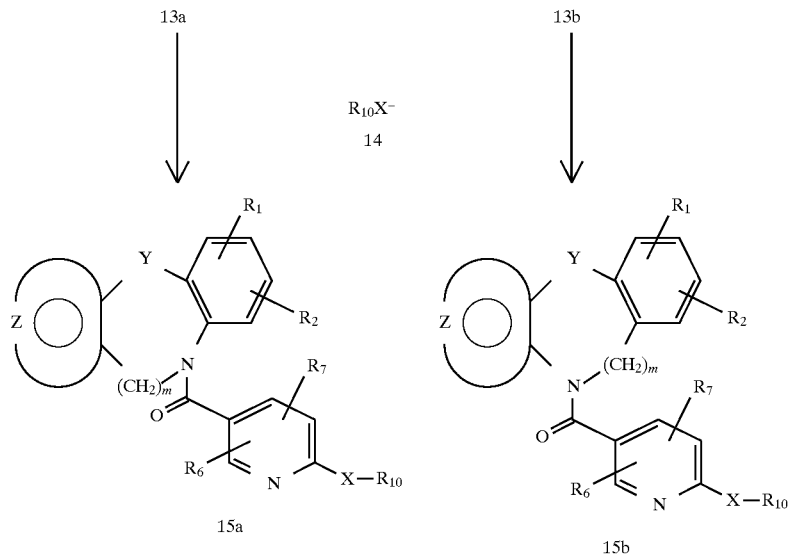

The compounds of Formula I wherein Y, A—B, Z, $R_1$, $R_2$ and $R_3$ are as defined and the $R_3$ (—COAr) aryl group is

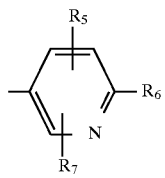

wherein $R_6$ is as previously defined may be prepared as shown in Scheme 5 by first synthesizing the pyridinyl moieties 16 which are to be attached to the tricyclic benzazepine units.

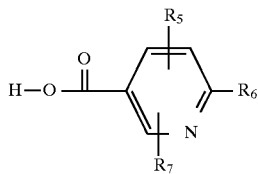

16

The preformed pyridinyl moieties 16 may be activated for coupling by reaction with peptide coupling reagents or preferably activated by conversion to the pyridine-3-carbonyl chlorides 17. The coupling may be carried out in inert solvents such as chloroform, dichloromethane, tetrahydrofuran, dioxane, toluene and the like in the presence of a tertiary amine such as trimethylamine. The reactions may also be carried out in pyridine and related alkyl pyridines.

dihydro-5H-dibenz[b,e]azepines and substituted derivatives are prepared according to literature procedures: L. H. Werner, et al., *J. Med. Chem.*,8,74–80 (1965); A. W. H. Wardrop et al., *J. Chem. Soc.* Perkins Trans I, 1279–1285 (1976).

Substituted 5,11-dihydrodibenz[b,e]azepin-6-one are prepared by literature procedures: J. Schmutz et al., *Helv. Chim. Acta.*, 48, 336 (1965); and reduced to substituted 6,11-dihydro-5H-dibenz[b,e]azepines with lithium aluminum hydride, borane, borane-dimethylsulfide and agents know to reduce an amide carbonyl to a methylene group. Intermediate 10,11-dihydrodibenz[b,f][1,4]thiazepines are prepared by literature procedures—for example, see K. Brewster et al., *J. Chem. Soc.* Perkin I, 1286 (1976). Reduction of either dibenz[b,f][1,4]oxazepines [A. W. H. Wardrop et al., *J. Chem. Soc.* Perkin Trans. I, 1279 (1976)] and dibenz[b,f] [1,4]oxazepin-11(10H)-ones and dibenz[b,f][1,4]thiazepin-11(10H)-ones—J. Schmutz et al., *Helv. Chim. Acta.,* 48, 336 (1965); may be carried out with lithium aluminum hydride in inert solvents such as dioxane and the like. The tricyclic 6,7-dihydro-5H-dibenz[b,d]azepine intermediates of Formula 30 may be prepared by the literature procedures: T. Ohta et al., *Tetrahedron Lett.,* 26, 5811 (1985); Wiesner et al., *J. Amer. Chem. Soc.,* 77, 675 (1955); or derivatives may be prepared by coupling procedures illustrated in Scheme 7. The reduction of nitro compounds of structure type 31 followed by ring closure, affords lactams 32 which are reduced to give tricyclic azepines of Formula 33.

5,11-Dihydro-6H-pyrido[3,2-c][1]benzazepines are prepared by literature procedures—J. Firl et al., *Liebigs Ann. Chem.* 469, (1989). 11H-Pyrido[2,3-b][1,4]benzodiazepin-6(5H) ones have been reported by J. F. F. Liegeois et al.,*J.*

Scheme 5

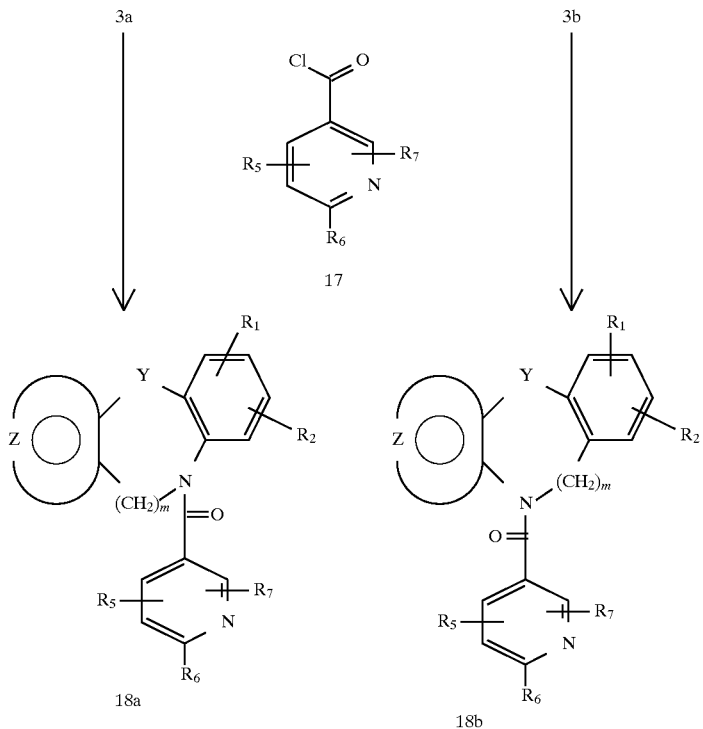

The starting materials 3a and 3b in Scheme 1 can be made by literature methods. For example, intermediate 6,11-

*Med. Chem* 36, 2107 (1993) and these derivatives are reduced to 11H-pyrido[[2,3-b][1,4]benzodiazepines. The synthesis of tricyclic 1,4,5,10-tetrahydropyrazolo-[4,3-c][1]benzodiazepine and the 3-chloro derivative have been reported—G. Palazzino, et al., *J. Heterocyclic Chem.*, 26, 71 (1989). 4,10-Dihydro-5H-thieno[3,2-c][1]benzazepine 21a and 9,10-dihydro-4H-thieno[2,3-c][1]benzazepine 21b may be prepared by coupling tributyltin derivatives 19 and 20 with 2-nitrobenzyl bromide in the presence of tetrakis(triphenylphosphine) palladium(O) as shown in Scheme 6.

Following coupling of intermediate 24 to give the tricyclic azepine 25, the nitro group is reduced to give the 6-aminonicotinoyl derivative 26. The derivative 26 is then reacted with the appropriate acid chlorides as illustrated in Scheme 7 to give the products 27 and 27a.

Also depicted in Scheme 7 is the synthesis of intermediate tricyclic azepine 30 and 33. The tricyclic lactam derivatives 29 and 32 may be prepared by reduction of nitro intermediates 28 and 31, followed by ring closure of the corresponding amino derivatives. These tricyclic lactam intermediates 29 and 32 may be reduced with lithium aluminum hydride (LAH) or borane to give the tricyclic azepines 30 and 33.

Scheme 6

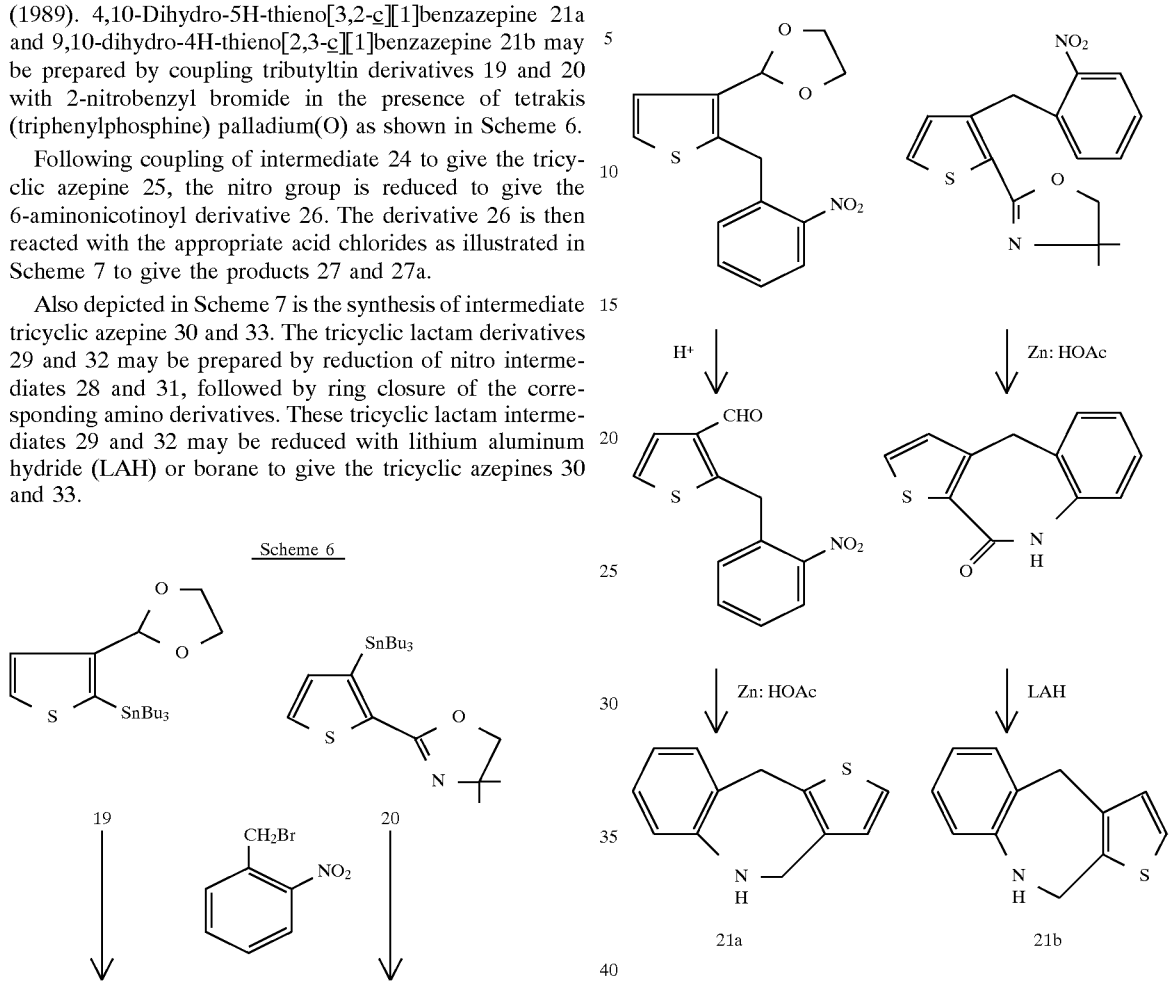

Scheme 7

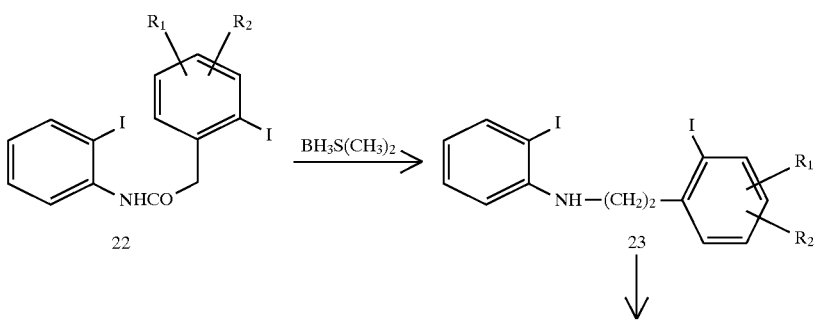

-continued
Scheme 7
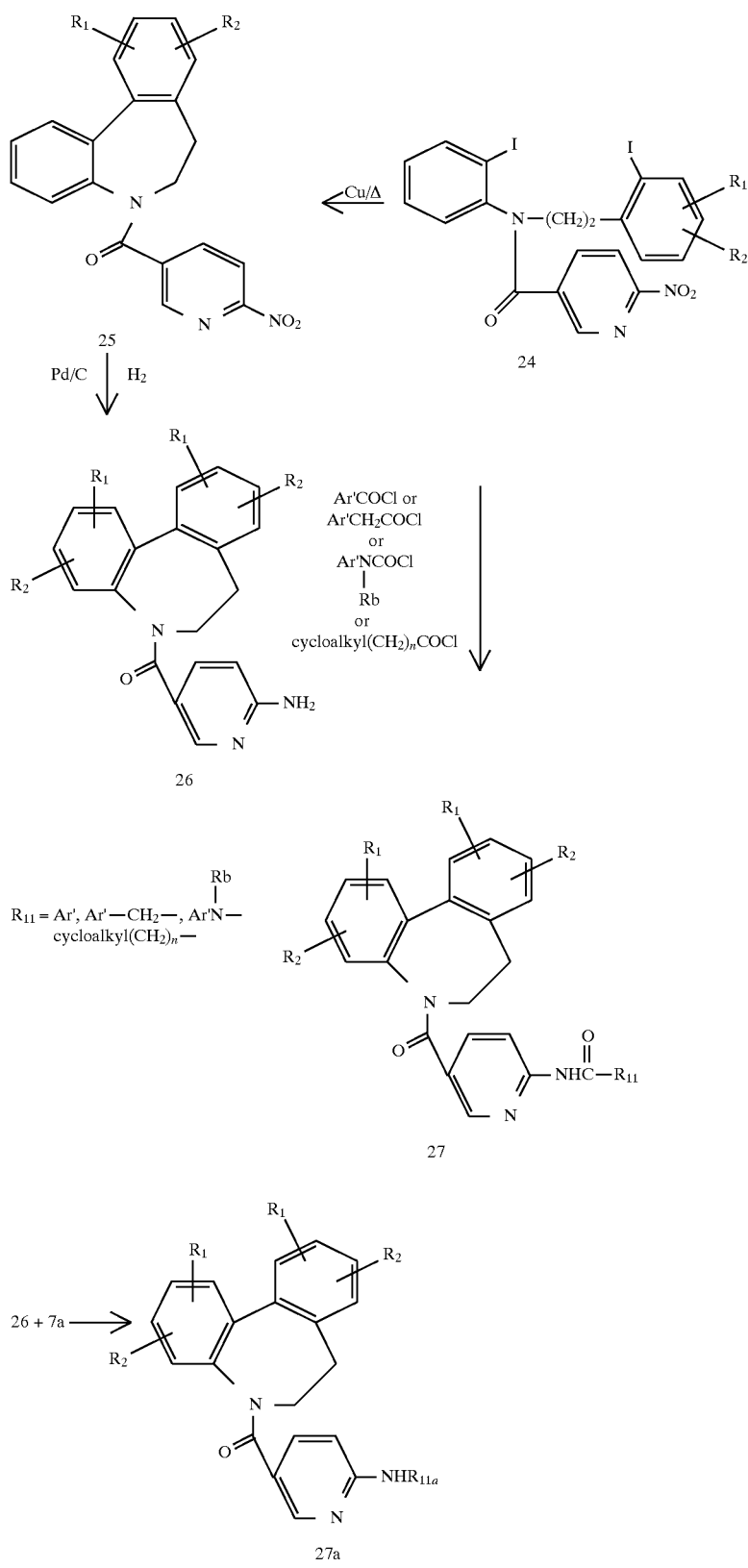

-continued
Scheme 7
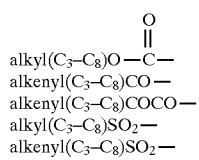
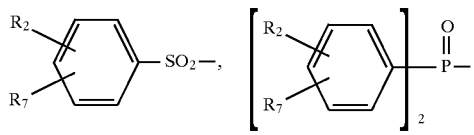
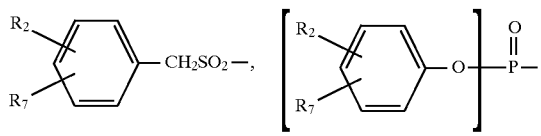
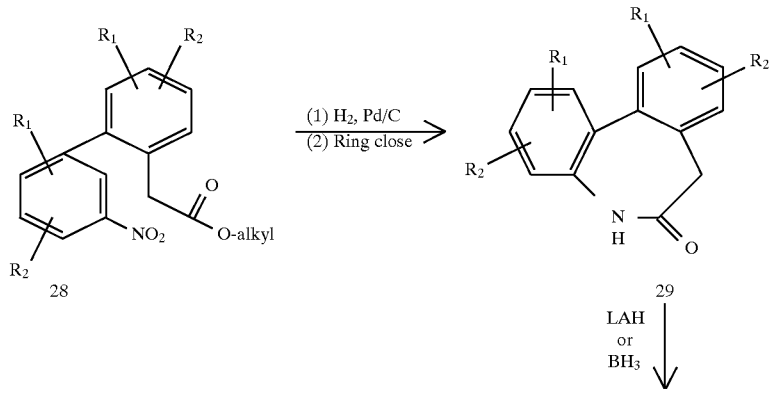
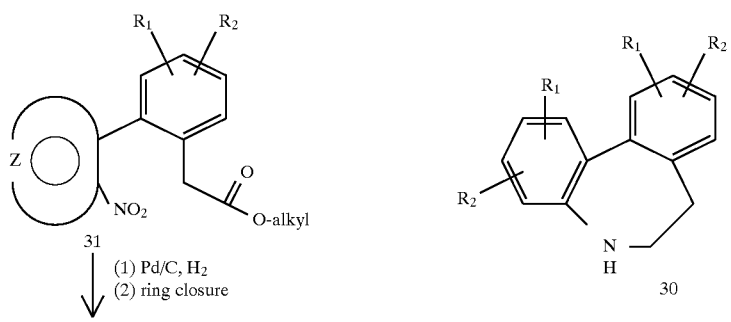
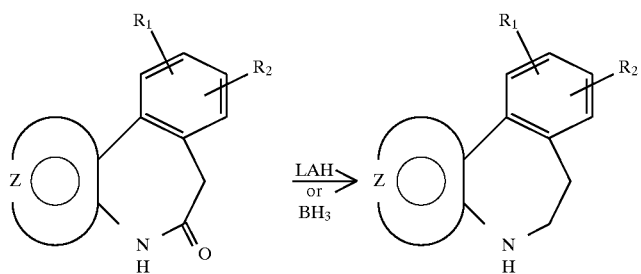

-continued
Scheme 7

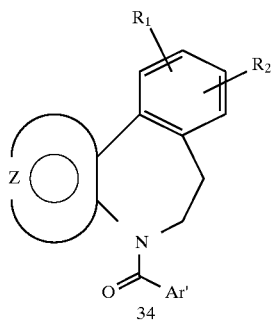

Tricyclic intermediates 42 for the synthesis of selected vasopressin antagonists of this invention wherein Y in Formula I is —$CH_2$— and m is one, may be prepared as shown in Scheme 8. Suitable 1-nitro-2-chloro or 1-nitro-2-bromo heterocycles 35 undergo halogen exchange when reacted with a alkyllithium reagent such as t-butyllithium, s-butyllithium or n-butyllithium to give intermediates 37 which react with anhydrides of Formula 38. $R_{12}$ is tert-butyl, secondary butyl, n-butyl, 2,6-dimethylpiperidine or a hindered non-nucleophilic dialkylamine. The nitro products 39 are reduced with hydrogen and a suitable catalyst or chemically reduced (Zn-acetic acid, $TiCl_3$ etc.) to the amino intermediates 40. Ring closure to the cyclic lactams 41 is conveniently carried out by heating in xylene or an inert solvent at 100° C. to 200° C. The cyclic lactams of structure type 41 are readily reduced by borane in tetrahydrofuran, borane-dimethylsulfide in tetrahydrofuran or lithium aluminum hydride in a suitable solvent such as dioxane to give the tricyclic compounds 42.

Alternatively phenyllithium derivatives 37b, which are prepared by lithiation of protected benzaldehyde derivatives or by lithiation of 2-chloro or 2-bromo protected benzaldehyde derivatives, are reacted with derivatives 38b wherein Z is as previously defined. Derivatives 38b are prepared by standard procedures such as ring closure of 1-amino-2-carboxy heteroaromatic compounds or 1-amino-2-benzoic acid derivatives, with acetic anhydride (Scheme 8).

Scheme 8

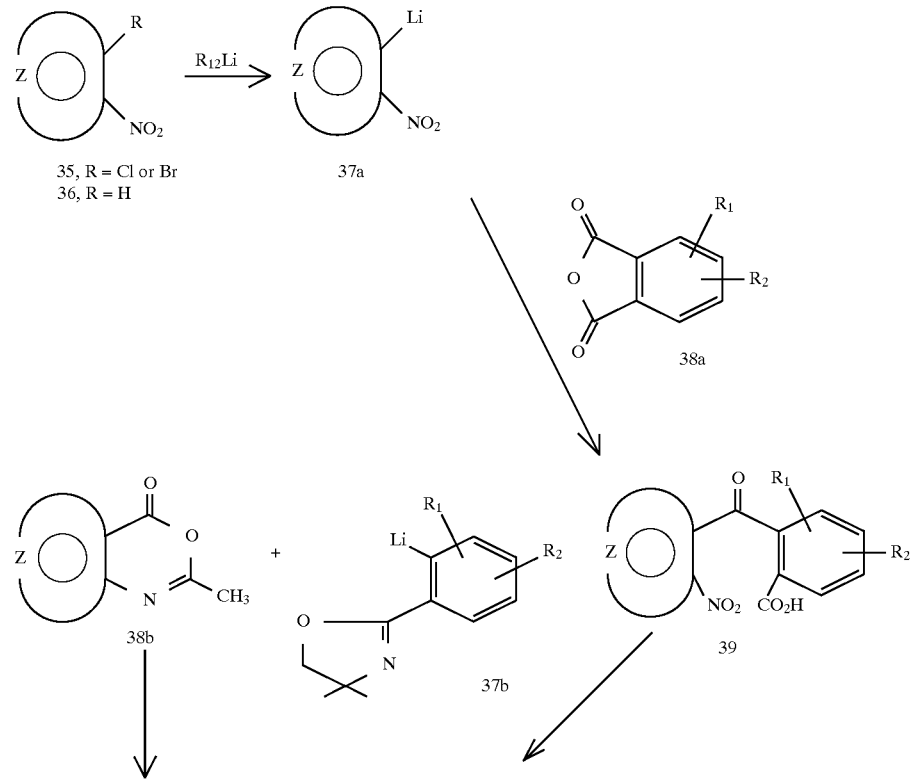

-continued
Scheme 8

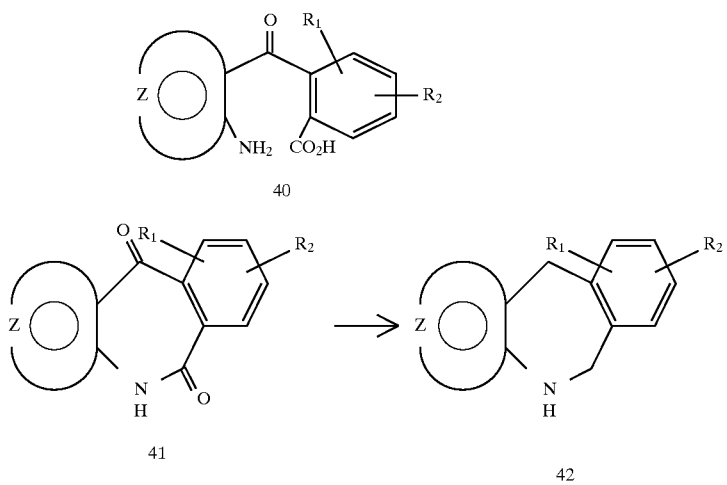

Alternatively, as shown in Scheme 9, some of the tricyclic derivatives of structural type 42 may be prepared by "palladium" type coupling or "copper" induced coupling of halogenated derivatives 43 to give tricylic lactams 44. Reduction of the lactam carbonyl group gives the intermediates 42. Coupling of halogen derivatives 45 to effect ring closure with activated copper or "palladium" type reagents which induce aryl coupling gives lactams 46. Borane reduction of lactams 46 gives derivatives 47. Ullmann cross couplings of halogenated hetterocycles and 2-bromonitrobenzenes and related cross couplings by low valent palladium species such as [Pd(PPh$_3$)$_4$] and PdCl$_2$(PPh$_3$)$_2$ are known synthetic procedures; N. Shimizu et al., *Tetrahedron Lett.* 34, 3421 (1993) and references therein; N. M. Ali et al., *Tetrahedron*, 37, 8117 (1992) and references therein; J. Stavenuiter et al., Heterocycles, 26 2711 (1987) and references therein.

Scheme 9

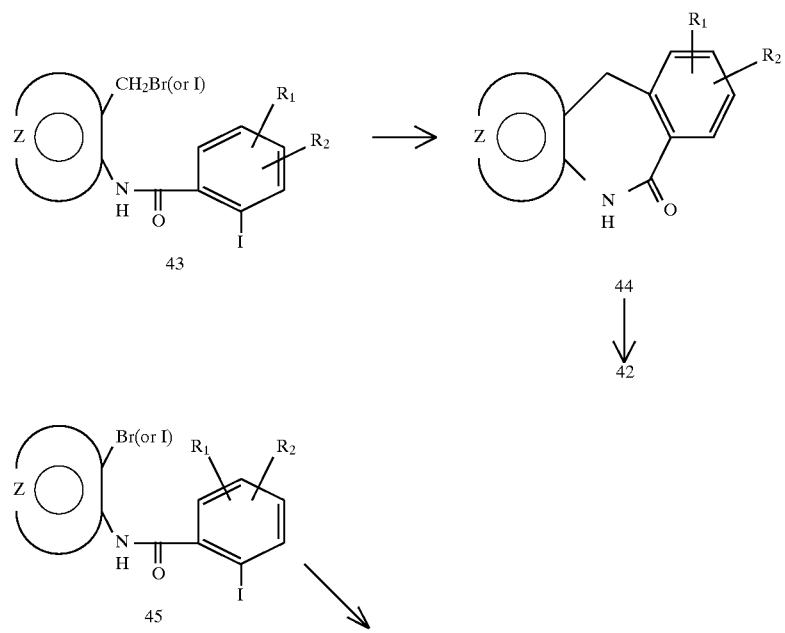

-continued
Scheme 9

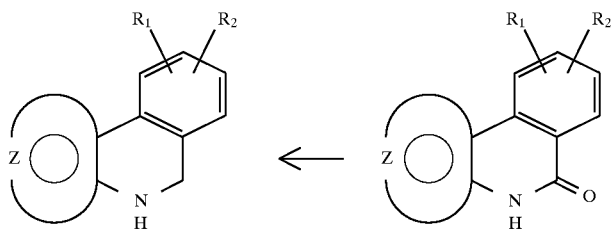

Tetrahydro-1H-1-benzazepin-5-ones 51 and the tetrahydro-1H-1-benzazepin-2,5-diones 52 are useful compounds for the synthesis of intermediate tricyclic heterocyclic structures 53 and 54 (Scheme 10). The tetrahydrobenzazepin-5-ones 51 and 52 may be formulated to give hydroxymethylene derivatives or reacted with either the Vilsmeier reagent or the N,N-dimethylformamide dimethyl acetal to give the dimethylaminomethylene derivatives. The construction of heterocyclic rings from α-hydroxymethyleneketones by reactions with hydrazine, N-methylhydrazine, hydroxylamine or formamidine to give pyrazoles, N-methylpyrazoles, oxazoles or pyrimidines respectively, is a standard literature procedure. See Vilsmeier formylation—*Tetrahedron,* 49, 4015–4034 (1993) and references therein and ring formations—*J.Heterocyclic Chem.,* 29, 1214 (1992) and references therein.

Substituted and unsubstituted tetrahydrobenzazepin-2-ones are known compounds which are prepared by reaction of α-tetralones with sodium azide under acidic conditions.

[*J. Chem. Soc.* 456 (1937); *Tetrahedron* 49, 1807 (1993)] (Schmidt reaction). Reduction of tetrahydro-1H-benzazepin-2-ones gives the tetrahydro-1H-benzazepines 48 which acylation gives compounds 49. Oxidation of N-acyl tetrahydro-1H-benzapines of type 49 to give the 5-one derivatives is a known oxidative procedure; R. L. Augustine and W. G. Pierson, *J. Org. Chem.,* 34, 1070 (1969).

The synthesis of 3,4-dihydro-1H-1-benzazepine-2,5-diones (52: $R_{15}$=H) has been reported as well as the conversion of 3,4-dihydro-1H-1-benzazepine-2,5-diones to 4-[(dimethylamino) methylene]-3,4-dihydro-1H-1-benzazepine-2,5-diones with N,N-dimethylformamide, dimethylacetal: (W.-Y. Chen and N. W. Gilman, *J. Heterocyclic Chem.,* 20, 663 (1983)]. The preceding reference describes the synthesis of 2-methyl-5,7-dihydropyrimido[5,4-d][1]benzazepin-6(6H)-ones which may be reduced to remove the lactam carbonyl group to give tricyclic derivatives of structural type 54 wherein Z is a pyrimidine ring.

Scheme 10

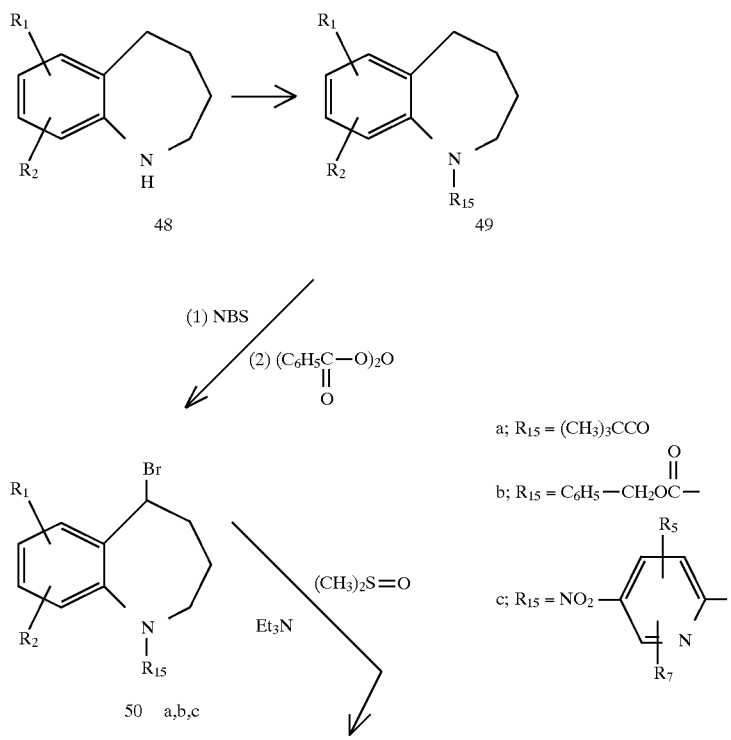

-continued
Scheme 10
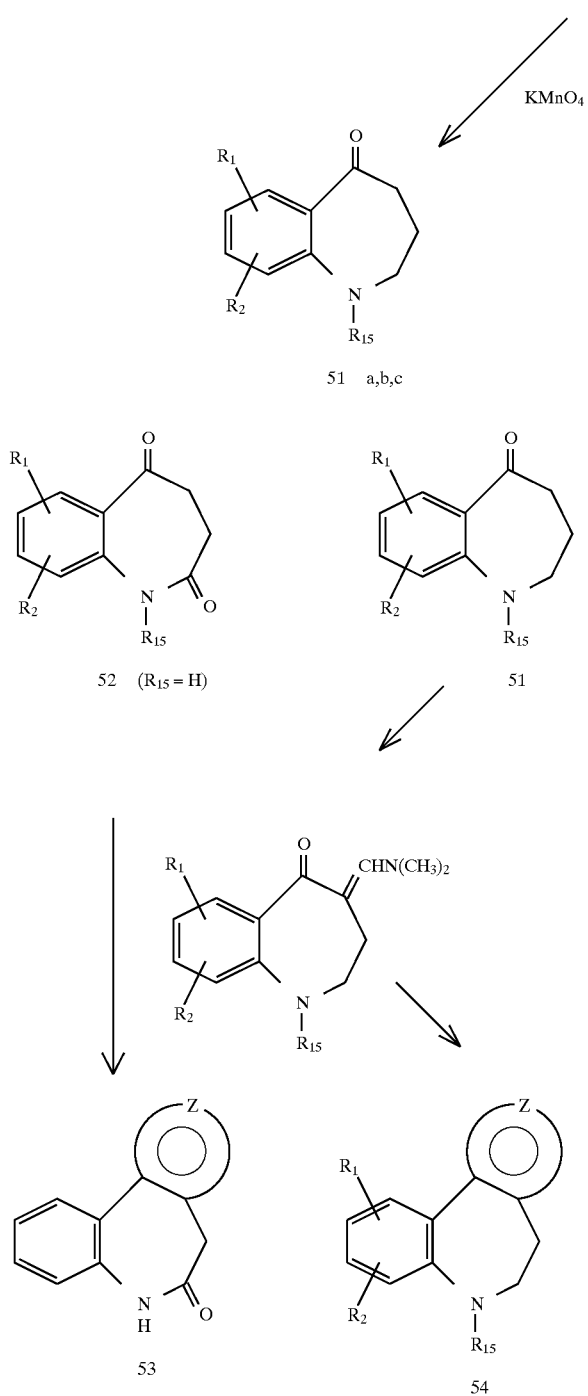

Scheme 11
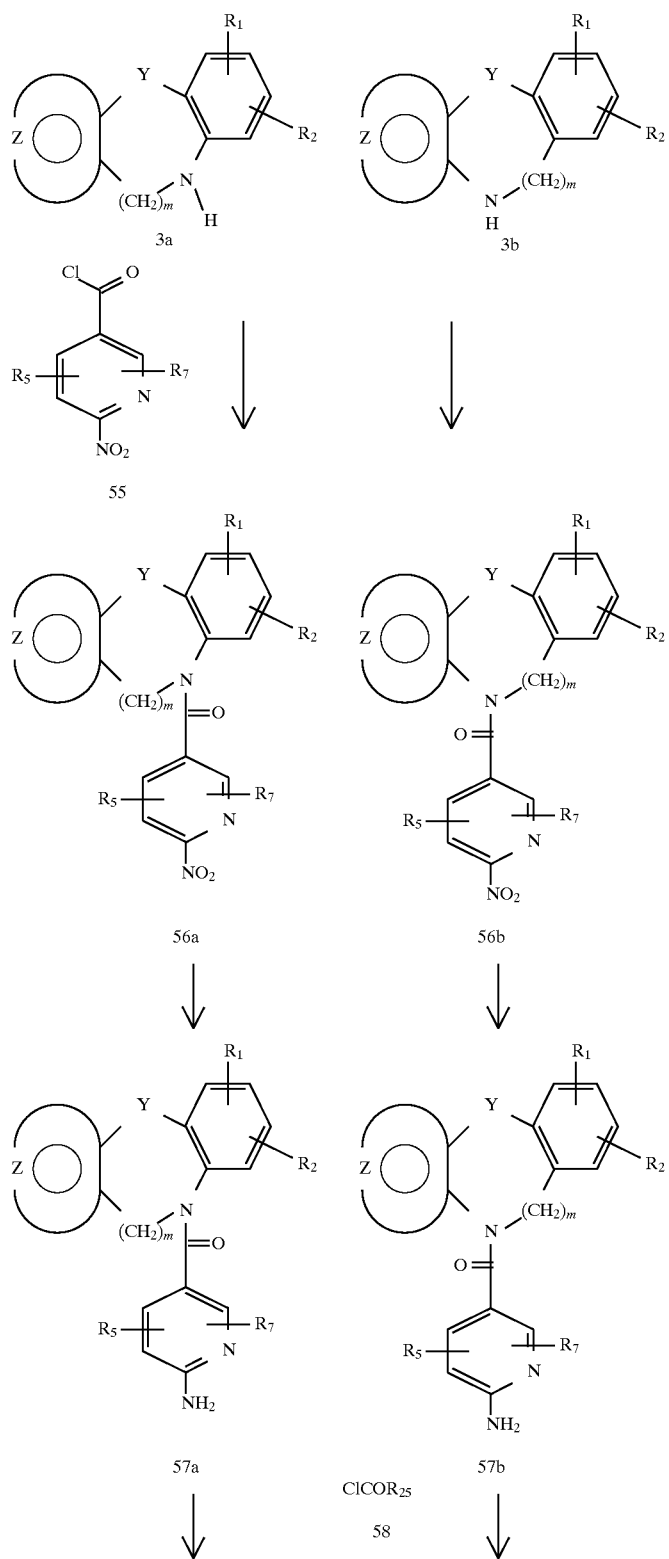

-continued
Scheme 11

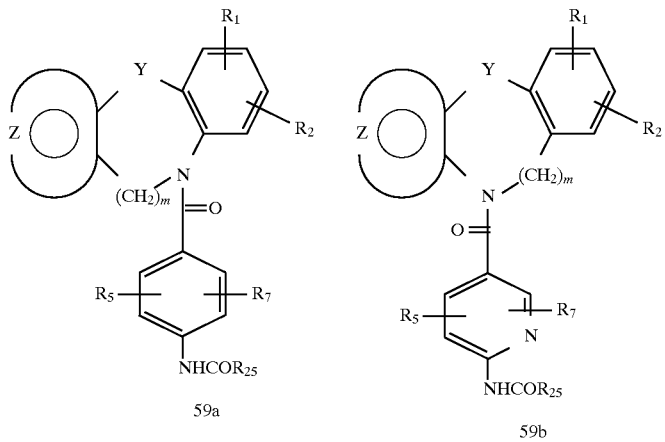

The compounds wherein the aryl group in the $R_3$ moiety —COAr is

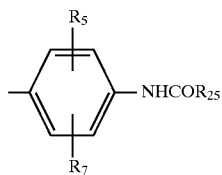

are prepared as shown in Scheme 11. The tricyclic derivatives 3a and 3b are reacted with a substituted or unsubstituted 4-nitrobenzoyl chloride 55 to give the derivatives 56a and 56b. Reductions of the nitro group in derivatives 56a and 56b gives the 4-aminobenzoyl intermediates 57a and 57b which are then reacted with an acid chloride represented by formula 58 to give the products 59a and 59b.

The compounds wherein the aryl group in the $R_3$ moiety —COAr is

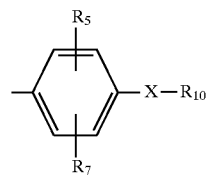

are prepared by reactin of tricyclic azepines 3a and 3b with a substituted benzoyl chloride illustrated by structural formula 60 (Scheme 12) to give the products 61a and 61b. In a similar manner reaction of heteroaroyl chlorides 62, 63, or 64 with the tricyclic azepines 3a and 3b gives the products 65a and 65b wherein the aryl groups are as illustrated in Scheme 13.

Scheme 12

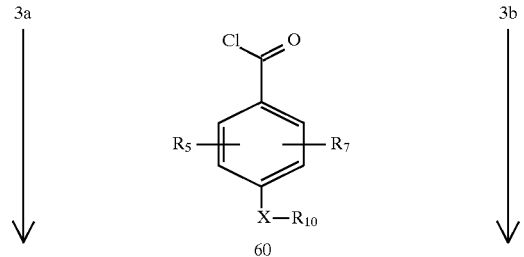

-continued
Scheme 12

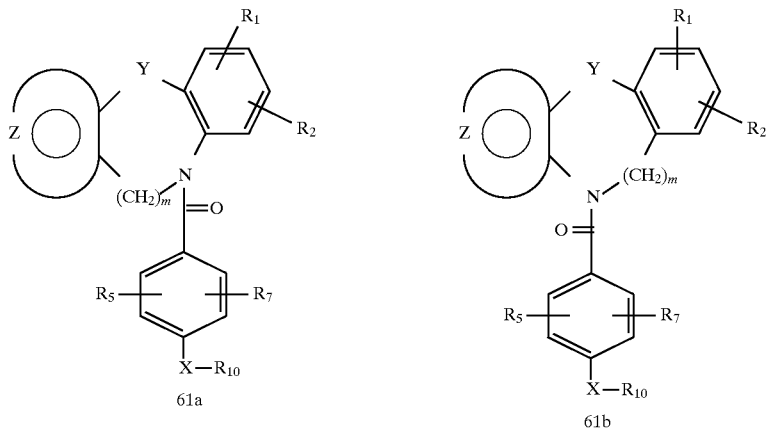

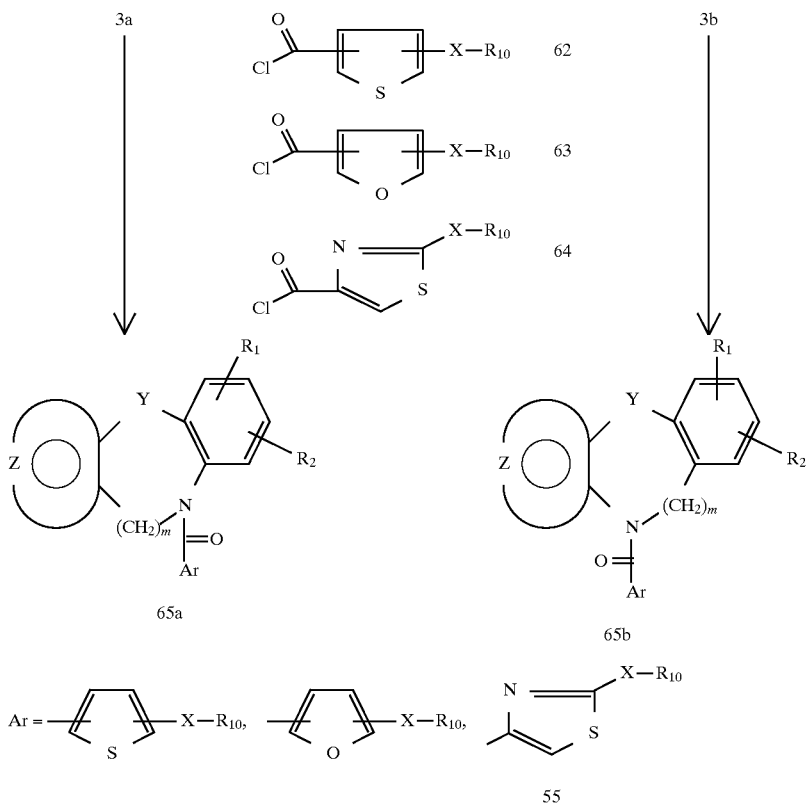

Reference Example 1

6,11-Dihydro-5H-dibenz[b,e]azepine

A mixture of 48.52 g (0.20 mol) of 2-aminobenzophenone-2'-carboxylic acid and 500 ml of xylene is refluxed for 67 hours, cooled to room temperature and filtered. The solid is washed with xylene to give 43.3 g (97.8%) of 5H-dibenz[b,e]azepine-6,11-dione as light tan crystals, m.p. 245°–248° C. To 4.46 g (0.020 mol) of the preceding compound in 25 ml of tetrahydrofuran is added 12 ml (0.12 mol) of a 10 molar solution of boron-dimethylsulfide in tetrahydrofuran. An additional 10 ml of tetrahydrofuran is added and the mixture is stirred overnight and then is refluxed (solids dissolve) for 4 hours. The solution is cooled and 15 ml of methanol added dropwise. The mixture is concentrated under vacuum, 50 ml of 2N sodium hydroxide is added and the mixture refluxed for 2 hours. The solid is filtered, washed with water, air dried and extracted with dichloromethane. The extract is dried ($Na_2SO_4$) and the solvent removed to give 3.25 g (83%) of crystals, m.p. 117°–122° C.

Reference Example 2

2-Chloro-5H-dibenz[b,e]azepine-6,11-dione

Chlorine gas is bubbled into a mixture (partial suspension) of 1.0 g (450 mmol) of 5H-dibenz[b,e]-azepine-6,11-dione in 50 ml of glacial acetic acid. The temperature of the mixture rises to 38° C. On standing, as the temperature of the solutions decreases, a white solid precipitates. The mixture is filtered to give 0.40 g of solid (mixture of starting material and product in ratio of 1:8). The filtrate on standing gives 0.10 g of product as crystals, m.p. 289°–293° C.

Reference Example 3

10,11-Dihydro-N,N-dimethyldibenz[b,f][1,4]oxazepine-2-sulfonamide

To 5.88 g of 10,11-dihydro-N,N-dimethyl-11-oxodibenz[b,f][1,4]oxazepine-2-sulfonamide in 5 ml of tetrahydrofuran is added 20 ml of a molar solution of borane-dimethylsulfide in tetrahydrofuran. The mixture is stirred overnight and then refluxed for 2 hours. The mixture is chilled, diluted with 10 ml of methanol and then concentrated, methanol added again and the mixture concentrated. To the mixture is added 20 ml of 2N NaOH and the mixture refluxed for 2 hours. The mixture is extracted with dichloromethane, the extract dried ($MgSO_4$) and filtered. The filtrate is passed through a thin pad of hydrous magnesium silicate and the pad washed with dichloromethane. The filtrate is concentrated to give 4.8 g of crystals. m.p. 99°–102° C. Recrystallization from diisopropylether-dichloromethane gives 3.96 g of crystals, m.p. 109°–110° C.

Mass Spectrum (FAB) 305(M+H).Anal.Calc'd. for $C_{15}H_{16}N_2O_3S$: C,59.2; H,5.3; N,9.2; S,10.6. Found: C,57.6; H,5.2; N,8.9; S,10.1.

Reference Example 4

2-Chloro-5,6-dihydrophenanthridine

To a hot (70° C.) solution of 2.62 g (17 mmol) of 6(5H)-phenanthridinone in 120 ml of acetic acid is added chlorine gas for 10 minutes. The solution is allowed to cool to room temperature and the mixture filtered. The crystals are filtered to give 1.35 g of crystals, m.p. 310°–318° C.

To the preceding compound (1.57 g) in 25 ml of tetrahydrofuran is added 12 ml of a 10 molar solution of boron-dimethylsulfide in tetrahydrofuran. The mixture is refluxed for 18 hours, cooled and 15 ml of methanol is added. The mixture is concentrated under vacuum and 50 ml of 2N sodium hydroxide added. The mixture is refluxed for 2 hours and the solid filtered off and washed with water and air dried to give the product as a solid.

Reference Example 5

9-Chloro-5H-dibenz[b,e]azepin-6,11-dione

A mixture of 11.15 g of 5H-dibenz[b,e]azepin-6,11-dione and 600 ml of glacial acetic acid is heated on a steam bath until the solid dissolves. To the solution (70° C.) is added chlorine gas. Chlorine is bubbled throughout the solution until a precipitate begins to form. The mixture is allowed to cool to room temperature and is filtered to give 7.3 g of product, m.p. 290° C. to 295° C.

Reference Example 6

9-Chloro-6,11-dihydro-5H-dibenz[b,e]azepine

To a mixture of 7.28 g 9-chloro-5H-dibenz-[b,e]azepin-6,11-dione in 25 ml of tetrahydrofuran under argon is added 8.5 ml of 10 molar boron-dimethylsulfide in tetrahydrofuran. The mixture is stirred 18 hours at room temperature, 30 ml of tetrahydrofuran added and the mixture refluxed for 3 hours (solids dissolved). The solution is cooled to room temperature and 25 ml of methanol added dropwise. The volatiles are removed under vacuum. To the residue is added 100 ml of 2N NaOH. The mixture is refluxed overnight and filtered. The solid is extracted with dichloromethane and the extract is washed with 2N citric acid, water and dried ($Na_2SO_4$). The solvent is removed to give 4.2 g of solid which is triturated with ethyl acetate-hexane (1:2) to give crystals, m.p. 137° C. to 141° C.

Reference Example 7

10,11-Dihydrodibenz[b,f][1,4]thiazepine

To a mixture of 3.3 g of 10,11-dihydro-11-oxodibenz[b,f][1,4]thiazepine in 25 ml of tetrahydrofuran is added 4.0 ml of 10 molar borane-dimethylsulfide in tetrahydrofuran. The mixture is stirred at room temperature for 18 hours, 50 ml of anhydrous methanol added and the solvent removed. An additional 30 ml of methanol is added and the solvent removed to give white crystals. A sample is purified by chromatography on silica gel with hexane-chloroformethyl acetate (2:1:1) as solvent to give white crystals, m.p. 145°–148° C.

The following compounds are prepared as described in Reference Example 7.

Reference Example 8

4-Methyl-10,11-dihydrodibenz[b,f][1,4]thiazepine

Reference Example 9

4-Chloro-10,11-dihydrodibenz[b,f][1,4]thiazepine

Reference 10

2-Methyl-10,11-dihydrodibenz[b,f][1,4]thiazepine

Reference Example 11

2-Chloro-10,11-dihydrodibenz[b,f][1,4]thiazepine

Reference Example 12

2-Methoxy-10,11-dihydrodibenz[b,f][1,4]thiazepine

Reference Example 13

8-Chloro-10,11-dihydrodibenz[b,f][1,4]thiazepine

Reference Example 14

4,8-Dichloro-10,11-dihydrodibenz[b,f][1,4]thiazepine

Reference Example 15

8-Chloro-4-methyl-10,11-dihydrodibenz[b,f][1,4]-thiazepine

Reference Example 16

8-Methoxy-10,11-dihydrodibenz[b,f][1,4]thiazepine

Reference Example 17

7-Chloro-4-methyl-10,11-dihydrodibenz[b,f][1,4]thiazepine

The following compounds are prepared as described in Reference Example 3.

Reference Example 18

2-Chloro-10,11-dihydrodibenz[b,f][1,4]-oxazepine

Reference Example 19

2-Methyl-10,11-dihydrodibenz[b,f][1,4]-oxazepine

Reference Example 20

4-Chloro-10,11-dihydrodibenz[b,f][1,4]-oxazepine

Reference Example 21

3-Methyl-10,11-dihydrodibenz[b,f][1,4]-oxazepine

Reference Example 22

7-Chloro-10,11-dihydrodibenz[b,f][1,4]-oxazepine

Reference Example 23

8-Chloro-10,11-dihydrodibenz[b,f][1,4]-oxazepine

Reference Example 24

2,4-Dichloro-10,11-dihydrodibenz[b,f][1,4]-oxazepine

Reference Example 25

4,8-Dichloro-10,11-dihydrodibenz[b,f][1,4]-oxazepine

Reference Example 26

4-Chloro-8-methyl-10,11-dihydrodibenz[b,f][1,4]-oxazepine

Reference Example 27

4-Methyl-7-chloro-10,11-dihydrodibenz[b,f][1,4]-oxazepine

Reference Example 28

1-Chloro-4-methyl-10,11-dihydrodibenz[b,f][1,4]-oxazepine

Reference Example 29

2-Fluoro-10,11-dihydrodibenz[b,f][1,4]-oxazepine

Reference Example 30

N-(2-Iodophenyl)-2-iodophenylacetamide

A solution of 13.32 g (0.05 mol) of 2-iodophenylacetic acid in 75 ml thionyl chloride is refluxed for 2 hours, and the volatiles removed under vacuum. Toluene is added (3 times) and the solvent removed under vacuum after each addition to give 2-iodophenylacetyl chloride as a gum. To the preceding compound (0.05 mol) in a mixture of 100 ml of toluene-dichloromethane (1:1) is added 11 g (0.05 mol) of 2-iodoaniline and (0.10 mol) of diisopropylethylamine.

The mixture is stirred at room temperature overnight and the solvent removed. The residue is dissolved in dichloromethane and the solution washed with 1N HCl, saturated sodium bicarbonate, brine and dried ($Na_2SO_4$). The solvent is removed and the residue recrystallized from methanol-ether to give 16.0 g of light brown crystals, m.p. 160°–163° C.

Reference Example 31

2-Iodo-N-(2-iodophenyl)benzeneethanamine

To a suspension of 1.39 g (3 mmol) of 2-iodo-N-(2-iodophenyl)benzeneacetamide in 30 ml of tetrahydrofuran-dichloromethane (1:1) is added 3.75 ml of 2.0 molar borane-dimethylsulfide in tetrahydrofuran. The solution is stirred 1 hour at room temperature and then refluxed for 16 hours. The mixture is cooled and water slowly added dropwise until gas evolution ceases. The volatile are removed under vacuum and the aqueous residue made alkaline with 2N sodium hydroxide. The mixture is extracted with ether (50 ml) and the extract is washed with brine and dried ($Na_2SO_4$). The solution is filtered through a thin pad of hydrous magnesium silicate and the filter pad is washed with ether and the filtrate evaporated. The residual solid is washed with isooctane to give 1.20 g of white solid. Recrystallization from diethylether/hexane gives white crystals.

Reference Example 32

N-(4-Nitrobenzoyl-N-(2-iodophenyl)-2-iodobenzeneethylamine

To a solution of 0.90 g of 2-iodo-N-(2-iodophenyl)benzeneethanamine in 4 ml of tetrahydrofuran is added 0.41 g of triethylamine, and 0.57 g of 4-nitrobenzoyl chloride. The mixture is stirred at room temperature for 2 hours and the solvent removed under vacuum. The residue is dissolved in ethyl acetate-dichloromethane (5:1) and the solution washed with 1N HCl, saturated $NaHCO_3$, brine and dried ($Na_2SO_4$). The solution is filtered through a thin pad of hydrous magnesium silicate. The filtrate is evaporated and the residual solid triturated with diethyl ether and hexane to give 1.10 g of product as a white solid.

Reference Example 33

3,4-Dihydro-1H-1-benzazepine-2,5-dione

To a solution of 225 ml of glacial acid and 8.5 ml of concentrated sulfuric acid is added 49.54 g (0.30 mol) of 2'-nitroacetophenone and 47.02 g (0.50 mol) of glyoxylic acid (hydrated). The mixture is heated at 100° C. for 16 hours. The mixture is cooled and poured over crushed ice. After the ice melts, the mixture is filtered and the solid washed with cold water. The solid is dried and recrystallized from dichloromethane-hexane to give 20.1 g of 3-(2-nitrobenzoyl)acrylic acid as white crystals, m.p. 153°–158° C. A solution of the proceeding compound (9.0 g) in 80 ml of ethanol and 1.6 g of palladium-on-carbon is hydrogenated in a Parr hydrogenator under 30 pounds per square inch of hydrogen for 20 hours. The mixture is filtered through diatomaceous earth and the solvent is removed. The residue (7.0 g) is chromatographed on silica gel with hexane-ethyl acetate (1:1) as solvent to give 4.0 g of 3-(2-aminobenzoyl)propionic acid as an orange solid, m.p. 103°–107° C. A 0.50 g sample of the preceding compound, 0.36 ml of triethylamine and 0.43 ml of diphenoxyphosphinyl cyanide in 20 ml of dichloromethane is stirred at room temperature for 5 days. The solvent is removed, ethyl acetate is added and the mixture washed with water, 2N citric acid, 1M $NaHCO_3$, brine and dried ($Na_2SO_4$). The solvent is removed and the residue purified by chromatography over silica gel with ethyl acetate-hexane (1:1) as solvent to give 0.190 g of light brown crystals, m.p. 168°–170° C.

Reference Example 34

4-[(Dimethylamino)methylene]-3,4-dihydro-1H-1-benzazepine-2,5-dione

A mixture of 0.250 g (1.43 mmol) of 3,4-dihydro-1 H-1-benzazepine-2,5-dione and 5.5 ml (4.93 g, 41.5 mmol)

of N,N-dimethylformamide, dimethylacetal is heated at 90° C. for 1.5 hour. The mixture is cooled, diluted with diethyl ether and filtered. The solid is washed well with diethyl ether and dried to give 0.26 g of tan crystals, m.p. 203°–205° C.

Reference Example 35

2-Methyl-6,7-dihydro-5H-pyrimido[5,4-d][1]benzazepine

To a solution of 0.308 g (3.26 mmol) of acetamidine hydrochloride in 15 ml of methanol under argon is added 0.176 g of (3.26 mmol) of sodium methoxide and the mixture stirred for 5 minutes. To the mixture is added 0.50 g (2.17 mmol) of 4-[(dimethylamino)methylene]-1,2,3,4-tetrahydro-5H-1-benzazepine-2,5-dione and the mixture stirred at room temperature overnight. The mixture (containing thick precipitate) is diluted with 3 ml of methanol, chilled and filtered. The filtrate is concentrated to dryness. The residue and original solid are combined and chloroform added. The mixture is washed with water, the organic layer is treated with activated carbon and then filtered through a thin pad of hydrous magnesium silicate. The filtrate is evaporated to give 0.41 g of crystals, m.p. 257°–258° C.

The preceding compound is heated with 5 equivalents of lithium hydride in dioxane for 24 hours to give the product as a solid.

Reference Example 36

5,6-Dihydropyrido[2,3-b][1,4]benzodiazepine

To a suspension of 11.67 g of 2-thiobenzoic acid in a mixture of 32 ml of ethanol and 11 ml of water is added portion wise 12.72 g of solid sodium bicarbonate. After the complete addition, the mixture is stirred for 15 minutes and 10.0 g of 2-chloro-3-nitropyridine added portionwise. The mixture is refluxed for 2 hours, cooled and then concentrated in vacuo. The residual aqueous solution is diluted with 15 ml of water, acidified with 2N HCl and extracted twice with 250 ml of ethyl acetate. The extract is concentrated under vacuum to give a yellow solid residue. The residue is dissolved in a minimum of ethyl acetate by heating on a steam bath. The solution is cooled overnight and filtered to give 2.5 g of starting material. The filtrate is concentrated, chilled and filtered to give 12.5 g of 2-(3-nitro-2-pyridinylthio)benzoic acid as a yellow solid. The preceding compound (5.0 g) and 0.75 g of Pd/C in 60 ml of ethanol is shaken in a Parr hydrogenator under 45 psi of hydrogen for 18 hours. The mixture is filtered through diatomaceous earth and the filter cake washed with 200 ml of dichloromethane. The combined filtrate is evaporated in vacuo to give a solid. The solid is triturated with ethanol and filtered to give 3.6 g of yellow solid. This solid (3.0 g) is again hydrogenated with Pd/C (0.50 g) in 50 ml of ethanol and 30 ml of acetic acid under 45 psi of hydrogen for 18 hours. The mixture is filtered through diatomaceous earth and the filter cake washed with methanol. The combined filtrate is concentrated in vacuo to give 1.6 g of solid. This solid in 25 ml of N,N-dimethylformamide is again reduced with 0.80 g of Pd/C under 45 psi of hydrogen to give 0.57 g of solid. Recrystallization from ethyl acetate gives 0.28 g of 2-(3-amino-2-pyridinylthio)benzoic acid. The preceding compound (0.20 g) is heated in 2-hydroxypyridine at 170° C. to give 5,6-dihydropyrido[2,3-b][1,4]benzothiazepine as a yellow solid. The preceding compound is reacted with borane-dimethylsulfide as described for Reference Example 3 to give the product as a solid.

Reference Example 37

2-Nitro-2'-carboxy-diphenylamine

A stirred solid mixture of 13.7 g of anthranilic acid, 20.2 g of o-bromonitrobenzene, 13.8 g of anhydrous potassium carbonate and 0.1 g of copper metal is heated at 200° C. in an oil bath. The reaction mixture is heated for 2 hours, cooled and the solid washed with ether (3×100 ml). The solid is dissolved in hot water and filtered. The filtrate is acidified with 40 ml of HCl and the resulting solid is collected and dried to give 20.5 g of the desired product as a solid, m.p. 262°–265° C.

Reference Example 38

2-Amino-2'-carboxy-diphenylamine

A solution of 7.3 g of 2-nitro-2'-carboxy-diphenylamine in 50 ml of methanol containing 10% palladium-on-carbon is hydrogenated under 42 pounds of pressure for 24 hours. The reaction mixture is filtered through diatomaceous earth. The filtrate is evaporated to dryness in vacuo to give 6.6 g of the desired product as a solid, m.p. 72°–75° C.

Reference Example 39

5,11-Dihydro-10H-dibenz[b,e][1,4]diazepine-11-one

A mixture of 6.6 g of 2-amino-2'-carboxydiphenylamine in 300 ml of xylene is heated at reflux for 20 hours. Tile xylene is evaporated in vacuo to a residue which is evaporated from 210 ml of toluene in vacuo to a residue which is evaporated from 50 ml of chloroform to give a residue. The residue is dissolved in 10 ml of tetrahydrofuran and added to 400 ml of ice-cold hexane. The resulting solid is collected, to give 4.3 g of the desired product as a solid, m.p. 121°–123° C.

Reference Example 40

5,11-Dihydro-10H-dibenz[b,e][1,4]diazepine

To a stirred solution of 4.3 g of 5,11-dihydro-10 H-dibenz[b,e][1,4]diazepin-11-one in 50 ml of tetrahydrofuran, under nitrogen and cooled to 0° C. is added 4.0 ml of a 10 molar solution of dimethyl sulfide-borane complex in tetrahydrofuran. The ice bath is removed after 30 minutes and the reaction mixture stirred at room for 18 hours. The reaction mixture is cooled in an ice bath and 30 ml of anhydrous methanol added dropwise and evaporated to dryness in vacuo. Another 30 ml of methanol is added and evaporated to a residue. The residue is quenched with 30 ml of 40% sodium hydroxide followed by heating at 110° C. for 45 minutes and cooling to room temperature. The reaction mixture is diluted with 200 ml of water and extracted with methylene chloride (3×100 ml). The combined extracts are washed with 1N HCl, water and 0.5N NaOH. The organic layer is dried and evaporated in vacuo to give 3.2 g of the desired product, m.p. 114°–116° C.

Reference Example 41

5H-Dibenz[b,e]azepine-6,11-dione

A mixture of 2.50 g of 2-aminobenzophenone-2'-carboxylic acid in 50 ml of xylene is stirred at reflux for 23 hours. The mixture is filtered to give 1.82 g of the desired product as a solid.

Reference Example 42

2-Chloro-5H-dibenz[b,e]azepine-6,11-dione

A mixture of 1.0 g of 5H-dibenz[b,e]azepine-6,11-dione in 50 ml of acetic acid is stirred while chlorine is bubbled into the reaction mixture until saturated. The temperature increases to 38° C. After standing, a precipitate forms and is filtered, washed with hexane and air dried to give 0.62 g of solid which is purified by chromatography to give the desired product as a solid, m.p. 289°–293° C.

Reference Example 43

2-Chloro-6,11-Dihydro-5H-dibenz[b,e]azepine

To a mixture of 7.28 g of 2-chloro-5 H-dibenz[(b,e]azepine-6,11-dione in 25 ml of anhydrous tetrahydrofuran, under argon, is added dropwise 8.5 ml of (10M) boron-dimethyl sulfide in tetrahydrofuran. The reaction mixture is stirred at room temperature for 18 hours. The reaction mixture is heated at reflux for 3 hours and cooled to room temperature. While stirring, 25 ml of methyl alcohol is carefully added, followed by 100 ml of 2N NaOH. The reaction mixture is heated at reflux for 24 hours and the solid collected. The solid is dissolved in methylene chloride and washed with 2N citric acid, water and dried ($Na_2SO_4$). The volatiles are evaporated in vacuo to give 4.16 g of a residue which is crystallized from ethyl acetate-hexane to give 2.05 g of the desired product as a crystalline solid, m.p. 137°–141° C.

Reference Example 44

2-[2-(Tributylstannyl)-3-thienyl]-1,3-dioxolane

To a stirred solution of 15.6 g (0.10 mol) of 2-(3-thienyl)-1,3-dioxolane in 100 ml of anhydrous ether, n-butyl-lithium (1.48N, in hexane, 74.3 ml) is added dropwise under nitrogen at room temperature. After being refluxed for 15 minutes, the reaction mixture is cooled to –78° C. and tri-n-butyltin chloride (34.18 g, 0.105 mol) in 100 ml of dry tetrahydrofuran is added dropwise. After the addition is complete, the mixture is warmed to room temperature and the solvent evaporated. To the oily residue 100 ml of hexane is added, and the resulting precipitate (LiCl) is filtered off. The filtrate is evaporated and the residue distilled at reduced pressure, given 34.16 g (77%) of the desired product.

Reference Example 45

2-[2-[(2-Nitrophenyl)methyl]-3-thienyl]-1,3-dioxolane

A mixture of 2-[2-(tributylstannyl)-3-thienyl]-1,3-dioxolane (8.8 gms, 20 mmols), 2-nitrobenzyl bromide (4.5 gms, 22 mmol) and tetrakis (triphenylphosphine)-palladium (0) (200 mg) is refluxed in degassed toluene for 16 hours under a nitrogen atmosphere. At the end, the reaction mixture is cooled to room temperature and filtered through diatomaceous earth. The toluene is removed by concentrating at reduced pressure and the product isolated by silica gel column chromatography by elution with 30% ethyl acetate: hexane to give 4.5 gms of the desired product as viscous liquid. Mass Spectrum; $M^+292$ Reference Example 46

4,10-Dihydro-5H-thieno[3,2-c][1]benzazepine

A stirred solution of 4 gms of 2-[2-[(2-nitrophenyl) methyl]-3-thienyl]-1,3-dioxolane in acetone (50 ml) and acetic acid (90% 50 ml) is heated to 60° C. Zinc dust (10 gms) is slowly added and after the addition, reaction mixture is stirred for 6 hours. At the end, reaction mixture is filtered and the residue washed with acetone and concentrated. The brown residue is extracted with chloroform and washed well with water. The organic layer is dried ($Na_2SO_4$) and filtered and concentrated. The product is isolated by silica gel column chromatography by eluting with 20% ethyl acetate: hexane to give 2.0 g of the desired product as a pale yellow crystalline solid, m.p. 86° C. Mass Spectrum; $M^+202$.

Reference Example 47

4,5-Dihydro-4,4-dimethyl-2-[3-[(2-nitrophenyl) methyl]-2-thienyl]oxazole

To a solution of 4,5-dihydro-4,4-dimethyl-2-(2-thienyl)-oxazole (4.5 gms 25 mmol) in anhydrous ether at –70° C., n-butyl-lithium (2.5 molar solution in hexane, 11 ml) is added drop by drop under $N_2$ atmosphere. The reaction mixture is stirred at –78° C. for 45 minutes and tri-n-butyltin chloride (8.3 gms 25 mmol) in dry ether is added drop by drop. The reaction mixture is stirred at room temperature for 1 hour and quenched with water. The reaction mixture is extracted with ether, washed well with water, dried and concentrated. The product obtained is pure enough for further transformation. The oil product, 4,5-dihydro-4,4-dimethyl-2-[3-(tributylstannyl)-2-thienyl]-oxazole is mixed with 2-nitrobenzyl bromide (5.5 g 25 mmol) in toluene and refluxed in the presence of tetrakis (triphenylphosphine)-palladium (0) 200 mg) for 16 hours. At the end reaction mixture is cooled to room temperature and filtered. Toluene is removed under reduced pressure and the product is isolated as brown oil by silica gel column chromatography by eluting it with 30% ethyl acetate:hexane to give 5.7 g of the desired product. Mass Spectrum; $M^+316$.

Reference Example 48

9,10-Dihydro-4H-thieno[3,2-c][1]benzazepin-10-one

A solution of 4,5-dihydro-4,4-dimethyl-2-[3-[(2-nitrophenyl)methyl]-2-thienyl]oxazole 5 gms is refluxed in acetone/water (3:1 100 ml) containing 1N HCl (30 ml) for 24 hours. The reaction mixture is concentrated and the residue is dissolved in glacial acetic acid (100 ml). The acetic acid is stirred at 70° C. and zinc dust (10 gm) is slowly added. Stirring is continued at 70° C. for 6 hours. At the end, the reaction mixture is cooled to room temperature and filtered. Acetic acid is removed under reduced pressure and the residue is extracted with chloroform. The chloroform layer is dried and concentrated to give 2.9 gms of the desired product as a brown solid. Mass Spectrum: $M^+215$.

Reference Example 49

9,10-Dihydro-4H-thieno[2,3-c][1]benzazepine

A stirred solution of 2.0 g of 9,10-dihydro-4 H-thieno[2,3-c][1]benzazepin-10-one and lithium aluminum hydride (500 mg) in tetrahydrofuran is refluxed for 4 hours. At the end, reaction mixture is carefully quenched with ice cold water and extracted with chloroform. The organic layer is washed well with water and dried over anhydrous $Na_2SO_4$, filtered and concentrated. The product is purified by silica gel column chromatography by eluting it with 30% ethyl acetate:hexane to give 1.2 g of the desired product as a bright yellow solid. Mass Spectrum $M^+202$.

Reference Example 50

2-Methylfurane-3-carbonyl chloride

A mixture of 4.0 g of methyl-2-methylfurane-3-carboxylate, 30 ml of 2N NaOH and 15 ml methanol is refluxed for 1.5 hours. The solvent is removed under vacuum to give a solid. The solid is extracted with dichloromethane (discarded). The solid is dissolved in water and the solution acidified with 2N citric acid to give a solid. The solid is washed with water and dried to give crystals 1.05 g of crystals of 2-methylfuran-3-carboxylic acid. The preceding compound (0.95 g) and 3 ml of thionyl chloride is refluxed for 1 hour. The solvent is removed, toluene added (20 ml, three times) and the solvent removed to give the product as an oil.

Reference Example 51

2-[2-(Tributylstannyl)-3-thienyl]-1,3-dioxolane

To a stirred solution of 15.6 g (0.10 mol) of 2-(3-thienyl)-1,3-dioxolane in 100 ml of anhydrous ether, n-butyl-lithium (1.48N, in hexane, 74.3 ml) is added dropwise under nitrogen at room temperature. After being refluxed for 15 minutes, the reaction mixture is cooled to −78° C. and tri-n-butyltin chloride (34.18 g, 0.105 mol) in 100 ml of dry tetrahydrofuran is added dropwise. After the addition is complete, the mixture is warmed to room temperature and the solvent evaporated. To the oily residue 100 ml of hexane is added, and the resulting precipitate (LiCl) is filtered off. The filtrate is evaporated and the residue distilled at reduced pressure, giving 34.16 g (77%) of the desired product.

Reference Example 52

Methyl 6-aminopyridine-3-carboxylate

Dry methanol (400 ml) is cooled in an ice bath and HCl gas is bubbled into the mixture for 25 minutes. To the MeOH-HCl is added 30 g of 6-aminopyridine-3-carboxylic acid and then the mixture is stirred and heated at 90° C. for 2 hours (all the solid dissolved) The solvent is removed under vacuum and the residual solid dissolved in 100 ml of water. The acidic solution is neutralized with saturated sodium bicarbonate (solid separated) and the mixture chilled and filtered to give 30 g of white crystals, m.p. 150°–154° C.

Reference Example 53

6-[(5-fluoro-2-methylbenzoyl)amino]pyridine-3-carboxylic acid

To a mixture of 4.5 g of methyl 6-aminopyridine-3-carboxylate and 5.53 ml of triethylamine in 40 ml of dichloromethane (cooled in an ice bath) is added 6.38 g of 5-fluoro-2-methylbenzoyl chloride in 10 ml of dichloromethane. The mixture is stirred at room temperature under argon for 18 hours and an additional 3.4 g of 5-fluoro-2-methylbenzoyl chloride added. After stirring at room temperature for 3 hours, the mixture is filtered to give 3.0 g of methyl 6-[[bis(5-fluoro-2-methylbenzoyl)]amino]pyridine-3-carboxylate. The filtrate is concentrated to dryness and the residue triturated with hexane and ethyl acetate to give an additional 9.0 g of bis acylated compound.

A mixture of 12.0 g of methyl 6-[[bis(5-fluoro-2-methylbenzoyl)]amino]pyridine-3-carboxylate, 60 ml of methanol-tetrahydrofuran (1:1) and 23 ml of 5N NaOH is stirred at room temperature for 16 hours. The mixture is concentrated under vacuum, diluted with 25 ml of water, cooled and acidified with 1N HCl. The mixture is filtered and the solid washed with water to give 6.3 g of the product as a white solid.

As described for Reference Example 53, but substituting the appropriate aroyl chloride, heteroaroyl chloride, cycloalkanoyl chlorides, phenylacetyl chlorides and related appropriate acid chlorides, the following 6-[(aroylamino] pyridine-3-carboxylic acids, 6-[(hetero-aroyl)amino] pyridine-3-carboxylic acids and related 6-[(acylated)amino] pyridine-3-carboxylic acids are prepared.

Reference Example 54

6-[(3-Methyl-2-thienylcarbonyl)amino]pyridine-3-carboxylic acid

Reference Example 55

6-[(2-Methyl-3-thienylcarbonyl)amino]pyridine-3-carboxylic acid

Reference Example 56

6-[(3-Methyl-2-furanylcarbonyl)amino]pyridine-3-carboxylic acid

Reference Example 57

6-[(2-Methyl-3-furanylcarbonyl)amino]pyridine-3-carboxylic acid

Reference Example 58

6-[(3-fluoro-2-methylbenzoyl)amino]pyridine-3-carboxylic acid

Reference Example 59

6-[(2-Methylbenzoyl)amino]pyridine-3-carboxylic acid

Reference Example 60

6-[(2-chlorobenzoyl)amino]pyridine-3-carboxylic acid

Reference Example 61

6-[(2-Fluorobenzoyl)amino]pyridine-3-carboxylic acid

Reference Example 62

6-[(2-Chloro-4-fluorobenzoyl)amino]pyridine-3-carboxylic acid

Reference Example 63

6-[(2,4-Dichlorobenzoyl)amino]pyridine-3-carboxylic acid

Reference Example 64

6-[(4-Chloro-2-fluorobenzoyl)amino]pyridine-3-carboxylic acid

Reference Example 65

6-[(3,4,5-Trimethoxybenzoyl)amino]pyridine-3-carboxylic acid

Reference Example 66

6-[(2,4-Difluorobenzoyl)amino]pyridine-3-carboxylic acid

Reference Example 67

6-[(2-Bromobenzoyl)amino]pyridine-3-carboxylic acid

Reference Example 68

6-[(2-Chloro-4-nitrobenzoyl)amino]pyridine-3-carboxylic acid

Reference Example 69

6-[(Tetrahydrofuranyl-2-carbonyl)amino]pyridine-3-carboxylic acid

Reference Example 70

6-[(Tetrahydrothienyl-2-carbonyl)amino]pyridine-3-carboxylic acid

Reference Example 71

6-[(Cyclohexylcarbonyl)amino]pyridine-3-carboxylic acid

Reference Example 72

6-[(cyclohex-3-enecarbonyl)amino]pyridine-3-carboxylic acid

Reference Example 73

6-[(5-Fluoro-2-methylbenzeneacetyl)amino]pyridine-3-carboxylic acid

Reference Example 74

6-[(2-Chlorobenzeneacetyl)amino]pyridine-3-carboxylic acid

Reference Example 75

6-[(cyclopentylcarbonyl)amino]pyridine-3-carboxylic acid

Reference Example 76

6-[(cyclohexylacetyl)amino]pyridine-3-carboxylic acid

Reference Example 77

6-[(3-Methyl-2-thienylacetyl)amino]pyridine-3-carboxylic acid

Reference Example 78

6-[(2-Methyl-3-thienylacetyl)amino]pyridine-3-carboxylic acid

Reference Example 79

6-[(3-Methyl-2-furanylacetyl)amino]pyridine-3-carboxylic acid, m.p. 288°–290° C.

Example 80

6-[(2-Methyl-3-furanylacetyl)amino]pyridine-3-carboxylic acid

Reference Example 81

6-[(3-Methyl-2-tetrahydrothienylacetyl)amino]pyridine-3-carboxylic acid

Reference Example 82

6-[(2-Methyl-3-tetrahydrothienylacetyl)amino]pyridine-3-carboxylic acid

Reference Example 83

6-[(2,5-Dichlorobenzoyl)amino]pyridine-3-carboxylic acid

Reference Example 84

6-[(3,5-Dichlorobenzoyl)amino]pyridine-3-carboxylic acid

Reference Example 85

6-[(2-Methyl-4-chlorobenzoyl)amino]pyridine-3-carboxylic acid

Reference Example 86

6-[(2,3-Dimethylbenzoyl)amino]pyridine-3-carboxylic acid

Reference Example 87

6-[(2-Methoxybenzoyl)amino]pyridine-3-carboxylic acid

Reference Example 88

6-[(2-Trifluoromethoxybenzoyl)amino]pyridine-3-carboxylic acid

Reference Example 89

6-[(4-Chloro-2-methoxybenzoyl)amino]pyridine-3-carboxylic acid

Reference Example 90

6-[[2-(Trifluoromethyl)benzoyl]amino]pyridine-3-carboxylic acid

Reference Example 91

6-[(2,6-Dichlorobenzoyl)amino]pyridine-3-carboxylic acid

Reference Example 92

6-[(2,6-Dimethylbenzoyl)amino]pyridine-3-carboxylic acid

Reference Example 93

6-[(2-Methylthiobenzoyl)amino]pyridine-3-carboxylic acid

Reference Example 94

6-[(4-Fluoro-2-(trifluoromethyl)benzoyl)amino]pyridine-3-carboxylic acid

Reference Example 95

6-[(2,3-Dichlorobenzoyl)amino]pyridine-3-carboxylic acid

Reference Example 96

6-[(4-Fluoro-2-methylbenzoyl)amino]pyridine-3-carboxylic acid

Reference Example 97

6-[(2,3,5-Trichlorobenzoyl)amino]pyridine-3-carboxylic acid

Reference Example 98

6-[(5-Fluoro-2-chlorobenzoyl)amino]pyridine-3-carboxylic acid

Reference Example 99

6-8 (2-Fluoro-5-(trifluoromethyl)benzoyl)amino]pyridine-3-carboxylic acid

Reference Example 100

6-[(5-Fluoro-2-methylbenzoyl)amino]pyridine-3-carbonyl chloride

A mixture of 6.2 g of 6-[(5-fluoro-2-methylbenzoyl)amino]pyridine-3-carboxylic acid and 23 ml of thionyl chloride is refluxed for 1 hour. An additional 12 ml of thionyl chloride is added and the mixture refluxed for 0.5 hour. The mixture is concentrated to dryness under vacuum and 30 ml of toluene added to the residue. The toluene is removed under vacuum and the process (add toluene and remove) is repeated to give 7.7 g of crude product as a solid.

As described for Reference Example 100, the following 6-(acyl)amino)pyridine-3-carbonyl chlorides are prepared.

Reference Example 101

6-[(3-Methyl-2-thienylcarbonyl)amino]pyridine-3-carbonyl chloride

Reference Example 102

6-[(2-Methyl-3-thienylcarbonyl)amino]pyridine-3-carbonyl chloride

Reference Example 103

6-[(3-Methyl-2-furanylcarbonyl)amino]pyridine-3-carbonyl chloride

Reference Example 104

6-[(2-Methyl-3-furanylcarbonyl)amino]pyridine-3-carbonyl chloride

Reference Example 105

6-[(3-Fluoro-2-methylbenzoyl)amino]pyridine-3-carbonyl chloride

Reference Example 106

6-[(2-Methylbenzoyl)amino]pyridine-3-carbonyl chloride

Reference Example 107

6-[(2-Chlorobenzoyl)amino]pyridine-3-carbonyl chloride, white crystals

Reference Example 108

6-[(2-Fluorobenzoyl)amino]pyridine-3-carbonyl chloride

Reference Example 109

6-[(2-Chloro-4-fluorobenzoyl)amino]pyridine-3-carbonyl chloride

Reference Example 110

6-[(2,4-Dichlorobenzoyl)amino]pyridine-3-carbonyl chloride

Reference Example 111

6-[(4-Chloro-2-fluorobenzoyl)amino]pyridine-3-carbonyl chloride

Reference Example 112

6-[(3,4,5-Trimethoxybenzoyl)amino]pyridine-3-carbonyl chloride

Reference Example 113

6-[(2,4-Difluorobenzoyl)amino]pyridine-3-carbonyl chloride

Reference Example 114

6-[(2-Bromobenzoyl)amino]pyridine-3-carbonyl chloride

Reference Example 115

6-[(2-Chloro-4-nitrobenzoyl)amino]pyridine-3-carbonyl chloride

Reference Example 116

6-[(Tetrahydrofuranyl-2-carbonyl)amino]pyridine-3-carbonyl chloride

Reference Example 117

6-[(Tetrahydrothienyl-2-carbonyl)amino]pyridine-3-carbonyl chloride

Reference Example 118

6-[(Cyclohexylcarbonyl)amino]pyridine-3-carbonyl chloride

Reference Example 119

6-[(Cyclohex-3-enecarbonyl)amino]pyridine-3-carbonyl chloride

Reference Example 120

6-[(2-Methylbenzeneacetyl)amino]pyridine-3-carbonyl chloride

Reference Example 121

6-[(2-Chlorobenzeneacetyl)amino]pyridine-3-carbonyl chloride

Reference Example 122

6-[(Cyclopentylcarbonyl)amino]pyridine-3-carbonyl chloride

Reference Example 123

6-[(Cyclohexylacetyl)amino]pyridine-3-carbonyl chloride

Reference Example 124

6-[(3-Methyl-2-thienylacetyl)amino]pyridine-3-carbonyl chloride

Reference Example 125

6-[(2-Methyl-3-thienylacetyl)amino]pyridine-3-carbonyl chloride

Reference Example 126

6-[(3-Methyl-2-furanylacetyl)amino]pyridine-3-carbonyl chloride

Reference Example 127

6-[(2-Methyl-3-furanylacetyl)amino]pyridine-3-carbonyl chloride

Reference Example 128

6-[(2-Methyl-5-fluorobenzeneacetyl)amino]pyridine-3-carbonyl chloride

Reference Example 129

6-[(3-Methyl-2-tetrahydrothienylacetyl)amino]pyridine-3-carbonyl chloride

Reference Example 130

6-[(2-Methyl-3-tetrahydrothienylacetyl)amino]pyridine-3-carbonyl chloride

Reference Example 131

6-[(2,5-Dichlorobenzoyl)amino]pyridine-3-carbonyl chloride

Reference Example 132

6-[(3,5-Dichlorobenzoyl)amino]pyridine-3-carbonyl chloride

Reference Example 133

6-[(2-Methyl-4-chlorobenzoyl)amino]pyridine-3-carbonyl chloride

Reference Example 134

6-[(2,3-Dimethylbenzoyl)amino]pyridine-3-carbonyl chloride

Reference Example 135

6-[(2-Methoxybenzoyl)amino]pyridine-3-carbonyl chloride

Reference Example 136

6-[(2-Trifluoromethoxybenzoyl)amino]pyridine-3-carbonyl chloride

Reference Example 137

6-[(4-Chloro-2-methoxybenzoyl)amino]pyridine-3-carbonyl chloride

Reference Example 138

6-[[2-(Trifluoromethyl)benzoyl]amino]pyridine-3-carbonyl chloride

Reference Example 139

6-[(2,6-Dichlorobenzoyl)amino]pyridine-3-carbonyl chloride

Reference Example 140

6-[(2,6-Dimethylbenzoyl)amino]pyridine-3-carbonyl chloride

Reference Example 141

6-[(2-Methylthiobenzoyl)amino]pyridine-3-carbonyl chloride

Reference Example 142

6-[(4-Fluoro-2-(trifluoromethyl)benzoyl)amino]pyridine-3-carbonyl chloride

Reference Example 143

6-[(2,3-Dichlorobenzoyl)amino]pyridine-3-carbonyl chloride

Reference Example 144

6-[(4-Fluoro-2-methylbenzoyl)amino]pyridine-3-carbonyl chloride

Reference Example 145

6-[(2,3,5-Trichlorobenzoyl)amino]pyridine-3-carbonyl chloride

Reference Example 146

6-[(5-Fluoro-2-chlorobenzoyl)amino]pyridine-3-carbonyl chloride

Reference Example 147

6-[(2-Fluoro-5-(trifluoromethyl)benzoyl)amino]pyridine-3-carbonyl chloride

As described for Reference Example 53, the following bis acylated products (Table A) are prepared and purified by silica gel chromatography. These compounds are then hydrolysed to the acids (Table B) as described in Reference Example 53.

TABLE A

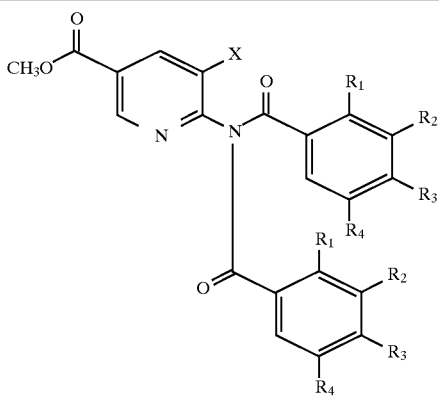

| Ref. Ex. No. | R₁ | R₂ | R₃ | R₄ | X | M⁺ |
|---|---|---|---|---|---|---|
| 148 | CH₃ | H | H | H | H | 388 |
| 149 | CH₃ | H | H | F | H | 424 |
| 150 | CH₃ | F | H | H | H | 426 |
| 151 | H | OCH₃ | OCH₃ | OCH₃ | H | 540 |
| 152 | Cl | H | H | H | H | 430 |
| 153 | F | H | F | H | H | 396 |
| 154 | Br | H | H | H | H | 520 |
| 155 | Cl | H | F | H | H | 412 |
| 156 | Ph | H | H | H | H | 512 |
| 157 | Cl | H | H | Br | H | 474 |
| 158 | CH₃ | H | H | F | Br | |
| 159 | CH₃ | H | H | H | Br | 468 |

M⁺ is molecular ion found from FAB mass spectrum

M⁺ is molecular ion found from FAB mass spectrum

TABLE B

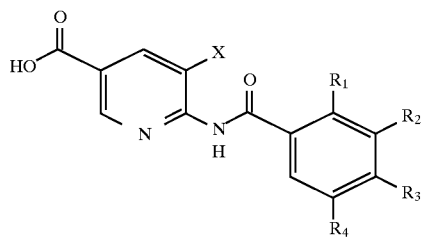

| Ref. Ex. No. | R₁ | R₂ | R₃ | R₄ | X | M⁺ |
|---|---|---|---|---|---|---|
| 160 | CH₃ | H | H | H | H | 256 |
| 161 | CH₃ | H | H | F | H | 274 |
| 162 | CH₃ | F | H | H | H | 274 |
| 163 | H | OCH₃ | OCH₃ | OCH₃ | H | 332 |
| 164 | Cl | H | H | H | H | 276 |
| 165 | F | H | F | H | H | 278 |
| 166 | Br | H | H | H | H | 322 |
| 167 | Cl | H | F | H | H | 294 |
| 168 | Ph | H | H | H | H | 318 |
| 169 | Cl | H | H | Br | H | 356 |
| 170 | CH₃ | H | H | F | Cl | |
| 171 | CH₃ | H | H | H | Br | 336 |

M⁺ is molecular ion found from FAB mass spectrum.

M⁺ is molecular ion found from FAB mass spectrum.

Reference Example 172

6-Amino-5-bromopyridine-3-carboxylic acid

To a stirred solution of 6-aminonicotinic acid (13.8 g, 0.1 mole) in glacial acetic acid (100 ml), bromine (16 g, 5 ml, 0.1 mole) in acetic acid (20 ml) is added slowly. The reaction mixture is stirred for 8 hours at room temperature and the acetic acid is removed under reduced pressure. The yellow solid residue is dissolved in water and carefully neutralized with 30% NH₄OH. The separated solid is filtered and washed with water to give 18 g of solid; mass spectrum: 218 (M⁺).

Reference Example 173

Methyl 6-amino-5-bromopyridine-3-carboxylate

6-Amino-5-bromopyridine-3-carboxylic acid (10 g, 50 mmol) is dissolved in saturated methanolic HCl (100 ml) and refluxed for 24 hours. The solvent, methanol, is re-moved under reduced pressure and the residue is dissolved in ice cold water. The aqueous solution is neutralized with 0.1N NaOH and the solid which separates is filtered; washed well with water and air dried to yield 10 g of product as a solid: mass spectrum 231 (M⁺).

Reference Example 174

6-[(2-Methylbenzeneacetyl)amino]pyridine-3-carboxylic acid

To a cooled (0° C.) mixture of 5.0 g methyl 6-aminopyridine-3-carboxylate, 12.6 ml of N,N-diisopropylethylamine in 40 ml of dichloromethane is added a solution of 12.2 g of 2-methylbenzeneacetyl chloride in 10 ml of dichloromethane. The mixture is stirred under argon at room temperature overnight. The mixture is diluted with 200 ml of dichloromethane and 50 ml of water and the organic layer separated. The organic layer is washed with 50 ml each of 1M NaHCO₃, brine and dried (Na₂SO₄). The solution is filtered through a thin pad of hydrous magnesium silicate and the filtrate concentrated to dryness. The residue (9.0 g) is chromatographed on a silica gel column with hexane-ethyl acetate (3:1) as eluent to give 8.6 g of solid. This solid, mainly methyl 6-[[bis(2-methylbenzeneacetyl)]-amino]pyridine-3-carboxylate, is dissolved in 60 ml of tetrahydrofuran-methanol (1:1) and 23 ml of 5N NaOH added to the solution. The mixture is stirred at room temperature overnight and the mixture concentrated under vacuum. Water (25 ml) is added and the mixture is stirred and acidified with cold 1N HCl. The mixture is chilled and the solid filtered and washed with water to give 5.9 g of off-white solid.

Reference Example 175

6-[(2-Methylbenzeneacetyl)amino]pyridine-3-carbonyl chloride

A mixture of 4.5 g of 6-[(2-methylbenzeneacetyl)amino] pyridine-3-carboxylic acid and 25 ml of thionyl chloride is refluxed for 1 hour and then concentrated to dryness under vacuum. To the residue is added 20 ml of toluene and the solvent removed under vacuum. The addition and removal of toluene is repeated and the residual solid dried at room temperature under vacuum to give 5.3 g of dark brown solid.

Reference Example 176

[1,1'-Biphenyl]-2-Biphenylcarbonyl chloride

A mixture of 5.6 g of [1,1'-biphenyl]-2-carboxylic acid and 29 ml of thionyl chloride is heated on a steam bath for 0.5 hour and the volatiles removed under vacuum. Toluene (40 ml) is added (twice) and the solvent removed under vacuum to give 6.8 g of a yellow oil.

Reference Example 177

Methyl 6-[[bis(1,1'-biphenyl]-2-ylcarbonyl)]amino]pyridine-3-carboxylate

To a chilled (0° C.) solution of 2.64 g of methyl 6-aminopyridine-3-carboxylate and 5.5 ml of diisopropylethylamine in 30 ml of dichloromethane under argon is added 6.8 g of [1,1'-biphenyl]-2-carbonyl chloride in 10 ml of dichloromethane. The mixture is stirred at room temperature 2 days and then diluted with 120 ml of dichloromethane and 50 ml of water. The organic layer is separated, washed with 50 ml each of 1 M NaHCO$_3$ and brine and dried (Na$_2$SO$_4$). The solution is filtered through a thin pad of hydrous magnesium silicate and the filtrate concentrated under vacuum to give a solid. Crystallization from ethyl acetate gives 6.2 g of white crystals, m.p. 180°–188° C.

Reference Example 178

6-[([1,1'-biphenyl]-2-ylcarbonyl)amino]pyridine-3-carboxylic acid

To a chilled (0° C.) mixture of 6.0 g of methyl 6-[[bis[(1,1'-biphenyl]-2-ylcarbonyl)]amino]pyridine-3-carboxylate in 40 ml of methanol and 30 ml of tetrahydrofuran is added slowly 10 ml of 2N NaOH, The mixture is stirred at room temperature overnight and brought to pH 5 with glacial acetic acid. The mixture is concentrated, acidified to pH 2–3 with 1N HCl and extracted with 250 ml of ethyl acetate. The extract is washed with 50 ml of brine, dried (Na$_2$SO$_4$) and the solvent removed under vacuum. The residual white solid is triturated with 15 ml of ethyl acetate to give 3.35 g of white crystals, m.p. 215°–217° C.

Reference Example 179

6-[1,1'-biphenyl]-2-ylcarbonyl)amino]pyridine-3-carbonyl chloride

A mixture of 1.9 g of 6-[([1,1'-biphenyl]-2-ylcarbonyl)amino]pyridine-3-carboxylic acid and 9 ml of thionyl chloride is refluxed for 1 hour and then concentrated to dryness under vacuum. Toluene (15 ml) is added (twice) to the residue and the solvent removed under vacuum to give 2.1 g of a light brown oil.

Reference Example 180

6-[(Cyclohexylcarbonyl)amino]pyridine-3-carboxylic acid

To a chilled (0° C.) solution of 5.0 g of methyl 6-aminopyridine-3-carboxylate and 12.6 ml of diisopropylethylamine in 50 ml of dichloromethane under argon is added a solution of 9.7 ml of cyclohexylcarbonyl chloride in 10 ml of dichloromethane. The mixture is stirred at room temperature overnight and diluted with 200 ml of dichloromethane and 60 ml of water. The organic layer is separated, washed with 60 ml of brine and dried (Na$_2$SO$_4$). The solution is filtered through a thin pad of hydrous magnesium silicate and the filtrate concentrated under vacuum to give 12.8 g of a solid.

The above solid (12.0 g) in a mixture of 150 ml of tetrahydrofuran-methanol (1:1) is chilled (0° C.) and 62 ml of 2N sodium hydroxide added. The mixture is stirred at room temperature for 3 hours, neutralized with 10 ml of glacial acetic acid and concentrated under vacuum. The mixture (containing solid) is acidified to pH 1 with 1N HCl and extracted with 250 ml of ethyl acetate and twice with 100 ml of ethyl acetate. The combined extract is washed with 100 ml of brine, dried (Na$_2$SO$_4$) and concentrated to a white solid. Trituration with hexane gives 6.5 g of product as a white solid.

Reference Example 181

Methyl-2-[(4-ethoxy-oxobutyl)amino]benzoate

A mixture of 19.2 g of methyl 2-aminobenzoate and 9.6 g of ethyl γ-bromobutyrate is heated at 80°–85° C. for 24 hours, cooled to room temperature and filtered. The solid is washed with CH$_2$Cl$_2$ and the filtrate washed with 1NHCl, H$_2$O, 1NNaHCO$_3$ and brine. The solvent is removed to give an oil. The oil is distilled and the fraction boiling at 45°–75° C. and 130°–160° C. were collected and discarded. The residue is the product (55.4 g of oil)

Reference Example 182

Methyl 2-[N-(4-ethoxy-4-oxobutyl)-N-(2-methylphenylsulfonyl)amino)benzoate

A mixture of 2.65 g of methyl 2-[(4-ethoxy-4-oxobutyl)amino]benzoate, 2.0 g of 2-methylphenylsulfonyl chloride and pyridine is heated on a steam bath for 16 hours. The mixture is concentrated under a vacuum (remove pyridine) and 1N HCl added. The mixture is extracted with dichloromethane and the extract washed with 1NHCl, H$_2$O, 1M NaHCO$_3$, brine and dried (Na$_2$SO$_4$). The solution is filtered through a thin pad of hydrons magnesium silicate and the filtrate evaporated to give 3.8 g of solid which is crystallized from ethanol to give crystals, m.p. 100°–102° C.

Reference Example 183

Methyl and Ethyl 1,2-Dihydro-5-hydroxy-1-[(4-methylphenyl)sulfonyl]-3H-1-benzazepine-4-carboxylate To a mixture of 0.448 g of potassium tert-butoride in 2 ml of tetrahydrofuran; cooled to 0° C. is added 0.838 g of methyl 2-[N-(4 ethoxy-4-oxobutyl)-N-(2-methylphenylsulfonyl)amino]benzoate in 12 ml of tetrahydrofuran. The mixture is stirred at 0° C. for 4 hours (under argon), poured into water and neutralized with 2N citric acid. The mixture is extracted with dichloromethane and the extract washed with H$_2$O, brine and dried (Mg SO$_4$). The extract is filtered through a thin pad of hydrous magnesium silicate and the filtrate concentrated to dryness to give 0.59 g of product (a mixture of methyl and ethyl esters).

Reference Example 184

1,2,3,4-tetrahydro-1-[(2-methylphenyl)sulfonyl]-5H-1-benzazepin-5-one

A 30 g sample of a mixture of methyl and ethyl 1,2-dihydro-5-hydroxy-1-[(4-methylphenyl)sulfonyl]-3H-1-benzazepine-4-carboxylate in a mixture of 171 ml of concentrated hydrochloric acid and 171 ml of glacial acetic acid is refluxed 24 hours. An additional 170 ml of concentrated hydrochloric acid is added and the mixture refluxed for 24 hours. The mixture is concentrated under vacuum to near dryness, diluted with water and the solution brought to pH 8 with saturated NaHCO$_3$. The mixture is extracted with dichloromethane and the extracted washed with H$_2$O, brine and dried (Na$_2$SO$_4$). The solution is filtered through a thin pad of hydrous magnesium silicate and the filtrate evaporated to give 12.0 g of a brown oil.

Reference Example 185

4-[(Dimethylamino)methylene]-1,2,3,4-tetrahydro-1-[(2-methylphenyl)sulfonyl]-5H-1-benzazepin-5-one A mixture of 1.89 g of 1,2,3,4-tetrahydro-1-[(2-methylphenyl)sulfonyl]-5H-1-benzazepin-5-one and 2.47 ml of tert-butoxy-bis(dimethylamino)methane (Bredericks reagent) in 10 ml of dichloromethane is heated under argon on a steam bath for 16 hours. The mixture is concentrated to dryness under vacuum and the residue dissolved in $CH_2Cl_2$. The solution is filtered through a thin pad of hydrous magnesium silicate and the pad washed with 5% ethyl acetate in $CH_2Cl_2$. The filtrate is concentrated to dryness and the residue (1.96 g) crystallized from $CH_2Cl_2$-hexane to give 0.85 g of crystals, m.p. 180°–185° C. A second crop of crystals (0.85 g) is recovered from the mother liquors and an additional 0.30 g is recovered from washing the pad of hydrous magnesium silicate with ethyl acetate.

Reference Example 186

1,4,5,6-tetrahydro-6-[(2-methylphenyl)sulfonyl]pyrazolo[4,3-d][1]benzazepine

A mixture of 1.55 g of 4-[(dimethylamino)-methylene]-1,2,3,4-tetrahydro-1-[(2-methylphenyl)-sulfonyl]-5H-1-benzazepin-5-one, 0.25 ml of hydrazine and 60 ml of ethanol is refluxed on a steam bath under argon for 2 hours. After standing overnight at room temperature, the solvent is removed under vacuum. The residue is dissolved in $CH_2Cl_2$ and the solution washed with water, brine and dried (($Na_2SO_4$). The solution is filtered through a thin pad of hydrous magnesium silicate and the filtrate evaporated to give 1.4 g of crystals, m.p. 76°–79° C.

On a larger scale reaction with 18.29 g of 4-[(dimethylamino)methylene]-1,2,3,4-tetrahydro-1-[(2-methylphenyl)sulfonyl]-5H-1-benzazepin-5-one the product in $CH_2Cl_2$ is filtered through a thin pad of hydrous magnesium silicate and the filter pad washed with ethyl acetate. The filtrate is concentrated to give 16.5 g of product (one spot by thin layer chromatography (silica gel) with hexane-ethyl acetate (1:2).

Reference Example 187

1,4,5,6-Tetrahydropyrazolo-[4,3-d][1]benzazepine

A mixture of 1.0 g of 1,4,5,6-tetrahydro-6-[(2-methylphenyl)sulfonyl]pyrazolo[4,3-d][1]benzazepine in 60 ml of 40% (V/v)$H_2SO_4$ in glacial acetic acid is heated at 60° C. for 12 hours or until the tosyl group is removed. The mixture is poured into 100 ml ice and water with cooling. Solid NaOH is added portionwise (temperature kept below 30° C.) with efficient stirring and the pH brought to 8. The mixture is extracted with ethyl acetate and the extract dried ($Na_2SO_4$) and the solvent removed to give a solid.

Reference Example 188

10,11-Dihydrobenz[b,f][1,4]oxazepine

To a slurry of 7.35 g of lithium aluminum hydride 100 ml of tetrahydrofuran is added in portions 10.0 g of dibenz[b,f][1,4]oxazepin-10(11H)-one. An additional 100 ml of tetrahydrofuran is added and the mixture is refluxed for 6 hours and then stirred at room temperature overnight. To the chilled mixture is added dropwise 7.5 ml of $H_2O$, 7.5 ml of 15% NaOH and three 7.5 ml portions of $H_2O$. The mixture is filtered and the filter cake washed with tetrahydrofuran and dichloromethane. The filtrate is concentrated to dryness under vacuum to give 10.1 g of solid. The solid is dissolved in dichloromethane and the solution filtered through a thin pad of hydrous magnesium silicate. The filter cake is washed with dichloromethane and the filtrate concentrated to dryness to give 8.9 g of solid. Crystallization from dichloromethane-hexane gives 7.5 g crystals, m.p. 69°–71° C.

Reference Example 189

Pyrido[2,3-b][1,4]benzoxazepin-6(5H)-one

A mixture of 21.4 g of phenyl salicylate, 25.71 g 3-amino-2-chloropyridine and 20 ml of 1,2,4-trichlorobenzene is refluxed for 1 hour under argon and the liberated phenol and HCl simultaneously distilled (from the refluxing mixture) and collected in a solution of 1N NaOH. The hot mixture is poured into 200 ml of ethanol and the precipitated solid collected by filtration. The solid is washed with ethanol and dried Recrystallization from methanol—DMF (6:1) gives 6.0 g of product, m.p. 268°–270° C.

Reference Example 190

5,6-Dihydropyrido[2,3-b][1,4]benzoxazepine

A mixture of 2.8 g of pyrido[2,3-b][1,4]benzoxazepin-6(5H)-one, 10 ml of tetrahydrofuran and 3 ml of 10M borane-dimethylsulfide in tetrahydrofuran is stirred at room temperature overnight and then refluxed for 3 hours. To the mixture is added dropwise under argon, 5 ml of methanol. The solvent is removed under vacuum and methanol added. The solvent is removed under vacuum and 12 ml of 2N NaOH added to the residue. The mixture is refluxed for 2 hours and extracted with ethyl acetate. The extract is washed with 2N citric acid, $H_2O$, brine and dried ($Na_2SO_4$). The solution is filtered through a thin pad of hydrous magnesium silicate and the filtrate concentrated to dryness under vacuum. The residue is chromatographed on a column (2"×18") of silica gel (32° g) with hexane-ethyl acetate (1:1) as solvent to give 0.78 g of crystals, m.p. 172°–174° C.

Reference Example 191

N-(2-Hydroxyphenyl)-2-chloro-3-pyridinecarboxamide

As described in J. Med. Chem., 37, 519 (1994), a solution of 1.09 g of 2-aminophenol in 15 ml of tetrahydrofuran is added dropwise to a mixture of 2.1 g of triethylamine and 2.33 g of 2-chloropyridine-3-carbonyl chloride hydrochloride in 10 ml of tetrahydrofuran. The mixture is stirred at room temperature for one hour under argon and then refluxed for one hour. The solvent is removed under vacuum and the residue triturated with water: The solid is filtered off and washed with water to give 1.02 g of solid. Recrystallization from 2-propanol gives crystals, m.p. 145°–146° C.

Reference Example 192

Pyrido[2,3-b][1,5]benzoxazepin-5(6H)one

A mixture of 13.0 g of N-(2-hydroxyphenyl)-2-chloro-3-pyridinecarboxamide and 2.82 g of sodium methoxide in 100 ml of N,N-dimethylformamide is refluxed under argon for 3 hours. Sodium methoxide (0.50 g) is added and the mixture refluxed 2 hours and then stirred at room temperature for 2 days. The solvent is removed under high vacuum and the red-brown residue triturated with cold methanol. The mixture is filtered and the solid washed with chilled methanol to give 5.0 g of white solid, m.p. 250°–253° C.

Reference Example 193

5,6-Dihydropyrido[2,3-b][1,5]benzoxazepine

To a stirred slurry of 0.886 g of lithium aluminum hydride in 20 ml of tetrahydrofuran is added 1.65 g of pyrido[2,3-b][1,5]benzoxazepin-5(6H)-one in portions. The mixture is diluted with 30 ml of tetrahydrofuran and refluxed under argon for 18 hours.

To the mixture is added 1 ml of water, 1 ml of 15% NaOH and three one-ml portions of $H_2O$ and the mixture is filtered. The solid is extracted with dichloromethane and the solution passed through a thin pad of hydrous magnesium silicate. The filtrate is concentrated to dryness to give crystals, m.p. 125°–129° C.

Reference Example 194

9,10-Dihydro-4H-thieno[2,3-c][1]benzazepine

To a solution of 9.0 g at 4,5-dihydro-4,4-dimethyl-2-(2-thienyl)oxazole in 200 ml of tetrahydrofuran, cooled to −78° C., is added 20 ml of a 2.5 molar solution of n-butyl lithium in hexane. The mixture is stirred −78° C. for 15 minutes and at 0° C. for 30 minutes. To the stirred solution is added 6.0 g of 2-methylbenzoxazepine-4-one. The mixture is stirred at room temperature for 16 hours quenched with ice cold water and extracted with chloroform. The extract is concentrated to dryness and 100 ml of 40% $H_2SO_4$ is added. The mixture is refluxed for 4 hours, cooled to room temperature and filtered to give 9,10-dihydro-4,10-dioxo-4H-thieno [2,3-c][1]benzazepine. The solid is washed with water to give 2.5 g of crystals. The solid is dissolved in 100 ml of dry tetrahydrofuran and 1.0 g of lithium aluminum hydride added. The mixture is refluxed for 16 hours, chilled and ice cold water is added dropwise. The mixture after dilution with water is extracted with chloroform-methanol (3:1) and the extract dried ($MgSO_4$). The solvent is removed and the residue chromatographed over silica gel with ethyl acetate-hexane (1:1) as solvent to give 1.8 g of solid; Mass spectrum (CI) 202 (M+H).

Reference Example 195

Methyl 4-[([1,1'-Biphenyl]-2-carbonyl)amino]-3-methoxybenzoate

A mixture of 10.0 g of [1,1'-biphenyl]-2-carboxylic acid in 75 ml of methylene chloride and 12.52 g of oxalyl chloride is stirred at room temperature for 15 hours. The volatiles are evaporated in vacuo to give 11.06 g of an oil. A 2.16 g portion of the above oil in 25 ml of methylene chloride is reacted with 1.81 g of methyl 4-amino-3-methoxybenzoate and 1.30 g of N,N-diisopropylethylamine by stirring at room temperature for 18 hours. The reaction mixture is washed with water, saturated aqueous $NaHCO_3$ and the organic layer dried($Na_2SO_4$). The organic layer is passed through hydrous magnesium silicate and hexane added to the filtrate at the boil to give 3.20 g of the desired product as a crystalline solid, m.p. 115°–117° C.

Reference Example 196

Methyl 4-[([1,1'-Biphenyl]-2-carbonyl)amino]-2-chlorobenzoate

A solution of 2.37 g of [1,1'-biphenyl]-2-carbonyl chloride in 10 ml of methylene chloride is added dropwise to an ice cold solution of 1.84 g of methyl 4-amino-2-chlorobenzoate and 1.49 g of N,N-diisopropylethylamine in 50 ml of methylene chloride. The reaction mixture is stirred at room temperature for 18 hours and washed with water, saturated aqueous $NaHCO_3$ and the organic layer dried ($Na_2SO_4$). The organic layer is passed through a pad of hydrous magnesium silicate and hexane added at the boil to give 1.1 g of the desired product as a crystalline solid, m.p. 132°–134° C. M+H=365

Reference Example 197

4-[([1,1'-Biphenyl]-2-carbonyl)amino]-2-chlorobenzoic Acid

A mixture of 3.0 g of methyl 4-[([1,1'-biphenyl]-2-carbonyl)amino]-2-chlorobenzoate in 75 ml of absolute ethanol and 2.0 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 0.1 g of the desired product as a crystalline solid, m.p. 217°–219° C.

Reference Example 198

4-[([1,1'-Biphenyl]-2-carbonyl)-amino]-3-methoxybenzoyl Chloride

A solution of 2.69 g of 4-[([1,1'-biphenyl]-2-carbonyl]amino]-3-methoxy benzoic acid in 5 ml of thionyl chloride is heated on a steam bath for 1 hour under Argon. The volatiles are removed in vacuo to give a residue which is stirred with hexane to give 2.58 g of crystalline solid, m.p. 121°–123° C. M+=361.

Reference Example 199

Methyl 4-[([1,1'-Biphenyl]-2-carbonyl)amino]benzoate

A mixture of 10.0 g of [1,1'-biphenyl]-2-carboxylic acid in 75 ml of methylene chloride and 12.52 g of oxalyl chloride is stirred at room temperature for 18 hours. The volatiles are evaporated in vacuo to give 11.66 g of an oil. A 7.5 g portion of the above oil in 25 ml of methylene chloride is added dropwise to a solution of 4.53 g of methyl-4-aminobenzoate and 4.3 g of N,N-diisopropylethylamine in 100 ml of methylene chloride at 0° C. The reaction mixture is stirred at room temperature for 18 hours and washed with water, and saturated aqueous $NaHCO_3$ and the organic layer dried($Na_2SO_4$). The organic layer is passed through hydrous magnesium silicate and hexane added to the filtrate at the boil to give 8.38 g of the desired product as a crystalline solid, m.p. 163°–165° C.

Reference Example 200

4-[([1,1'-Biphenyl]-2-carbonyl)amino]benzoic Acid

A 3.15 g sample of methyl 4-[([1,1'-biphenyl]-2-carbonyl) amino]benzoate is refluxed for 8 hours in 100 ml of ethyl alcohol and 2.5 ml of 10N sodium hydroxide. The cooled reaction mixture is acidified with [[? acid]] and the desired product collected and dried to give 2.9 g of the desired product as a solid m.p. 246°–249° C. M+H=318.

Reference Example 201

4-[([1,1'-Biphenyl]-2-carbonyl)amino]benzoyl Chloride

A mixture of 1.39 g of 4-[([1,1'-2-carbonyl)amino] benzoic acid in 2.0 ml of thionyl chloride is heated on a steam bath for 1 hour. Cold hexane is added and the crystalline solid collected and dried to give 1.34 g of the desired product, m.p. 118°–120° C.

Reference Example 202

2-(Phenylmethyl)benzoyl Chloride

A mixture of 5.0 g of 2-(phenylmethyl)benzoic acid in 5.0 ml of thionyl chloride is heated on a steam bath for 1 hour. The volatiles are evaporated in vacuo to give 5.74 g of the desired product as an oil. $M^+=227$ as methyl ester.

Reference Example 203

Methyl 4-[[2-(Phenylmethyl)benzoyl]amino]benzoate

To 3.03 g of methyl 4-aminobenzoate and 3.12 g of N,N-diisopropylethylamine in 75 ml of methylene to chloride is added 5.54 g of 2-(phenylmethyl)benzoyl chloride and the reactants stirred at room temperature for 18 hours. The reaction mixture is washed with water, saturated aqueous $NaHCO_3$ and the organic layer dried($Na_2SO_4$). The organic layer is passed through hydrous magnesium silicate two times and hexane added to the filtrate at the boil to give 5.04 g of the desired product as a crystalline solid, m.p. 138°–139° C.

Reference Example 204

Sodium 4-[[2-(Phenylmethyl)benzoyl]amino]benzoate

A mixture of 4.90 g of methyl 4-[[2-(phenylmethyl)benzoyl]amino]benzoate in 100 ml of absolute ethanol and 3.50 ml of 10N sodium hydroxide is heated on a steam bath for 3 hours. The aqueous phase is filtered and the resulting solid collected and dried to give 4.25 g of the desired product m.p. 340°–346° C.

Reference Example 205

4-[[2-(Phenylmethyl)benzoyl]amino]benzoic Acid

A mixture of 4.0 g sodium 4-[[2-(phenylmethyl)benzoyl]amino]benzoate is suspended in water and the pH adjusted to 5 with acetic acid. The solid is collected by filtration and dried at 80° C. in vacuo to give 3.75 g of the desired product, 246°–247° C. $M^+=332$.

Reference Example 206

4-[[2-(Phenylmethyl)benzoyl]amino]benzoyl Chloride

A mixture of 2.0 g of 4-[[2-(phenylmethyl)benzoyl]amino]benzoic acid in 2.0 ml of thionyl chloride is heated on a steam bath for 1 hour. The volatiles are evaporated in vacuo to give 1.53 g of the desired product as an oil. $M^+=346$ as methyl ester.

Reference Example 207

Methyl 4-[[2-Phenylmethyl)benzoyl]amino]-2-chlorobenzoate

A mixture of 5.0 g of 2-(phenylmethyl)benzoic acid in 5.0 ml of thionyl chloride is heated on a steam bath for 1 hour. The volatiles are evaporated in vacuo to give 5.70 g of an oil. A 2.85 g portion of the above oil in 25 ml of methylene chloride is added to a solution of 50 ml of methylene chloride containing 1.85 g of methyl 4-amino-2-chlorobenzoate and 1.65 g of N,N-diisopropylethylamine by stirring at room temperature for 18 hours. The reaction mixture is washed with water, saturated aqueous $NaHCO_3$ and the organic layer dried($Na_2SO_4$). The organic layer is passed through hydrous magnesium silicate two times and hexane added to the filtrate at the boil to give 2.96 g of the desired product as a crystalline solid, m.p. 133°–135° C. $M^+=380$.

Reference Example 208

Methyl 4-[[(2-Phenylmethyl)benzoyl]amino]-3-methoxybenzoate

A solution of 2.85 g of 2-(phenylmethyl)benzoyl chloride in 25 ml of methylene chloride is added dropwise to an ice cold solution of 1.84 g of methyl 4-amino-3-methoxybenzoate and 1.61 g of N,N-diisopropylethylamine in 50 ml of methylene chloride. The reaction mixture is stirred at room temperature for 18 hours and washed with water, saturated aqueous $NaHCO_3$ and the organic layer dried($Na_2SO_4$). The organic layer is passed through a pad of hydrous magnesium silicate and hexane added at the boil to give 2.2 g of the desired product as a crystalline solid, m.p. 129°–131° C. $M^+=376$.

Reference Example 209

2-Chloro-4-[[(2-Phenylmethyl)benzoyl]amino]benzoic Acid

A mixture of 2.8 g of methyl 2-chloro-4-[[(2-phenylmethyl)benzoyl]aminobenzoate in 75 ml of absolute ethanol and 1.84 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 2.6 g of the desired product as a crystalline solid, m.p. 184°–187° C. $M^+H=366$.

Reference Example 210

3-Methoxy-4-[[(2-phenylmethyl)benzoyl]amino]benzoic Acid

A mixture of 2.05 g of methyl 4-[[(2-phenylmethyl)benzoyl]amino]-3-methoxybenzoate in 75 ml of absolute ethanol and 1.4 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 1.87 g of the desired product as a crystalline solid, m.p. 176°–178° C. $M^+H=362$.

Reference Example 211

3-Methoxy-4-[[(2-phenylmethyl)benzoyl]amino]benzoyl Chloride

A mixture of 1.71 g of 3-methoxy-4-[[(2-phenylmethyl)benzoyl]amino]benzoic acid in 2.0 ml of thionyl chloride is heated on a steam bath under Argon for 1 hour and hexane added. The resulting solid is collected and dried to give 1.71 g of the desired product as a crystalline solid, m.p. 130°–135° C. $M^+=376$ as the methyl ester.

Reference Example 212

[4'-(Trifluoromethyl)-1,1'-biphenyl]-2-carbonyl Chloride

A mixture of 5.0 g of 4'-(trifluoromethyl)[1,1'-biphenyl]-2-carboxylic acid in 5.0 ml of thionyl chloride is heated on a steam bath under Argon for 1 hour and hexane added. The resulting solid is collected and dried to give 5.36 g of the desired product as a colorless oil. $M^+$=280 as methyl ester.

Reference Example 213

Methyl 4-[([4'-(trifluoromethyl)[1,1'-biphenyl] carbonyl)amino]benzoate

A solution of 3.13 g of [4'-(trifluoromethyl)[1,1'-biphenyl]-2-carbonyl chloride in 25 ml of methylene chloride is added dropwise to an ice cold solution of 1.84 g of methyl 4-aminobenzoate and 1.43 g of N,N-diisopropylethylamine in 50 ml of methylene chloride. The reaction mixture is stirred at room temperature for 18 hours and washed with water, saturated aqueous $NaHCO_3$ and the organic layer dried($Na_2SO_4$). The organic layer is passed through a pad of hydrous magnesium silicate and hexane added at the boil to give 3.36 g of the desired product as a crystalline solid, m.p. 164°–165° C. $M^+$=396.

Reference Example 214

3-Methoxy-4-[([4'-(trifluoromethyl)[1,1'-biphenyl]-2-carbonyl)amino]benzoyl Chloride A mixture of 2.0 g of 3-methoxy-4-[([4'-(trifluoromethyl)[1,1'-biphenyl]-2-carbonyl)amino]benzoic acid in 20 ml of thionyl chloride is heated on a steam bath under Argon for 1 hour and hexane added. The resulting solid is collected and dried to give 1.92 g of the desired product as a crystalline solid, m.p. 136°–138° C.

Reference Example 215

3-Methoxy-4-[([4'-trifluoromethyl)[1,1'-biphenyl]-2-carbonyl)amino]benzoic Acid

A mixture of 3.78 g of methyl 3-methoxy-4-[([4'-trifluoromethyl)[1,1'-biphenyl]-2-carbonyl)amino]benzoate in 75 ml of absolute ethanol and 2.20 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 3.49 g of the desired product as a crystalline solid, m.p. 213°–215° C.

Reference Example 216

Methyl 3-Methoxy-4-[([4'-trifluoromethyl)[1,1'-biphenyl]-2-carbonyl)amino]benzoate A solution of 3.56 g of (4'-(trifluoromethyl)[1,1'-biphenyl]-2-carbonyl chloride in 25 ml of methylene chloride is added dropwise to an ice cold solution of 1.81 g of methyl 4-amino-3-methoxybenzoate and 1.62 g of N,N-diisopropylethylamine in 50 ml of methylene chloride. The reaction mixture is stirred at room temperature for 18 hours and washed with water, saturated aqueous $NaHCO_3$ and the organic layer dried($Na_2SO_4$). The organic layer is passed through a pad of hydrous magnesium silicate and hexane added at the boil to give 3.9 g of the desired product as a crystalline solid, m.p. 112°–113° C.

Reference Example 217

2-Chloro-4-[([4'-(trifluoromethyl)[1,1'-biphenyl-2-carbonyl)amino]benzoyl Chloride A mixture of 1.39 g of 2-chloro-4-[([4'-(trifluoromethyl) [1,1'-biphenyl)-2-carbonyl)amino]benzoic acid in 2.0 ml of thionyl chloride is heated on a steam bath for 1 hour. The reaction mixture is concentrated to a residue in vacuo to a residue. Cold hexane is added to the residue and the solid collected and dried to give 1.39 g of the desired product.

Reference Example 218

2-Chloro-4-[([4'-(trifluoromethyl)[1,1'-biphenyl]-2-carbonyl)amino]benzoic acid

A mixture of 3.83 g of methyl 2-chloro-4-[([4'-(trifluoromethyl)[1,1'-biphenyl]-2-carbonyl)amino] benzoate in 75 ml of absolute ethanol and 2.20 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 3.42 g of the desired product as a crystalline solid, m.p. 187°–189° C.

Reference Example 219

Methyl 2-Chloro-4-[([4'-(trifluoromethyl)[1,1'-biphenyl]-2-carbonyl)amino]benzoate A solution of 3.56 g of [4'-(trifluoromethyl)[1,1'-biphenyl]-2-carbonyl chloride in 10 ml of methylene chloride is added dropwise to an ice cold solution of 1.86 g of methyl 2-chloro-4-aminobenzoate and 1.6 g of N,N-diisopropylethylamine in 50 ml of methylene chloride. The reaction mixture is stirred at room temperature for 18 hours and washed with water, saturated aqueous $NaHCO_3$ and the organic layer dried($Na_2SO_4$). The organic layer is passed through a pad of hydrous magnesium silicate(3×) and hexane added to the filtrate at the boil to give 4.0 g of the desired product as a crystalline solid, m.p. 130°–132° C.

Reference Example 220

4-[([4'-(Trifluoromethyl)[1,1'-biphenyl]carbonyl) amino]benzoic Acid

A mixture of 3.0 g of methyl 4-[([4'-(trifluoromethyl)[1, 1'-biphenyl]-2-carbonyl)amino]benzoate in 75 ml of absolute ethanol and 2.0 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 2.93 g of the desired product as a crystalline solid, m.p. 243°–245° C. $M^+$=385.

Reference Example 221

Methyl 6-[[3-(2-Methylpyridinyl)carbonyl]amino] pyridine-3-carboxylate

To a stirred solution of 3 g of methyl 6-aminopyridine-3-carboxylate and 4 ml of N,N-diisopropylethylamine in 100 ml of methylene chloride is added dropwise a solution of 6.4 g of 2-methylpyridine-3-carbonyl chloride in 25 ml of methylene chloride. The reaction mixture is stirred at room temperature for 2 hours and quenched with water. The organic layer is washed with water, dried($MgSO_4$), filtered and evaporated in vacuo to a residue which is stirred with ether and the resulting solid collected and air dried to give 6.8 g of the desired product. $M^+$=390.

Reference Example 222

6-[[3-(2-methylpyridinyl)carbonyl]amino]pyridine-3-carboxylic Acid

To a solution of 6.5 g of methyl 6-[[3-(2-methylpyridinyl) carbonyl]amino]pyridine-3-carboxylate in 100 ml of 1:1 tetrahydrofuran:methyl alcohol is added 20 ml of 5N NaOH. The reaction mixture is stirred overnight and evaporated in vacuo to a residue. The residue is dissolved in water and neutralized with acetic acid. The separated solid is filtered and air-dried to give 3.0 g of the desired product. $M^+$=257.

Reference Example 223

Methyl 6-[([1,1'-Biphenyl]-2-carbonyl)amino]-pyridine-3-carboxylate

To a solution of 1.5 g of methyl 6-aminopyridine-3-carboxylate in 100 ml of methylene chloride is added 3 ml of N,N-diisopropylethylamine at room temperature. To the stirred reaction mixture is slowly added a solution of 2.5 g of [1,1'-biphenyl]-2-carbonyl chloride. The reaction mixture is stirred at room temperature for 4 hours and then quenched with water. The organic layer is washed well with water and dried over anhydrous MgSO$_4$, filtered and evaporated in vacuo to a solid residue. The residue is stirred with ether, filtered and dried to give 3.0 g of the desired product:$M^+$= 332.

Reference Example 224

6-[([1,1'-Biphenyl]-2-carbonyl)amino]pyridine-3-carboxylic Acid

To a stirred solution of 2.5 g of methyl 6-[([1,1'-Biphenyl]-2-carbonyl)amino]-pyridine-3-carboxylate in 50 ml of 1:1 tetrahydrofuran:methanol is added 10 ml of 5N sodium hydroxide and the mixture stirred at room temperature for 16 hours. The reaction mixture is concentrated in vacuo to a residue which is dissolved in water and neutralized with acetic acid. The separated colorless solid is filtered and air dried to give 2.0 g of the desired product:$M^+$=318.

Reference Example 225

Methyl 2-(2-Pyridinyl)benzoate

A mixture of 12 g of methyl 2-(iodomethyl)benzoate, 20 g of n-butyl stannane and 2 g of tetrakis(triphenylphosphine) palladium (O) are refluxed in degassed toluene for 48 hours. The reaction mixture is concentrated in vacuo to a residue which is purified by column chromatography on silica gel by elution with 1:1 ethyl acetate:hexane to give 5.5 g of the desired product as an oil. $M^+$=213.

Reference Example 226

2-(2-Pyridinyl)benzoic Acid

A mixture of 3.0 g of methyl 2-(2-pyridinyl)benzoate and 600 mg of sodium hydroxide in 50 ml of 9:1 methanol:water is refluxed for 4 hours. The reaction mixture is concentrated in vacuo and the residue dissolved in 50 ml of cold water. The solution is neutralized with glacial acetic acid and the resulting product filtered, washed with water, and dried to give 2.5 g of the desired product:M+1=200.

EXAMPLE 1

N-[5-(Dibenz[b,f][1,4]oxazepin-10(11H)-ylcarbonyl)-2-pyridinyl]-5-fluoro-2-methylbenzamide To a stirred solution of 0.39 g of 10,11-dihydrodibenz[b,f][1,4]-oxazepine, 1.1 ml of triethylamine in 5 ml of dichloromethane is added 1.17 g of 6-[(5-fluoro-2-methylbenzoyl) amino]-pyridine-3-carbonyl chloride. The mixture is stirred under argon at room temperature for 16 hours, and diluted with 50 ml of dichloromethane and 20 ml of water. The organic layer is separated, washed with 20 ml each of 1M NaHCO$_3$, brine and dried (Na$_2$SO$_4$). The solution is filtered through a thin pad of hydrous magnesium silicate and the filtrate is concentrated to dryness under vacuum. The residue is chromatographed on silica gel with ethyl acetate-hexane (1:1) as solvent to give a solid. Crystallization from ethyl acetate gives 0.335 g of off-white crystals, m.p. 180°–186° C.

EXAMPLE 2

N-[5-[(9,10-Dihydro-4H-thieno[2,3-c][1]benzazepin-9-yl)carbonyl]-2-pyridinyl]-5-fluoro-2-methylbenzamide As described for Example 1, 9,10-dihydro-4-H-thieno[2,3-c][1]benzazepine in dichloromethane, in the presence of triethylamine is reacted with 6-[(5-fluoro-2-methylbenzoyl)amino]pyridine-3-carbonyl chloride to give the product as a non-crystalline yellow solid.

EXAMPLE 3

N-[5-[(4,10-Dihydro-5H-thieno[3,2-c][1]benzazepine-5-ylcarbonyl)-2-pyridinyl]-5-fluoro-2-methylbenzamide As described for Example 1, a mixture of 4,10-dihydro-5H-thieno[3,2-c][1]benzazepine and triethylamine in dichloromethane is reacted with 6-[(5-fluoro-2-methylbenzoyl)amino]pyridine-3-carbonyl chloride to give the product as a solid.

EXAMPLE 4

N-[5-(Pyrido[2,3-b][1,4]benzoxazepin-5(6H)-ylcarbonyl)-2-pyridinyl]-5-fluoro-2-methylbenzamide As described for Example 1, 5,6-dihydropyrido[2,3-b][1,4]benzoxazepine is reacted in dichloromethane, in the presence of triethylamine, with 6-[(5-fluoro-2-methylbenzoyl)amino]pyridine-3-carbonyl chloride to give the product as white crystals, m.p. 187°–189° C.

EXAMPLE 5

N-[5-(Pyrido[2,3-b][1,5]benzoxazepin-6(5H)-ylcarbonyl)-2-pyridinyl]-5-fluoro-2-methylbenzamide As described for Example 1, 5,6-dihydro[2,3-b][1,5]benzoxazepine reacted with 6-[(5-fluoro-2-methylbenzoyl)amino]dichloromethane in the presence of triethylamine to give the product as a non-crystalline solid.

EXAMPLE 6

N-[5-[(6,11-Dihydro-5H-dibenz[b,e]azepin-5-yl)carbonyl]-2-pyridinyl]-5-fluoro-2-methylbenzamide As described for Example 1, 6,11-dihydro-5H-dibenz[b,e]azepine is reacted in dichloromethane in the presence of triethylamine, with 6-[(5-fluoro-2-methylbenzoyl)amino]pyridine-3-carbonyl chloride to give the product as a solid.

EXAMPLE 7

N-[4,5-Dihydro-2-methylpyrazolo[4,3-d][1]benzazepin-6(2H)-yl)carbonyl-2-pyridinyl]-5-fluoro-2-methylbenzamide As described for Example 1, 2,4,5,6-tetra-hydro-2-methylpyrazolo[4,3-d][1]benzazepine is reacted in dichloromethane, in the presence of triethylamine, with 6-[(5-fluoro-2-methylbenzoyl)amino]pyridine-3-carbonyl chloride to give the product as a solid.

EXAMPLE 8

N-[5-[(6,7-Dihydro-5H-dibenz[b,d]azepin-5-yl)carbonyl]-2-pyridinyl]-5-fluoro-2-methylbenzamide As describe for Example 1, 6,7-dihydro-5H-dibenz[b,d]azepine is reaction in dichloromethane in the presence of triethylamine, with 6-((5-fluoro-2-methylbenzoyl)amino]pyridine-3-carbonyl chloride to give the product as a solid.

EXAMPLE 9

N-[5-[(4,5-Dihydro-6H-thieno[3,2-d][1]benzazepin-6-yl)carbonyl]-2-pyridinyl]-5-fluoro-2-methylbenzamide As described for Example 1, 4,5-dihydro-6H-thieno[3,2-d][1]benzazepine is reacted in dichloromethane, in the presence of triethylamine, with 6-[(5-fluoro-2-methylbenzoyl)amino]pyridine-3-carbonyl chloride to give the product as a solid.

EXAMPLE 10

N-[5-[(5,10-Dihydro-4H-thieno[3,2-c][2]benzazepin-4-yl)carbonyl]-2-pyridinyl]-5-fluoro-2-methylbenzamide As described for Example 1, 5, 10-dihydro-4H-thieno[3,2-c][2]benzazepine in dichloromethane in the presence of triethylamine is reacted with 6-[(5-fluoro-2-methylbenzoyl)amino]pyridine-3-carbonyl chloride to give the product as a solid.

EXAMPLE 11

N-[5[(4,5-Dihydropyrazolo[4,3-d][1]benzazepin-6(1H)-yl)carbonyl]-2-pyridinyl]-5-fluoro-2-methylbenzamide To a solution of 0.20 mol of 1,4,5,6-tetrahydropyrazolo[4,3-d][1]benzazepine, 0.80 mol of triethylamine is added 0.42 mol of 6-[(5-fluoro-2-methylbenzoyl)amino]pyridine-3-carbonyl chloride in 15 ml of dichloromethane. The mixture is stirred under argon for 16 hours and diluted with dichloromethane (25 ml). The mixture is washed with $H_2O$, 1MNaHCO$_3$, brine and dried (Na$_2$SO$_4$). The solvent is removed and the residue in methanol-tetrahydrofurane(1:1) stirred with 1NNaOH for 5 hours. The mixture is neutralized with acetic acid and the solvent removed. To the residue is added $H_2O$ and the mixture extracted with ethyl acetate. The extract is washed with $H_2O$, 1NHCl, 1MNaHCO$_3$ and dried (Na$_2$SO$_4$). The solvent removed under vacuum and the residue chromatographed on silica gel with ethyl acetate-hexane as solvent to give the product as a solid.

EXAMPLE 12

N-[5-[(6,11-Dihydro-5H-dibenz[b,e]azepin-5-yl)carbonyl]-2-pyridinyl][1,1'-biphenyl]-2-carboxamide To a chilled (0° C.) solution of 0.293 g of 6,11-dihydro-5H-dibenz[b,e]azepine and 625 μL triethylamine in 3.5 ml of dichloromethane is added a solution of 0.657 g of 6-[([1,1'-biphenyl]-2-ylcarbonyl)amino]-3-pyridinecarbonyl chloride in 1.5 ml of dichloromethane. The mixture is stirred under argon at room temperature for 16 hours and diluted with 40 ml of dichloromethane and 20 ml of water. The organic layer is separated and washed with 20 ml each of 1M NaHCO$_3$, brine and dried (Na$_2$SO$_4$). The solution is filtered through a thin pad of hydrous magnesium silicate and the filtrate concentrated to dryness under vacuum. The residual solid is chromatographed on silica gel with ethyl acetate-hexane ( 1:1) as solvent to give the product as a glass. Crystallization from ethyl acetate gives 0.395 g of white crystals, m.p. 134°–142° C.

EXAMPLE 13

N-[5-[(4,5-Dihydro-2-methylpyrazolo[4,3-d][1]benzazepin-6(2H)-yl)carbonyl]-2-pyridinyl][1,1'-biphenyl]-2-carboxamide As described for Example 12, 2,4,5,6-tetrahydro-2-methylpyrazolo[4,3-d][1]benzazepine is reacted with 6-[([1,1'biphenyl]-2-ylcarbonyl)amino]-3-pyridinecarbonyl chloride to give the product as a solid.

EXAMPLE 14

N-[5-[(6,7-Dihydro-5H-dibenz[b,d]azepin-5-yl)carbonyl]-2-pyridinyl][1,1'-biphenyl]-2-carboxamide As described for Example 12, 6,7-dihydro-5H-dibenz[b,d]azepine is reacted with 6-[([1,1'-biphenyl]-2-ylcarbonyl)amino]-3-pyridinecarbonyl chloride to give the product as a solid.

EXAMPLE 15

N-[5-[(4,5-Dihydro-6H-thieno[3,2-d][1]benzazepin-6-yl)carbonyl]-2-pyridinyl][1,1'-biphenyl]-2-carboxamide As described for Example 12, 4,5-dihydro-6H-thieno[3,2-d][1]benzazepine is reacted with 6-[([1,1'-biphenyl]-2-ylcarbonyl)amino]-3-pyridinecarbonyl chloride to give the product as a solid.

EXAMPLE 16

N-[5-[(5,10-Dihydro-4H-thieno[3,2-c][2]benzazepin-4-yl)carbonyl]-2-pyridinyl][1,1'-biphenyl]-2-carboxamide As described for Example 12, 5,10-dihydro-4H-thieno[3,2-c][2]benzazepine is reacted with 6-[([1,1'-biphenyl]-2-ylcarbonyl)amino]-3-pyridinecarbonyl chloride to give the product as a solid.

EXAMPLE 17

N-[5-[(9,10-Dihydro-4H-thieno[2,3-c][1]benzazepin-9-yl)carbonyl]-2-pyridinyl][1,1'-biphenyl]-2-carboxamide As described for Example 12, 9,10-dihydro-4H-thieno[2,3-c][1]benzazepine is reacted with 6-[([1,1'-biphenyl]-2-ylcarbonyl)amino]-3-pyridinecarbonyl chloride to give the product as a solid.

EXAMPLE 18

N-[5-[(4,10-Dihydro-5H-thieno[3,2-c][1]benzazepin-5-yl)carbonyl]-2-pyridinyl][11'biphenyl]-2-carboxamide As described for Example 12, 4,10-dihydro-5H-thieno[3,2-c][1]benzazepine is reacted with 6-[([1,1'- biphenyl]-2-ylcarbonyl)amino]-3-pyridinecarbonyl chloride to give the product as a solid.

EXAMPLE 19

N-[5-[(4,5-Dihydropyrazolo[4,3-d][1]benzazepin-6(1H)-yl)carbonyl]-2-pyridinyl]-[1,1'-biphenyl]-2-carboxamide As described for Example 11, 1,4,5,6-tetrahydropyrazolo[4,3-d][1]benzazepine is reacted with 6-[([1,1'-biphenyl]-2-ylcarbonyl)amino-3-pyridinecarbonyl chloride to give the product as a solid.

EXAMPLE 20

N-[5-[(6,11-Dihydro-5H-pyrido[2,3-b][1,5]benzodiazepin-6-yl)carbonyl]-2-pyridinyl]-2-methylfurane-3-carboxamide To a cooled (0° C.) solution of 0.296 g of 6,11-dihydro-5H-pyrido[2,3-b][1,5]benzodiazepine and 624 µL of triethylamine in 3 ml of dichloromethane is added a solution of 6-[(2-methyl-3-furanylcarbonyl)amino]-3-pyridinecarbonyl chloride in 4 ml of dichloromethane. The mixture is stirred at room temperature for 16 hours and the solvent removed under vacuum. To the residue is added 1M $NaHCO_3$ and the mixture extracted with ethyl acetate. The extract is washed with $H_2O$, 1M $NaHCO_3$ brine and dried ($Na_2SO_4$). The solvent is removed under vacuum and the residue chromatographed on silica gel with ethyl acetate-hexane as solvent to give the product as a solid.

EXAMPLE 21

N-[5-[5(6H)-phenanthridinyl)carbonyl]-2-pyridinyl]-2-methylfurane-3-carboxamide As described for Example 20, 5,6-dihydrophenanthridine is reacted with 6-[(2-methyl-3-furanylcarbonyl)amino]-3-pyridinecarbonyl chloride to give the product as a solid.

EXAMPLE 22

N-[5-[(5,11-Dihydro-10H-dibenz[b,e][1,4]diazepin-10-yl)carbonyl]-2-pyridinyl]-2-methylfurane-3-carboxamide As described for Example 20, 5,11-dihydro-10H-dibenz[b,e][1,4]diazepine is reacted with 6-[(2-methyl-3-furanylcarbonyl)amino]-3-pyridinecarbonyl chloride to give the product as a solid.

EXAMPLE 23

N-[5-[(5,11-Dihydro-10H-dibenz[b,e][1,4]diazepin-10-yl)carbonyl]-2-pyridinyl][1,1'-biphenyl]-2-carboxamide As described for example 12, 5,11-dihydro-10H-dibenz[b,e][1,4]diazepine is reacted with 6-[([1,1'-biphenyl]-2-ylcarbonyl)amino]-3-pyridinecarbonyl chloride to give the product as a solid.

EXAMPLE 24

5-(4-(4-Butyloxy)benzoyl-6,11-dihydro-5H-dibenz[b,e]azepine

To a solution of 6,11-dihydro-5H-dihydro-5H-dibenz[b,e]azepine (0.12 g, 0.6 mmol) in methylene chloride (2 ml) is added triethylamine (0.12 g, 1.2 mmol), followed by 4-butoxybenzoyl chloride ((0.15 g, 0.72 mmol). The resulting mixture is stirred at room temperature for 2 hours, and then treated with 4 ml of 1N NaOH. The mixture is extracted with ethyl acetate (10 ml), and the extract is washed with 1N sodium hydroxide and brine (5 ml), dried over anhydrous sodium sulfate, and filtered through hydrous magnesium silicate. The filtrate is evaporated, and the crude material is triturated with isoctane to give 0.24 g of white solid; Mass spectrum (CI), 372(MH$^+$)

EXAMPLE 25

10-(1,1'Biphenyl]-4-ylcarbonyl)-5,11-dihydro-10H-dibenzo-[b,e][1,4]diazepine To a cooled (0° C.) solution of 0.5 g of 5,11-dihydro-10H-dibenzo[b,e][1,4]diazepine in 50 ml of $CH_2Cl_2$ and 12 ml of disopropylethylamine is added dropwise a solution of 0.67 g of [1,1'-biphenyl]-4-carbonyl chloride in 50 ml of $CH_2Cl_2$. The mixture is stirred at room temperature for 16 hours. An additional 0.3 g of [1,1]-biphenyl]-4-carbonyl chloride in 30 ml of $CH_2Cl_2$ is added and the mixture stirred at room temperature 16 hours. The volatiles are removed under vacuum and the residue dissolved in 150 ml of $CHCl_3$. The solution is washed with 50 ml of $H_2O$, dried ($Na_2SO_4$) and the solvent removed. The residue is chromatographed on silica gel with ethyl acetate-hexane (1:5) and ethyl acetate-hexane (1:3) as solvent to give 0.86 g of solid, m.p. 152°0–154° C.; Mass spectrum (CI), 377 (MH$^+$).

EXAMPLE 26

10-([1,1'-Biphenyl]-4-ylcarbonyl)-10,11-dihydrodibenz[b,f][1,4]oxazepine

To a cooled (0° C.) solution of 1.0 g of 10,11-dihydrodibenz[b,f][1,4]oxazepine and 7 ml of triethylamine in 30 ml of $CH_2Cl_2$ under argon is added dropwise 2.0 g of [1,1'-biphenyl]-4-carbonyl chloride. The mixture is stirred at room temperature for 16 hours and diluted with 50 ml of $CHCl_3$. The mixture is washed with 30 ml each of $H_2O$, 2NHCl, $H_2O$, saturated $NaHCO_3$, $H_2O$, and dried ($Na_2SO_4$). Solvent is removed under vacuum to give 1.6 g of a yellow solid, m.p. 93°–95° C; Mass spectrum (CI), 378(MH$^+$).

EXAMPLE 27

9-([1,1'-Biphenyl]-4-ylcarbonyl)-9,10-dihydro-4H-thieno[2,3-c][1]benzazepine As described for Example 26, 9,10-dihydro-41H-thieno[2,3-c][1]benzazepine is reacted with [1,1'-biphenyl]-4-carbonyl chloride to give the product as a yellow solid; Mass spectrum (CI) 381 (MT).

EXAMPLE 28

5-([1,1'-Biphenyl]-4-ylcarbonyl)-6,7-dihydro-5H-dibenz[b,d]azepine

As described for Example 26, 6,7-dihydro-5H-dibenz[b,d]azepine is reacted with [1,1'-biphenyl]-4-carbonyl chloride to give the product as a solid.

EXAMPLE 29

6-([1,1'-Biphenyl]-4-ylcarbonyl)5,11-dihydro-6H-pyrido[2,3-e][1]benzazepine

As described for Example 26, 5,111-dihydro-6H-pyrido[2,3-e][1]benzazepine is reacted with [1,1'-biphenyl]-4-carbonyl chloride to give the product as a solid.

EXAMPLE 30

5-([1,1'-Biphenyl]-4-ylcarbonyl)-5,6-dihydropyrido
[2,3-b][1,4]benzothiazepine

As described for Example 26, 5,6-dihydropyrido[2,3-b][1,4]benzothiazepine is reacted with [1,1'-biphenyl]-4-carbonyl chloride to give the product as a solid.

EXAMPLE 31

10-([1,1'-Biphenyl]-4-ylcarbonyl)-10,11-dihydro[b,f][1,4]thiazepine

As described for Example 26, 10,11-dihydro[b,f][1,4]-thiazepine is reacted with [1,1'-biphenyl]-4-carbonyl chloride to give the product as a solid.

EXAMPLE 32

10-(4-Benzoylbenzoyl)-10,11-dihydrodibenz[b,f][1,4]oxazepine

As described for Example 26, 10,11-dihydrodibenz[b,f][1,4]oxazepine is reacted with 4-(benzoyl)benzoyl chloride to give the product as an off-white, m.p. 103°–106° C.; Mass spectrum (CI), 406 (MH$^+$).

EXAMPLE 33

5-(4-Benzoylbenzoyl)5,6,11,12-tetrahydrodibenz[b,f]azocine

As described for Example 26, 5,6,11,12-tetrahydrodibenz[b,f]azocine is reacted with 4-(benzoyl)benzoyl chloride to give the product as a solid, m.p. 89°–92° C., Mass spectrum (CI), 418(MH$^+$)

EXAMPLE 34

10-[4-(Benzoylbenzoyl)-10,11-dihydro[b,f][1,H]thiazepine

As described for Example 26, 10,11-dihydro[b,f][1,4]thiazepine is reacted with 4-(benzoyl chloride to give the product as a solid.

EXAMPLE 35

5-[4-(Benzoylbenzoyl)-5,6-dihydropyrido[2,3-b][1,4]benzothiazepine

As described for Example 26, 5,6-dihydropyrido[2,3-b][1,4]benzothiazepine is reacted with 4-(benzoyl)benzoyl chloride to give the product as a solid.

EXAMPLE 36

6-[(4-Benzoylbenzoyl)]5,11-dihydro-6H-pyrido[2,3-e][1]benzazepine

As described for Example 26, 5,11-dihydro-6H-pyrido[2,3-e][1]benzazepine is reacted with 4-(benzoyl)benzoyl chloride to give the product as a solid.

EXAMPLE 37

5-[(4-Benzoylbenzoyl)]3-6,7-dihydro-5H-dibenz[b,d]azepine

As described for Example 26, 6,7-dihydro-5H-dibenz[b,d]azepine is reacted with 4-(benzoyl)benzoyl chloride to give the product as a solid.

EXAMPLE 38

9-[(4-Benzoylbenzoyl)]-9,10-dihydro-4H-thieno[2,3-c][1]benzazepine

As described for Example 26, 9,10-dihydro-4H-thieno[2,3-c][1]benzazepine is reacted with 4-(benzoyl)benzoyl chloride to give the product as a solid.

EXAMPLE 39

5-[(4-Benzoylbenzoyl)]-4,10-dihydro-5H-thieno[3,2-c][1]benzazepine

As described for Example 26, 4,10dihydro-5H-thieno[3,2-c][1]benzazepine is reacted with 4-(benzoyl)benzoyl chloride to give the product as a solid.

EXAMPLE 40

5-([1,1'-Biphenyl]-4-ylcarbonyl)-4,10-dihydro-5H-thieno[3,2-c][1]benzazepine

As described for Example 26, 4,10-dihydro-5H-thieno[3,2-c][1benzazepine is reacted with [1,1'biphenyl]-4-carbonyl chloride to give the product as a solid.

EXAMPLE 41

6-([1,1'-Biphenyl]-4-ylcarbonyl]-1,4,5,6-tetrahydropyrazolo[4,3-d][1]benzazepine As described for Example 26, 2 mmol of 1,4,5,6-tetrahydropyrazolo[4,3-d][1]benzazepine is reacted with 5 mmol of [1,1'-biphenyl]-4-carbonyl chloride. The product is stirred in methanol with 2N NaOH for 16 hours and the mixture concentrated and extracted with ethyl acetate. The extract is washed with 1M citric acid, NaHCO$_3$, H$_2$O, dried (Na$_2$SO$_4$) and the solvent removed to give the product of the example as a solid.

EXAMPLE 42

N-[4-[(5,6-Dihydropyrazolo-[4,3-d][1]benzazepin-6(1H)-yl)carbonyl]-3-chlorophenyl][1,1'-biphenyl]-2-carboxamide As described for Example 11, 6-(2-chloro-4-aminobenzoyl)-1,4,5,6-tetrahydropyrazolo[4,3-d][1]benzazepine is reacted with [1,1'-biphenyl]-4-carbonyl chloride to give the product as a solid.

EXAMPLE 43

N-[4-[(5,6-Dihydropyrazolo[4,3-d][1]benzazepin-6(1H)-ylcarbonyl]-3-chlorophenyl]-2-(dimethylamino)pyridine-3-carboxamide As described for Example 11, 6-(2-chloro-4-aminobenzoyl)-1,4,5,6-tetrahydropyrazolo[4,3-d]benzazepine is reacted with 2-(dimethylamino)pyridine-3-carbonyl chloride to give the product of the example as a solid.

EXAMPLE 44

N-[4-[(5,6-dihydropyrazolo[4,3-d][1]benzazepin-6(1H)-yl)carbonyl]phenyl]-2-(dimethylamino)pyridine-3-carboxamide As described for Example 11, 6-(4-aminobenzoyl)-1,4,5,6-tetrahydropyrazolo-[4,3-d]benzazepine is reacted with

EXAMPLE 45

N-[5-[5,6,11,12-tetrahydrodibenz[b,f]azocin-5-yl) carbonyl]-2-pyridinyl]-5-fluoro-2-methylbenzamide To a cooled (0° C.) and stirred solution of 0.246 g of 5,6,11,12-tetrahydrodibenz[b,f]azocine 695 µL of triethylamine in 5 ml of dichloromethane is added 0.586 g of 6-[(5-fluoro-2-methylbenzoyl)aminopyridine-3-carbonyl chloride. The mixture is stirred 16 hours under argon, diluted with 50 ml of dichloromethane and 20 ml of water, and the organic layer separated. The organic layer is washed with 20 ml each of NaHCO$_3$, brine and dried (Na$_2$SO$_4$). The solution is passed through a thin pad of hydrous magnesium silicate and the filtrate concentrated to dryness under vacuum. The residue (450 mg) is chromatographed on silica gel preparative plates to give a solid. Crystallization from ethyl acetate gives 0.20 g of white crystals, m.p. 198°–200° C.

EXAMPLE 46

N-[4-(Dibenz[b,f][1,4]oxazepin-10(11H)-ylcarbonyl)-phenyl][1,1'-biphenyl]-2-carboxamide To a mixture of 0.197 g of 10,11-dihydrodibenz[b,f][1,4] oxazepine and 0.402 g of 4-[([1,1'-biphenyl]-2-carbonyl) amino]benzoyl chloride in 5 ml of dichloromethane (cooled in ice bath) is added dropwise 0.154 g of N,N-diisopropylethylamine in 2 ml of dichloromethane. The mixture is stirred at room temperature under argon for 2 hours. The mixture is poured into water and the organic layer separated. The organic extract is washed with 2N Na$_2$CO$_3$, water, brine and dried (Na$_2$SO$_4$). The solution is filtered through a thin pad of hydrous magnesium silicate and the filter cake washed with dichloromethane. The filtrate is concentrated to dryness to give 0.65 g of solid. The solid is purified by thick layer chromatography on silica gel with hexane-ethyl acetate (2:1) as solvent to give 0.110 g of a glass, m.p. 107° C.–122° C. Anal. Found: C, 80.8; H, 4.9; N,6.0.

EXAMPLE 47

N-[4-(Dibenz[b,f][1,4]oxazepin-10(11H)-ylcarbonyl)-3-chlorophenyl][1,1'biphenyl]-2-carboxamide A mixture of 0.263 g of 10,11-dihydro-10(4-amino-2-chlorobenzoyl)dibenz[b,f][1,4]oxazepine, 0.195 g of [1,1'-bipheny]-2-carbonyl chloride and 0.116 g of N,N-diisopropylethylamine in 7 ml of dichloromethane is stirred at room temperature for 3 hours. The mixture is poured into water and extracted with dichloromethane. The extract is washed with 2N Na$_2$CO$_3$, water, brine and dried (Na$_2$SO$_4$). The solution is filtered through a thin pad of hydrous magnesium silicate (pad washed with dichloromethane). The filtrate is concentrated to dryness to give a yellow solid. The solid is purified by chromatography on thick layer silica gel plates with hexane-ethyl acetate (1:1) as solvent to give 0.12 g of a yellow glass, m.p. 145° C.–188° C.: Anal.found: C, 73.6; H, 4.6; N,5.0; Cl, 6.4.

EXAMPLE 48

N-[5-(Dibenz[b,f][1,4]oxazepin-10(11H)ylcarbonyl) -2-pyridinyl]-5-fluoro-2-methylbenzamide As described for Example 46, 10,11-dihydrodibenz[b,f] [1,4]oxazepine is reacted in dichloromethane with 2-[(2-methyl-5-fluorobenzoyl)amino]-5-pyridinylcarbonyl chloride in the presence of N,N-diisopropylethylamine to give the product as crystals. m.p. 180° C.–186° C.

As described for Example 46 the following compounds can be prepared.

EXAMPLE 49

N-[4-(Dibenz[b,f][1,4]oxazepin-10(11H)-ylcarbonyl)-phenyl]-2-(2-pyridinyl)benzamide

EXAMPLE 50

N-[4-(Dibenz[b,f][1,4]oxazepin-10(11H)-ylcarbonyl)-phenyl]-2-(3-pyridinyl)benzamide

EXAMPLE 51

N-[4-(Dibenz[b,f][1,4]oxazepin-10(11H)-ylcarbonyl)-phenyl]-2-(4-pyridinyl)benzamide

EXAMPLE 52

N-[4-(Dibenz[b,f][1,4]oxazepin-10(11H)-ylcarbonyl)-3-chlorophenyl]-2-(2-thienyl)benzamide

EXAMPLE 53

N-[4-Dibenz[b,f][1,4]oxazepin-10(11H)-ylcarbonyl) -3-chlorophenyl]-2-(3-thienyl)benzamide As described for Example 48 the following compounds can be prepared.

EXAMPLE 54

N-[5-(Dibenz[b,f][1,4]oxazepin-10(11H)-ylcarbonyl)-2-pyridinyl]-2-chloro-5-fluorobenzamide

EXAMPLE 55

N-[5-(Dibenz[b,f][1,4]oxazepin-10(11H)-ylcarbonyl)-2-pyridinyl]-2-methyl-3-fluorobenzamide

EXAMPLE 56

N-[5-(Dibenz[b,f][1,4]oxazepin-10(11H)-ylcarbonyl-)-2-pyridinyl]-2-methylbenzamide

EXAMPLE 57

N-[5-(Dibenz[b,f][1,4]oxazepin-10(11H)-ylcarbonyl)-2-pyridinyl]-2-chloro-3-pyridinylcarboxamide

EXAMPLE 58

N-[5-(Dibenz[b,f][1,4]oxazepin-10(11H)-ylcarbonyl)-2-pyridinyl]-2-hydroxybenzamide

EXAMPLE 59

N-[5-(Dibenz[b,f][1,4]oxazepin-10(11H)-ylcarbonyl)-2-pyridinyl]-2-(dimethylamino)benzamide

EXAMPLE 60

N-[5-(Dibenz[b,f][1,4]oxazepin-10(11H)-ylcarbonyl)-2-pyridinyl]-2-(dimethylamino)-3-pyridinylcarboxamide

EXAMPLE 61

N-[5-(Dibenz[b,f][1,4]oxazepin-10(11H)-ylcarbonyl)-2-pyridinyl]-2-fluoro-5-chlorobenzamide

EXAMPLE 62

N-[5-(Dibenz[b,f][1,4]oxazepin-10(11H)-ylcarbonyl)-2-pyridinyl][1,1-biphenyl]-2-carboxamide

EXAMPLE 63

N-[5-(Dibenz[b,f][1,4]-oxazepin-10(11H)-ylcarbonyl]-2-pyridinyl]-2-(3-pyridinyl)benzamide

EXAMPLE 64

N-[5-(Dibenz[b,f][1,4]oxazepin-10(11H)-ylcarbonyl)-2-pyridinyl]-2-(2-pyridinyl)benzamide

EXAMPLE 65

N-[5-(Dibenz]b,f][1,4]oxazepin-10(11H)-ylcarbonyl2-pyridinyl]-2-(4-pyridinyl)benzamide

EXAMPLE 66

N-[5-(Pyrido[2,3-b][1,5]benzoxazepin-6(5H)-ylcarbonyl)-2-pyridinyl][1,1'biphenyl]-2-carboxamide A mixture of 0.198 g of 5,6-dihydropyrido[2,3-b][1,5]benzoxazepine, 0.155 g of N,N-diisopropylethylamine and 0.404 g of 6-[([1,1'-biphenyl]-2-carbonyl)amino]pyridine-3-carbonyl chloride in 12 ml of dichloromethane is stirred at room temperature for 3.5 hours. The mixture is poured into water and extracted with dichloromethane. The extract is washed with 2N $Na_2CO_3$, $H_2O$, brine and dried ($Na_2SO_4$). The solution is passed through a thin pad of hydrous magnesium silicate and the filtrate concentrated to dryness. The solid is dissolved hexane-ethyl acetate (1:2) and the solution filtered through a thin pad of hydrous magnesium silicate. The pad is washed with hexane-ethyl acetate (1:2) and the filtrate concentrated to dryness to give a glass, m.p.107° C.–114° C Anal. Found: C, 74.4; H, 5.7; N, 8.8

EXAMPLE 67

N-[4-(Pyrido[2,3-b][1,5]benzoxazepin-6(5H)-ylcarbonyl)-3-chlorophenyl][1,1'-biphenyl]-2-carboxamide A mixture of 0.198 g of 5,6-dihydropyrido[2,3-b][1,5]benzoxazepine, 0.155 g of N,N-diisopropylethylamine and 0.444 g of 4-[([1,1-biphenyl]-2-carbonyl)amino]-2-chlorobenzoyl chloride in 12 ml of dichloromethane is stirred at room temperature for 2.5 hours. The mixture is poured into water and extracted with dichloromethane. The extract is washed with 2N $Na_2CO_3$, $H_2O$, brine and dried ($Na_2SO_4$). The solution is passed through a thin pad of hydrous magnesium silicate. The filter pad is washed with 50 ml of hexane-ethyl acetate (1:2) and the filtrate concentrated to dryness.

The residue is triturated with ether to give a solid, m.p. 205°–217° C. Anal. Found: C, 72.3; H, 4.2; N, 7.9; Cl, 6.7.

As described for Example 66, the following compounds can be prepared.

EXAMPLE 68

N-[5-(Pyrido[2,3-b][1,5]benzoxazepin-6(5H)-ylcarbonyl)-3-pyridinyl][1,1'biphenyl]-2-carboxamide

EXAMPLE 69

N-[5-(Pyrido[2,3-b][1,5]benzoxazepin-6(5H)-ylcarbonyl)-2-pyridinyl]-2-chlorobenzamide

EXAMPLE 70

N-[5-(Pyrido[2,3-b][1,5]benzoxazepin-6(5H)-ylcarbonyl)-2-pyridinyl]-2-chloro-5-fluorobenzamide

EXAMPLE 71

N-[5-(Pyrido[2,3-b][1,5]benzoxazepin-6(5H)-ylcarbonyl)-2-pyridinyl]-2-hydroxybenzamide

EXAMPLE 72

N-[5-(Pyrido[2,3-b][1,5]benzoxazepin-6(5H)-ylcarbonyl)-2-pyridinyl]-2,5-difluorobenzamide

EXAMPLE 73

N-[5-(Pyrido[2,3-b][1,5]benzoxazepin-6(5H)-ylcarbonyl)-2-pyridinyl]-2-methylbenzamide

EXAMPLE 74

N-[5-(Pyrido[2,3-b][1,5]benzoxazepin-6(5H)-ylcarbonyl)-2-pyridinyl]-2-(dimethylamino)benzamide

EXAMPLE 75

N-[5-(Pyrido[2,3-b][1,5]benzoxazepin-6(5H)-ylcarbonyl)-2-pyridinyl]-2-(methylamino)benzamide

EXAMPLE 76

N-[5-(Pyrido[2,3-b][1,5]benzoxazepin-6(5H)-ylcarbonyl)-2-pyridinyl]-2-(aminomethyl)benzamide

EXAMPLE 77

N-[5-(Pyrido[2,3-b][1,5]benzoxazepin-6(5H)-ylcarbonyl)-2-pyridinyl]-2-methoxybenzamide

EXAMPLE 78

N-[5-(Pyrido[2,3-b][1,5]benzoxazepin-6(5H)-ylcarbonyl)-2-pyridinyl]-2-chloro-5-fluorobenzamide

EXAMPLE 79

N-[5-(Pyrido[2,3-b][1,5]benzoxazepin-6(5H)-ylcarbonyl)-2-pyridinyl]-2-methyl-3-fluorobenzamide

EXAMPLE 80

N-[5-(Pyrido[2,3-b][1,5]benzoxazepin-6(5H)-ylcarbonyl)-2-pyridinyl]-2-fluoro-6-chlorobenzamide

EXAMPLE 81

N-[5-(Pyrido[2,3-b][1,5]benzoxazepin-6(5H)-ylcarbonyl)-2-pyridinyl]-2,6-dichlorobenzamide

EXAMPLE 82

N-[5-(Pyrido[2,3-b][1,5]benzoxazepin-6(5H)-ylcarbonyl)-2-pyridinyl]-2,5-dimethylbenzamide

EXAMPLE 83

N-[5-(Pyrido[2,3-b][1,5]benzoxazepin-6(5H)-ylcarbonyl)-2-pyridinyl]-2-chloro-3-pyridinylcarboxamide

EXAMPLE 84

N-[5-(Pyrido[2,3-b][1,5]benzoxazepin-6(5H)-ylcarbonyl)-2-pyridinyl]-2-(methylamino)-3-pyridinylcarboxamide

EXAMPLE 85

N-[5-(Pyrido[2,3-b][1,5]benzoxazepin-6(5H)-ylcarbonyl)-2-pyridinyl]-2(dimethylamino)-3-pyridinylcarboxamide

EXAMPLE 86

N-[5-(Pyrido[2,3-b][1,5]benzoxazepin-6(5H)-ylcarbonyl)-2-pyridinyl]-2-(aminomethyl)4-pyridinylcarboxamide

EXAMPLE 87

N-[5-(Pyrido[2,3-b][1,5]benzoxazepin-6(5H)-ylcarbonyl)-2-pyridinyl]-2-(dimethylamino)-4-pyridinylcarboxamide As described for Example 67, the following compounds can be prepared.

EXAMPLE 88

N-[4-(Pyrido[2,3-b][1,5]benzoxazepin-6(5H)-ylcarbonyl)-3-chloro-6-methylphenyl][1,1'-biphenyl]-2-carboxamide

EXAMPLE 89

N-[4-(Pyrido[2,3-b][1,5]benzoxazepin-6(5H)-ylcarbonyl)-3,6-dimethylphenyl][1,1'-biphenyl]-2-carboxamide

EXAMPLE 90

N-[4-(Pyrido[2,3-b][1,5]benzoxazepin-6(5H)-ylcarbonyl)-2-methylphenyl][1,1'-biphenyl]-2-carboxamide

EXAMPLE 91

N-[4-(Pyrido[2,3-b][1,5]benzoxazepin-6(5H)-ylcarbonyl)-2-chlorophenyl][1,1'-biphenyl]-2-carboxamide

EXAMPLE 92

N-[4-(Pyrido[2,3-b][1,5]benzoxazepin-6(5H)-ylcarbonyl)-3-chloro-6-methylphenyl]-2-(2-thienyl)benzamide

EXAMPLE 93

N-[4-(Pyrido[2,3-b][1,5]benzoxazepin-6(5H)-ylcarbonyl)-3,6-dimethylphenyl]-2-(3-thienyl)benzamide

EXAMPLE 94

N-[4-(Pyrido[2,3-b][1,5]benzoxazepin-6(5H)-ylcarbonyl)-3-methylphenyl]-2-(2-thienyl)benzamide

EXAMPLE 95

N-[4-(Pyrido[2,3-b][1,5]benzoxazepin-6(5H)-ylcarbonyl)-3-chlorophenyl]-2-(2-thienyl)benzamide

EXAMPLE 96

N-[4-(Pyrido[2,3-b][1,5]benzoxazepin-6(5H)-ylcarbonyl)-3-chlorophenyl]-2-(3-thienyl)benzamide

EXAMPLE 97

N-[4-(Pyrido[2,3-b][1,5]benzoxazepin-6(5H)-ylcarbonyl)-3-chlorophenyl]-2-(2-furanyl)benzamide

EXAMPLE 98

N-[4-(Pyrido[2,3-b[1,5]benzoxazepin-6(5H)-ylcarbonyl)-3-chlorophenyl]-2-(2-pyridinyl)benzamide

EXAMPLE 99

N-[4-(Pyrido[2,3-b][1,5]benzoxazepin-6(5H)-ylcarbonyl)-3-chlorophenyl]-2-(3-pyridinyl)benzamide

EXAMPLE 100

N-[4-(Pyrido[2,3-b][1,5]benzoxazepin-6(5H)-ylcarbonyl)-3-chlorophenyl]-2-(4-pyridinyl)benzamide

EXAMPLE 101

N-[4-(Pyrido[2,3-b][1,5]benzoxazepin-6(5H)-ylcarbonyl)-3-chlorophenyl]-2-(3-furanyl)benzamide

EXAMPLE 102

N-[4-(Pyrido[2,3-b][1,5]benzoxazepin-6(5H)-ylcarbonyl)-3-methylphenyl][1,1'biphenyl]-2-carboxamide

EXAMPLE 103

N-[4-(Pyrido[2,3-b][1,5]benzoxazepin-6(5H)-ylcarbonyl)-3-methylphenyl]-2-(3-thienyl)benzamide

EXAMPLE 104

N-[4-(Pyrido[2,3-b][1,5]benzoxazepin-6-(5H)-ylcarbonyl)-3-methylphenyl]-2-(2-pyridinyl)benzamide

EXAMPLE 105

N-[4-(Pyrido[2,3-b][1,5]benzoxazepin-6-(5H)-ylcarbonyl)-3-methylphenyl]-2-(3-pyridinyl)benzamide

EXAMPLE 106

N-[4-(Pyrido[2,3-b][1,5]benzoxazepin-6(5H)-ylcarbonyl)-3-methylphenyl]-2-(4-pyridinyl)benzamide

EXAMPLE 107

N-[4-(Pyrido[2,3-b][1,5]benzoxazepin-6(5H)-ylcarbonyl)-3-methylphenyl]-2-(2-furanyl)benzamide

EXAMPLE 108

N-[4-(Pyrido[2,3-b][1,5]benzoxazepin-6(5H)-ylcarbonyl)-3,6-dimethylphenyl]-2-(2-thienyl)benzamide As described for Example 67, the following compounds can be prepared.

EXAMPLE 109

N-[4-(Pyrido[2,3-b][1,5]benzoxazepin-6(5H)-ylcarbonyl)-3-fluoro-6-methylphenyl][1,1-biphenyl]-2-carboxamide

EXAMPLE 110

N-[4-(Pyrido[2,3-b][1,5]benzoxazepine-6(5H)-ylcarbonyl)-3,6-dichlorophenyl][1,1'-biphenyl]-2-carboxamide

EXAMPLE 111

N-[4-(Pyrido[2,3-b][1,5]benzoxazepin-6(5H)-ylcarbonyl)-3-fluorophenyl][1,1'-biphenyl]-2-carboxamide

EXAMPLE 112

N-[4-(Pyrido[2,3-b][1,5]benzoxazepin-6(5H)-ylcarbonyl)-phenyl][1,1'-biphenyl]-2-carboxamide

EXAMPLE 113

N-[4-(Pyrido[2,3-b][1,5]benzoxazepin-6(5H)-ylcarbonyl)-phenyl]-2-(2-thienyl)benzamide

EXAMPLE 114

N-[4-(Pyrido[2,3-b][1,5]benzoxazepin-6(5H)-ylcarbonyl)-phenyl]-2-(3-thienyl)benzamide

EXAMPLE 115

N-[4-(Pyrido[2,3-b][1,5]benzoxazepin-6(5H)-ylcarbonyl)-phenyl]-2-(2-thienyl)benzamide

EXAMPLE 116

N-[4-(Pyrido[2,3-b][1,5]benzoxazepin-6(5H)-ylcarbonyl)-3-fluorophenyl]-2-(2-thienyl)benzamide

EXAMPLE 117

N-[4-(Pyrido[2,3-b][1,5]benzoxazepin-6(5H)-ylcarbonyl)-phenyl]-2-(3-thienyl) benzamide

EXAMPLE 118

N-[4-(Pyrido[2,3-b][1,5]benzoxazepin-6(5H)-ylcarbonyl)-phenyl]-2-(2-furanyl)benzamide

EXAMPLE 119

N-[4-(Pyrido[2,3-b][1,5]benzoxazepin-6(5H)-ylcarbonyl)-phenyl]-2-(2-pyridinyl)benzamide

EXAMPLE 120

N-[4-(Pyrido[2,3-b][1,5]benzoxazepin-6(5H)-ylcarbonyl)-phenyl]-2-(3-pyridinyl)benzamide

EXAMPLE 121

N-[4-(Pyrido[2,3-b][1,5]benzoxazepin-6(5H)-ylcarbonyl)-phenyl]-2-(4-pyridinyl)benzamide

EXAMPLE 122

N-[4-(Pyrido[2,3-b][1,5]benzoxazepin-6(5H)-ylcarbonyl)-3-fluorophenyl]-2-(3-furanyl)benzamide

EXAMPLE 123

N-[4-(Pyrido[2,3-b][1,5]benzoxazepin-6(5H)-ylcarbonyl)-3-methyl-6-fluorophenyl][1,1'-biphenyl]-2-carboxamide

EXAMPLE 124

N-[4-(Pyrido[2,3-b][1,5]benzoxazepin-6(5H)-ylcarbonyl)-2-methylphenyl]-2-(2-furanyl)benzamide

EXAMPLE 125

N-[4-(Pyrido[2,3-b][1,5]benzoxazepin-6(5H)-ylcarbonyl)-3-methylphenyl]-2-(3-furanyl)benzamide

EXAMPLE 126

N-[4-(Pyrido[2,3-b][1,5]benzoxazepin-6(5H)-ylcarbonyl)-3,6-dimethylphenyl]-2-(3-pyridinyl)benzamide

EXAMPLE 127

N-[4-(Pyrido[2,3-b][1,5]benzoxazepin-6(5H)-ylcarbonyl)-3,6-dichlorophenyl]-2-(4-pyridinyl)benzamide

EXAMPLE 128

N-[4-(Pyrido[2,3-b][1,5]benzoxazepin-6(5H)-ylcarbonyl)-phenyl]-2-(3-furanyl)benzamide

EXAMPLE 129

N-[4-(Pyrido[2,3-b][1,5]benzoxazepin-6(5H)-ylcarbonyl)-3-fluorophenyl]-2-(2-thienyl)benzamide

EXAMPLE 130

N-[5-(Pyrido[2,3-b][1,4]benzoxazepin-5(6H)-ylcarbonyl)-2-pyridinyl]-5-fluoro-2-methylbenzamide As described for Example 46, the reaction of 5,6-dihydropyrido[2,3-b][1,4]benzoxazepine (1 mmol) with 2-[(2-methyl-5-fluorobenzoyl)amino]-5-pyridinylcarbonyl chloride (1.0 mmol) in dichloromethane in the presence of N,N-diisopropylethylamine (3 mmol) gives the product as a glass.

EXAMPLE 131

N-[5-(Pyrido[2,3-b][1,4]benzoxazepin-5(6H)-ylcarbonyl)-2-pyridinyl][1,1'-biphenyl]-2-carboxamide As described for Example 66, the reaction of 5,6-dihydropyrido[2,3-b][1,4]benzoxazepine (0.198 g) with 6-

[([1,1'-biphenyl]-2-carbonyl)amino]pyridine-3-carbonyl chloride (0.404 g) in dichloromethane in the presence of N,N-diisopropylethylamine (0.155 g) gives the product as a solid.

EXAMPLE 132

N-[4-(Pyrido[2,3-b][1,4]benzoxazepin-5(6H)-ylcarbonyl)-3-chlorophenyl][1,1'biphenyl]-2-carboxamide As described for Example 66, reaction of 0.198 g of 5,6-dihydropyrido[2,3-b][1,4]benzoxazepine with 0.444 g of 4-[([1,1'-biphenyl]-2-carbonyl)amino]-2-chlorobenzoyl chloride in dichloromethane in the presence of N,N-diisopropylethylamine gives the product as a solid.

EXAMPLE 133

N-[4-(6,11-Dihydropyrido[2,3-b][1,5]benzodiazepin-6(5H)-ylcarbonyl)-phenyl][1.1'-biphenyl]-2-carboxamide To a mixture of 10.55 g of 6,11-dihydropyrido[2,3-b][1,5]benzodiazepin-5(6H)-one in 40 ml of tetrahydrofuran is added 15 ml of 10 molar borane-dimethylsulfide in tetrahydrofuran. The mixture is stirred at room temperature 2 hours and then refluxed (under argon) for 4 hours. An additional 40 ml of tetrahydrofuran is added and the mixture refluxed overnight. To the cooled mixture is added 12 ml of methanol and the solvent removed. To the residue is added 30 ml of 2NNaOH and the solution refluxed 2 hours under argon. The mixture is extracted with ethyl acetate and the extract washed with 2N citric acid. The aqueous layer is made basic with 2N NaOH and extracted with ethyl acetate. The extract is washed with $H_2O$, brine and dried ($Na_2SO_4$). The solution is filtered through a thin layer of hydrous magnesium silicate and the filtrate concentrated to dryness to give 4.65 g of brown solid. The solid is purified by chromatography on silica gel to give the product as a solid. A 4.85 g sample of crude product is triturated with ether to give 2.68 g of 6,11-dihydropyrido[2,3-b][1,5]benzodiazepine as a solid.

A mixture of 0.296 g of 6,11-dihydropyrido[2,3-b][1,5]benzodiazepine, 0.604 g of 4-[([1,1'-biphenyl]-2-carbonyl)amino]benzoyl chloride and 0.232 g of N,N-diisopropylethylamine in 6 ml of dichloromethane is stirred at room temperature for 1.5 hours. The mixture is poured into water and extracted with dichloromethane. The extract is washed with $H_2O$, saturated $NaHCO_3$, $H_2O$, brine and dried ($Na_2SO_4$). The solution is filtered through a thin pad of hydrous magnesium silicate and the filtrate concentrated to dryness. The residue is purified on thick layer silica gel plates with hexane-ethyl acetate (1:2) as solvent to give the product as a solid which is crystallized from ethyl acetate to give off-white crystals, m.p. 220° C.–221° C.

EXAMPLE 134

N-[4-(6,11-Dihydropyrido[2,3-b][1,5]benzodiazepin-6(5H)-ylcarbonyl)-3-chlorophenyl][1,1'-biphenyl]-2-carboxamide A mixture of 0.197 g of 6,11-dihydropyrido[2,3-b][1,5]benzodiazepine, 0.444 g of 4-[([1,1'-biphenyl]-2-carbonyl)amino]-2-chlorobenzoyl chloride and 0.155 g of N,N-diisopropylethylamine in 8 ml of dichloromethane is stirred at room temperature for 1.5 hours. The mixture is poured into water and extracted with dichloromethane. The extract is washed with $H_2O$, saturated $NaHCO_3$, $H_2O$, brine and dried ($Na_2SO_4$). The solution is filtered through a thin pad of hydrous magnesium silicate and the filtrate concentrated to dryness. The residue is chromatographed on thick layer silica gel plates with hexane-ethyl acetate (1:2) to give 0.160 g of solid, m.p. 147° C.–165° C. Anal Found: C, 72.1; H, 5.1; N, 9.1; Cl, 6.3.

EXAMPLE 135

N-[4-(6,11-Dihydropyrido[2,3-b][1,5]benzodiazepin-6(5H)-ylcarbonyl)-phenyl][1,1'-biphenyl]-2-carboxamide, hydrochloride Hydrogen chloride (gas) is bubbled into 50 ml of anhydrous chilled methanol for 15 minutes. A 25 ml sample of the methanolic hydrogen chloride is added to 0.30 g of N-[4-(6,11-dihydropyrido[2,3-b][1,5]benzodiazepin-6(5H)-ylcarbonyl)phenyl][1,1'-biphenyl]-2-carboxamide. The mixture is stirred at 0° C. for 0.5 hours and allowed to warm to room temperature. The solvent is removed and the solid dried under vacuum to give 0.31 g of solid, m.p. 195° C.–210° C.

As described for Example 134, the following compounds can be prepared by reaction of 6,11-dihydropyrido[2,3-b][1,5]benzodiazepine with the appropriate substituted or unsubstituted [(arylcarbonyl)amino]benzoyl chloride or the appropriate substituted or unsubstituted[(arylcarbonyl)-amino]pyridinylcarbonyl chloride.

EXAMPLE 136

N-[4-(6,11-Dihydropyrido[2,3-b][1,5]benzodiazepin-6(5H)-ylcarbonyl)-3-chlorophenyl]-2-(2-thienyl)benzamide

EXAMPLE 137

N-[4-(6,11-Dihydropyrido[2,3-b][1,5]benzodiazepin-6(5H)-ylcarbonyl)-3-chlorophenyl]-2-(3-thienyl)benzamide

EXAMPLE 138

N-[4-(6,11-Dihydropyrido[2,3-b][1,5]benzodiazepin-6(5H)-ylcarbonyl)-3-chloro-6-methylphenyl]-2-(2-thienyl)benzamide

EXAMPLE 139

N-[4-(6,11-Dihydropyrido[2,3-b][1,5]benzodiazepin-6(5H)-ylcarbonyl)-phenyl]-2-(2-thienyl)benzamide

EXAMPLE 140

N-[4-(6,11-Dihydropyrido[2,3-b][1,5]benzodiazepin-6(5H)-ylcarbonyl)-phenyl]-2-(3-thienyl)benzamide

EXAMPLE 141

N-[4-(6,11-Dihydropyrido[2,3-b][1,5]benzodiazepin-6(5H)-ylcarbonyl)-3-methylphenyl]-2-(2-thienyl)benzamide

EXAMPLE 142

N-[4-(6,11-Dihydropyrido[2,3-b][1,5]benzodiazepin-6(5H)-ylcarbonyl)-3,6-dimethylphenyl]-2-(2-thienyl)benzamide

EXAMPLE 143

N-[4-(6,11-Dihydropyrido[2,3-b][1,5]benzodiazepin-6(5H)-ylcarbonyl)-3-methylphenyl][1,1'-biphenyl]-2-carboxamide

EXAMPLE 144

N-[4-(6,11-Dihydropyrido[2,3-b][1,5]benzodiazepin-6(5H)-ylcarbonyl)-3,6-dimethylphenyl][1,1'-biphenyl]-2-carboxamide

EXAMPLE 145

N-[4-(6,11-Dihydropyrido[2,3-b][1,5]benzodiazepin-6(5H)-ylcarbonyl)-3,6-dichlorophenyl][1,1'biphenyl]-2-carboxamide

EXAMPLE 146

N-[4-(6,11-Dihydropyrido[2,3-b][1,5]benzodiazepin-6(5H)-ylcarbonyl)-3-methyl-6-chlorophenyl][1,1'-biphenyl]-2-carboxamide

EXAMPLE 147

N-[4-(6,11-Dihydropyrido[2,3-b][1,5]benzodiazepin-6(5H)-ylcarbonyl)-3-chloro-6-fluorophenyl][1,1'-biphenyl]-2-carboxamide

EXAMPLE 148

N-[4-(6,11-Dihydropyrido[2,3-b][1,5]benzodiazepin-6(5H)-ylcarbonyl)-2-methylphenyl][1,1'-biphenyl]-2-carboxamide

EXAMPLE 149

N-[4-(6,11-Dihydropyrido[2,3-b][1,5]benzodiazepin-6(5H)-ylcarbonyl)-2-chlorophenyl][1,1'-biphenyl]-2-carboxamide

EXAMPLE 150

N-[4-(6,11-Dihydropyrido[2,3-b][1,5]benzodiazepin-6(5H)-ylcarbonyl)-phenyl]-2-(2-pyridinyl)benzamide

EXAMPLE 151

N-[4-(6,11-Dihydropyrido[2,3-b][1,5]benzodiazepin-6(5H)-ylcarbonyl)-phenyl]-2-(3-pyridinyl)benzamide

EXAMPLE 152

N-[4-(6,11-Dihydropyrido[2,3-b][1,5]benzodiazepin-6(5H)-ylcarbonyl)-phenyl]-2-(4-pyridinyl)benzamide

EXAMPLE 153

N-[4-(6,11-Dihydropyrido[2,3-b][1,5]benzodiazepin-6(5H)-ylcarbonyl)-3-chlorophenyl]-2-(2-pyridinyl)benzamide

EXAMPLE 154

N-[4-(6,11-Dihydropyrido[2,3-b][1,5]benzodiazepin-6(5H)-ylcarbonyl)-3-chlorophenyl]-2-(3-pyridinyl)benzamide

EXAMPLE 155

N-[4-(6,11-Dihydropyrido[2,3-b][1,5]benzodiazepin-6(5H)-ylcarbonyl)-3-chlorophenyl]-2-(4-pyridinyl)benzamide

EXAMPLE 156

N-[4-(6,11-Dihydropyrido[2,3-b][1,5]benzodiazepin-6(5H)-ylcarbonyl)-3-methylphenyl]-2-(2-pyridinyl)benzamide

EXAMPLE 157

N-[4-(6,11-Dihydropyrido[2,3-b][1,5]benzodiazepin-6(5H)-ylcarbonyl)-3-methylphenyl]-2-(3-pyridinyl)benzamide

EXAMPLE 158

N-[4-(6,11-Dihydropyrido[2,3-b][1,5]benzodiazepin-6(5H)-ylcarbonyl)-3-methylphenyl]-2-(4-pyridinyl)benzamide

EXAMPLE 159

N-[4-(6,11-Dihydropyrido[2,3-b][1,5]benzodiazepin-6(5H)-ylcarbonyl)-3-methyl-6-fluorophenyl]-2-(2-thienyl)benzamide

EXAMPLE 160

N-[4-(6,11-Dihydropyrido[2,3-b][1,5]benzodiazepin-6(5H)-ylcarbonyl)-3,6-dimethylphenyl]-2-(2-pyridinyl)benzamide

EXAMPLE 161

N-[4-(6,11-Dihydropyrido[2,3-b][1,5]benzodiazepin-6(5H)-ylcarbonyl)-3,6-dimethylphenyl]-2-(3-pyridinyl)benzamide

EXAMPLE 162

N-[4-(6,11-Dihydropyrido[2,3-b][1,5]benzodiazepin-6(5H)-ylcarbonyl)-3,6-dimethylphenyl]-2-(4-pyridinyl)benzamide

EXAMPLE 163

N-[4-(6,11-Dihydropyrido[2,3-b][1,5]benzodiazepin-6(5H)-ylcarbonyl)-phenyl]-2-methoxypyridine-3-carboxamide

EXAMPLE 164

N-[4-(6,11-Dihydropyrido[2,3-b][1,5]benzodiazepin-6(5H)-ylcarbonyl)-3-chlorophenyl]-2-methylthiopyridine-3-carboxamide

EXAMPLE 165

N-[4-(6,11-Dihydropyrido[2,3-b][1,5]benzodiazepin-6(5H)-ylcarbonyl)-3-methylphenyl]-2-methylpyridine-3-carboxamide

EXAMPLE 166

N-[4-(6,11-Dihydropyrido[2,3-b][1,5]benzodiazepin-6(5H)-ylcarbonyl)-3,6-dimethylphenyl]-2-methylpyridine-3-carboxamide

EXAMPLE 167

N-[4-(6,11-Dihydropyrido[2,3-b][1,5]benzodiazepin-6(5H)-ylcarbonyl)-phenyl]-2-methylpyridine-3-carboxamide

EXAMPLE 168

N-[4-(6,11-Dihydropyrido[2,3-b][1,5]benzodiazepin-6(5H)-ylcarbonyl)-3-chlorophenyl]-2-methylpyridine-3-carboxamide

EXAMPLE 169

N-[4-(6,11-Dihydropyrido[2,3-b][1,5]benzodiazepin-6(5H)-ylcarbonyl)-3-chloro-6-methylphenyl]-2-fluoropyridine-3-carboxamide

EXAMPLE 170

N-[4-(6,11-Dihydropyrido[2,3-b][1,5]benzodiazepin-6(5H)-ylcarbonyl)-3-chlorophenyl]-2-fluoropyridine-3-carboxamide

EXAMPLE 171

N-[4-(6,11-Dihydropyrido[2,3-b][1,5]benzodiazepin-6(5H)-ylcarbonyl)-3-methylphenyl]-2-chloropyridine-3-carboxamide

EXAMPLE 172

N-[4-(6,11-Dihydropyrido[2,3-b][1,5]benzodiazepin-6(5H)-ylcarbonyl)-3,6-dimethylphenyl]-2-chloropyridine-3-carboxamide

EXAMPLE 173

N-[4-(6,11-Dihydropyrido[2,3-b][1,5]benzodiazepin-6(5H)-ylcarbonyl)-phenyl]-3-methylpyridine-2-carboxamide

EXAMPLE 174

N-[4-(6,11-Dihydropyrido[2,3-b][1,5]benzodiazepin-6(5H)-ylcarbonyl)-3-chlorophenyl]-3-methylpyridine-2-carboxamide

EXAMPLE 175

N-[4-(6,11-Dihydropyrido[2,3-b][1,5]benzodiazepin-6(5H)-ylcarbonyl)-3-chlorophenyl]-2-chloropyridine-3-carboxamide

EXAMPLE 176

N-[5-(6,11-Dihydropyrido[2,3-b][1,5]benzodiazepin-6(5H)-ylcarbonyl)-2-pyridinyl][1,1'-biphenyl]-2-carboxamide, m.p. 278° C.–281° C.

EXAMPLE 177

N-[5-(6,11-Dihydropyrido[2,3-b][1,5]benzodiazepin-6(5H)-ylcarbonyl)-2-pyridinyl]-2-(2-thienyl)benzamide

EXAMPLE 178

N-[5-(6,11-Dihydropyrido[2,3-b][1,5]benzodiazepin-6(5H)-ylcarbonyl)-2-pyridinyl]-2-(3-thienyl)benzamide

EXAMPLE 179

N-[5-(6,11-Dihydropyrido[2,3-b][1,5]benzodiazepin-6(5H)-ylcarbonyl)-2-pyridinyl]-2-fluorobenzamide

EXAMPLE 180

N-[5-(6,11-Dihydropyrido[2,3-b][1,5]benzodiazepin-6(5H)-ylcarbonyl)-2-pyridinyl]-2-(2-pyridinyl)benzamide

EXAMPLE 181

N-[5-(6,11-Dihydropyrido[2,3-b][1,5]benzodiazepin-6(5H)-ylcarbonyl)-2-pyridinyl]-2(3-pyridinyl)benzamide

EXAMPLE 182

N-[5-(6,11-Dihydropyrido[2,3-b][1,5]benzodiazepin-6(5H)-ylcarbonyl)-2-pyridinyl]-2-(4-pyridinyl)benzamide

EXAMPLE 183

N-[5-(6,11-Dihydropyrido[2,3-b][1,5]benzodiazepin-6(5H)-ylcarbonyl)-2-pyridinyl]-2-(2-furanyl)benzamide

EXAMPLE 184

N-[5-(6,11-Dihydropyrido[2,3-b][1,5]benzodiazepin-6(5H)-ylcarbonyl)-2-pyridinyl]-2-(3-furanyl)benzamide

EXAMPLE 185

N-[5-(6,11-Dihydropyrido[2,3-b][1,5]benzodiazepin-6(5H)-ylcarbonyl)-2-pyridinyl]-3-chloropyridine-2-carboxamide

EXAMPLE 186

N-[5-(6,11-Dihydropyrido[2,3-b][1,5]benzodiazepin-6(5H)-ylcarbonyl)-2-pyridinyl]-2-methylpyridine-3-carboxamide

EXAMPLE 187

N-[5-(6,11-Dihydropyrido[2,3-b][1,5]benzodiazepin-6(5H)-ylcarbonyl)-2-pyridinyl]-5-fluoro-2-methylbenzamide

EXAMPLE 188

N-[5-(6,11-Dihydropyrido[2,3-b][1,5]benzodiazepin-6(5H)-ylcarbonyl)-2-pyridinyl]-2-chlorobenzamide

EXAMPLE 189

N-[5-(6,11-Dihydropyrido[2,3-b][1,5]benzodiazepin-6(5H)-ylcarbonyl)-2-pyridinyl]-2-chloro-5-fluorobenzamide

EXAMPLE 190

N-[5-(6,11-Dihydropyrido[2,3-b][1,5]benzodiazepin-6(5H)-ylcarbonyl)-2-pyridinyl]-2-methylbenzamide

EXAMPLE 191

N-[5-(6,11-Dihydropyrido[2,3-b][1,5]benzodiazepin-6(5H)-ylcarbonyl)-2-pyridinyl]-2,5-dimethylbenzamide

EXAMPLE 192

N-[5-(6,11-Dihydropyrido[2,3-b][1,5]benzodiazepin-6(5H)-ylcarbonyl)-2-pyridinyl]-2-chloro-4-fluorobenzamide

EXAMPLE 193

N-[5-(6,11-Dihydropyrido[2,3-b][1,5]benzodiazepin-6(5H)-ylcarbonyl)-2-pyridinyl]-2-chloro-6-fluorobenzamide

EXAMPLE 194

N-[5-(6,11-Dihydropyrido[2,3-b][1,5]benzodiazepin-6(5H)-ylcarbonyl)-2-pyridinyl]-2-methyl-3-fluorobenzamide

EXAMPLE 195

N-[5-(6,11-Dihydropyrido[2,3-b][1,5]benzodiazepin-6(5H)-ylcarbonyl)-2-pyridinyl]-2-hydroxybenzamide

EXAMPLE 196

N-[5-(6,11-Dihydropyrido[2,3-b][1,5]benzodiazepin-6(5H)-ylcarbonyl)-2-pyridinyl]-2-acetyloxybenzamide

EXAMPLE 197

N-[5-(6,11-Dihydropyrido[2,3-b][1,5]benzodiazepin-6(5H)-ylcarbonyl)-2-pyridinyl]-2-aminobenzamide

EXAMPLE 198

N-[5-(6,11-Dihydropyrido[2,3-b][1,5]benzodiazepin-6(5H)-ylcarbonyl)-2-pyridinyl]-2-(methylamino)benzamide

EXAMPLE 199

N-[5-(6,11-Dihydropyrido[2,3-b][1,5]benzodiazepin-6(5H)-ylcarbonyl)-2-pyridinyl]-2-(dimethylamino)benzamide

EXAMPLE 200

N-[5-(6,11-Dihydropyrido[2,3-b][1,5]benzodiazepin-6(5H)-ylcarbonyl)-2pyridinyl]-2-aminomethylbenzamide

EXAMPLE 201

N-[5-(6,11-Dihydropyrido[2,3-b][1,5]benzodiazepin-6(5H)-ylcarbonyl)-2-pyridinyl]-2-(diethylamino)benzamide

EXAMPLE 202

N-[5-(6,11-Dihydropyrido[2,3-b][1,5]benzodiazepin-6(5H)-ylcarbonyl)-2-pyridinyl]-2-(dimethylaminomethyl)benzamide

EXAMPLE 203

N-[5-(6,11-Dihydropyrido[2,3-b][1,5]benzodiazepin-6(5H)-ylcarbonyl)-2-pyridinyl]-2-(methylthio)benzamide

EXAMPLE 204

N-[5-(6,11-Dihydropyrido[2,3-b][1,5]benzodiazepin-6(5H)-ylcarbonyl)-2-pyridinyl]-2-chloropyridine-3-carboxamide

EXAMPLE 205

N-[5-(6,11-Dihydropyrido[2,3-b][1,5]benzodiazepin-6(5H)-ylcarbonyl)-2-pyridinyl]-2-fluoropyridine-3-carboxamide

EXAMPLE 206

N-[5-(6,11-Dihydropyrido[2,3-b][1,5]benzodiazepin-6(5H)-ylcarbonyl)-2-pyridinyl]-2-methoxypyridine-3-carboxamide

EXAMPLE 207

N-[5-(6,11-Dihydropyrido[2,3-b][1,5]benzodiazepin-6(5H)-ylcarbonyl)-2-pyridinyl]-2-methylthiopyridine-3-carboxamide

EXAMPLE 208

N-[5-(6,11-Dihydropyrido[2,3-b][1,5]benzodiazepin-6(5H)-ylcarbonyl)-2-pyridinyl]-2-aminopyridine-3-carboxamide

EXAMPLE 209

N-[5-(6,11-Dihydropyrido[2,3-b][1,5]benzodiazepin-6(5H)-ylcarbonyl)-2pyridinyl]-2-methylaminopyridine-3-carboxamide

EXAMPLE 210

N-[5-(6,11-Dihydropyrido[2,3-b][1,5]benzodiazepin-6(5H)-ylcarbonyl)-2-pyridinyl]-2-(dimethylamino)pyridine-3-carboxamide

EXAMPLE 211

N-[5-(6,11-Dihydropyrido[2,3-b][1,5]benzodiazepin-6(5H)-ylcarbonyl)-2-pyridinyl]thiophene-2-carboxamide

EXAMPLE 212

N-[5-(6,11-Dihydropyrido[2,3-b][1,5]benzodiazepin-6(5H)-ylcarbonyl)-2-pyridinyl]thiophene-3-carboxamide

EXAMPLE 213

N-[5-(6,11-Dihydropyrido[2,3-b][1,5]benzodiazepin-6(5H)-ylcarbonyl)-2-pyridinyl]furane-2-carboxamide

EXAMPLE 214

N-[5-(6,11-Dihydropyrido[2,3-b][1,5]benzodiazepin-6(5H)-ylcarbonyl)-2-pyridinyl]-2-methylthiophene-3-carboxamide

EXAMPLE 215

N-[5-(6,11-Dihydropyrido[2,3-b][1,5]benzodiazepin-6(5H)-ylcarbonyl)-2-pyridinyl]-3-methylthiophene-2-carboxamide

EXAMPLE 216

N-[5-(6,11-Dihydropyrido[2,3-b][1,5]benzodiazepin-6(5H)-ylcarbonyl)-2-pyridinyl]-2-chlorothiophene-3-carboxamide

EXAMPLE 217

N-[5-(6,11-Dihydropyrido[2,3-b][1,5]benzodiazepin-6(5H)-ylcarbonyl-2-pyridinyl]-2-methylthiophene-3-carboxamide

EXAMPLE 218

N-[4-[(5,11-Dihydro-10H-dibenz[b,e][1,4]diazepin-10-yl)carbonyl]-3-chlorophenyl][1,1'-biphenyl]-2-carboxamide A mixture of 0.196 g of 5,11-dihydro-10H-dibenzo[b,e][1,4]diazepine, 0.155 g of N,N-diisopropylethylamine and 0.444 g of 4-[([1,1'-biphenyl]-2-carbonyl)amino]-2-chlorobenzoyl chloride in 12 ml of dichloromethane is stirred at room temperature overnight. The mixture is poured into water and extracted with dichloromethane. The extract is washed with 2N $K_2CO_3$, $H_2O$, brine and dried ($Na_2SO_4$). The solution is filtered through a thin pad of hydrous magnesium silicate. The filtrate is concentrated to dryness and the residue triturated with ether and the solvent removed. The residue is triturated with dichloromethane to give 0.31 g of solid, m.p. 158° C.–184° C. Anal. Found for $C_{33}H_{24}ClN_3O_2$ ½ $H_2O$; C,73.7; H, 4.6; N,7.5; Cl,6.9.

As described for Example 218, the following compounds can be prepared by the reaction of 5,11-dihydro-10H-dibenz[b,e][1,4]diazepine with the appropriate substituted or unsubstituted [arylcarbonyl)amino]benzoyl chloride or the appropriate substituted or unsubstituted [(arylcarbonyl)amino]pyridinylcarbonyl chloride.

EXAMPLE 219

N-[4-[(5,11-Dihydro-10H-dibenz[b,e][1,4]diazepin-10-yl)carbonyl]-phenyl][1,1'-biphenyl]-2-carboxamide

EXAMPLE 220

N-[4-[(5,11-Dihydro-10H-dibenz[b,e][1,4]diazepin-10-yl)carbonyl]-3-methylphenyl][1,1'-biphenyl-2-carboxamide

EXAMPLE 221

N-[4-[(5,11-Dihydro-10H-dibenz[b,e][1,4]diazepin-10-yl)carbonyl]-3,6-dimethylphenyl][1,1'-biphenyl]-2-carboxamide

EXAMPLE 222

N-[4-[(5,11-Dihydro-10H-dibenz[b,e][1,4]diazepin-10-yl)carbonyl]-3-chlorophenyl]-2-(2-thienyl)benzamide

EXAMPLE 223

N-[4-[(5,11-Dihydro-10H-dibenz[b,e][1,4]diazepin-10-yl)carbonyl -3-chlorophenyl]-2-(3-thienyl)benzamide

EXAMPLE 224

N-[4-[(5,11-Dihydro-10H-dibenz[b,e][1,4]diazepin-10-yl)carbonyl]-3-chlorophenyl]-2-(3-furanyl)benzamide

EXAMPLE 225

N-[4-[(5,11-Dihydro-10H-dibenz[b,e][1,4]diazepin-10-yl)carbonyl]-3-chlorophenyl]-2-(2-furanyl)benzamide

EXAMPLE 226

N-[4-[(5,11-Dihydro-10H-dibenz[b,e][1,4]diazepin-10-yl)carbonyl]-3-methylphenyl]-2-(2-thienyl)benzamide

EXAMPLE 227

N-[4-[(5,11-Dihydro-10H-dibenz[b,e][1,4]diazepin-10-yl)carbonyl]-3-methylphenyl]-2-(3-thienyl)benzamide

EXAMPLE 228

N-[4-[(5,11-Dihydro-10H-dibenz[b,e][1,4]diazepin-10-yl)carbonyl]-3-methylphenyl][1,1'biphenyl]-2-carboxamide

EXAMPLE 229

N-[4-[(5,11-Dihydro-10H-dibenz[b,e][1,4]diazepin-10-yl)carbonyl]-3,6-dimethylphenyl][1,1'-biphenyl-2-carboxamide

EXAMPLE 230

N-[4-[(5,11-Dihydro-10H-dibenz[b,e][1,4]diazepin-10-yl)carbonyl]-3-methyl-6-chlorophenyl][1,1'-biphenyl]-2-carboxamide

EXAMPLE 231

N-[4-[(5,11-Dihydro-10H-dibenz[b,e][1,4]diazepin-10-yl)carbonyl]-3-chloro-6-fluorophenyl][1,1'-biphenyl]-2-carboxamide

EXAMPLE 232

N-[4-[(5,11-Dihydro-10H-dibenz[b,e][1,4]diazepin-10-yl)carbonyl]-2-methylphenyl][1,1'-biphenyl]-2-carboxamide

EXAMPLE 233

N-[4-[(5,11-Dihydro-10H-dibenz[b,e][1,4]diazepin-10-yl)carbonyl]-3-chloro-6-methylphenyl][1,1'-biphenyl]-2-carboxamide

EXAMPLE 234

N-[4-[(5,11-Dihydro-10H-dibenz[b,e][1,4]diazepin-10-yl)carbonyl]-2-chlorophenyl][1,1'-biphenyl]-2-carboxamide

EXAMPLE 235

N-[4-[(5,11-Dihydro-10H-dibenz[b,e][1,4]diazepin-10-yl)carbonyl]-phenyl]-2-(2-pyridinyl)benzamide

EXAMPLE 236

N-[4-[(5,11-Dihydro-10H-dibenz[b,e][1,4]diazepin-10-yl)carbonyl]-phenyl]-2-(3-pyridinyl)benzamide

EXAMPLE 237

N-[4-[(5,11-Dihydro-10H-dibenz[b,e][1,4]diazepin-10-yl)carbonyl]-phenyl]-2-(4-pyridinyl)benzamide

EXAMPLE 238

N-[4-[(5,11-Dihydro-10H-dibenz[b,e][1,4]diazepin-10-yl)carbonyl]-3-chlorophenyl]-2-(2-pyridinyl)benzamide

EXAMPLE 239

N-[4-[(5,11-Dihydro-10H-dibenz[b,e][1,4]diazepin-10-yl)carbonyl]-3-chlorophenyl]-2-(3-pyridinyl)benzamide

EXAMPLE 240

N-[4-[(5,11-Dihydro-10H-dibenz[b,e][1,4]diazepin-10-yl)carbonyl]-3-chlorophenyl]-2-(4-pyridinyl)benzamide

EXAMPLE 241

N-[4-[(5,11-Dihydro-10H-dibenz[b,e][1,4]diazepin-10-yl)carbonyl]-3-methylphenyl]-2-(2-pyridinyl)benzamide

EXAMPLE 242

N-[4-[(5,11-Dihydro-10H-dibenz[b,e][1,4]diazepin-10-yl)carbonyl]-3-methylphenyl]-2-(3-pyridinyl)benzamide

EXAMPLE 243

N-[4-[(5,11-Dihydro-10H-dibenz[b,e][1,4]diazepin-10-yl)carbonyl]-3-methylphenyl]-2-(4-pyridinyl)benzamide

EXAMPLE 244

N-[4-[(5,11-Dihydro-10H-dibenz[b,e][1,4]diazepin-10-yl)carbonyl]-3,6-dimethylphenyl]-2-(2-pyridinyl)benzamide

EXAMPLE 245

N-[4-[(5,11-Dihydro-10H-dibenz[b,e][1,4]diazepin-10-yl)carbonyl]-3,6-dimethylphenyl]-2-(3-pyridinyl)benzamide

EXAMPLE 246

N-[4-[(5,11-Dihydro-10H-dibenz[b,e][1,4]diazepin-10-yl)carbonyl]-3,6-dimethylphenyl]-2-(4-pyridinyl)benzamide

EXAMPLE 247

N-[4-[(5,11-Dihydro-10H-dibenz[b,e][1,4]diazepin-10-yl)carbonyl]phenyl]-2-phenylmethyl)benzamide

EXAMPLE 248

N-[4-[(5,11-Dihydro-10H-dibenz[b,e][1,4]diazepin-10-yl)carbonyl]phenyl]-2-(3-chlorophenylmethyl)benzamide

EXAMPLE 249

N-[4-[(5,11-Dihydro-10H-dibenz[b,e][1,4]diazepin-10-yl)carbonyl]-3-chlorophenyl]-2-(phenylmethyl)benzamide

EXAMPLE 250

N-[4-[(5,11-Dihydro-10H-dibenz[b,e][1,4]diazepin-10-yl)carbonyl]-3-chlorophenyl]-2-methoxypyridine-3-carboxamide

EXAMPLE 251

N-[4-[(5,11-Dihydro-10H-dibenz[b,e][1,4]diazepin-10-yl)carbonyl]-3-chlorophenyl]-2-(methylthio)pyridine-3-carboxamide

EXAMPLE 252

N-[4-[(5,11-Dihydro-10H-dibenz[b,e][1,4]diazepin-10-yl)carbonyl]-3-methylphenyl]-2-methylpyridine-3-carboxamide

EXAMPLE 253

N-[4-[(5,11-Dihydro-10H-dibenz[b,e][1,4]diazepin-10-yl)carbonyl]-3-methylphenyl]-3-methylpyridine-2-carboxamide

EXAMPLE 254

N-[4-[(5,11-Dihydro-10H-dibenz[b,e][1,4]diazepin-10-yl)carbonyl]-3-methylphenyl]-2-chloropyridine-3-carboxamide

EXAMPLE 255

N-[4-(5,11-Dihydro-10H-dibenz[b,e][1,4]diazepin-10-yl)carbonyl]-3,6-dimethylphenyl]-2-fluoropyridine-3-carboxamide

EXAMPLE 256

N-[4-[(5,11-Dihydro-10H-dibenz[b,e][1,4]diazepin-10-yl)carbonyl]-3-methyl-6-chlorophenyl]-2-chloropyridine-3-carboxamide

EXAMPLE 257

N-[5-[(5,11-Dihydro-10H-dibenz[b,e][1,4]diazepin-10-yl)carbonyl]-2-pyridinyl][1,1'-biphenyl]-2-carboxamide, m.p.280° C.–285° C.

EXAMPLE 258

N-[5-[(5,11-Dihydro-10H-dibenz[b,e][1,4]diazepin-10-yl)carbonyl]-2-pyridinyl]-2-(2-thienyl)benzamide

EXAMPLE 259

N-[5-[(5,11-Dihydro-10H-dibenz[b,e][1,4]diazepin-10-yl)carbonyl]-2-pyridinyl]-2-(3-thienyl)benzamide

EXAMPLE 260

N-[5-[(5,11-Dihydro-10H-dibenz[b,e][1,4]diazepin-10yl)carbonyl]-2-pyridinyl]-2-(2-furanyl))benzamide

EXAMPLE 261

N-[5-[(5,11-Dihydro-10H-dibenz[b,e][1,4]diazepin-10-yl)carbonyl]-2-pyridinyl]-2-(2-pyridinyl)benzamide

EXAMPLE 262

N-[5-[(5,11-Dihydro-10H-dibenz[b,e][1,4]diazepin-10-yl)carbonyl]-2-pyridinyl]-2-(3-pyridinyl)benzamide

EXAMPLE 263

N-[5-[(5,11-Dihydro-10H-dibenz[b,e][1,4]diazepin-10-yl)carbonyl]-2-pyridinyl]-2-(4-pyridinyl)benzamide

EXAMPLE 264

N-[5-[(5,11-Dihydro-10H-dibenz[b,e][1,4]diazepin-10-yl)carbonyl]-2-pyridinyl]-2-(2-furanyl)benzamide

EXAMPLE 265

N-[5-[(5,11-Dihydro-10H-dibenz[b,e][1,4]diazepin-10-yl)carbonyl]-2-pyridinyl]-2-(3-furanyl)benzamide

EXAMPLE 266

N-[5-[(5,11-Dihydro-10H-dibenz[b,e][1,4]diazepin-10-yl)carbonyl]-2-pyridinyl]-2-methoxypyridine-6-carboxamide

EXAMPLE 267

N-[5-[(5,11-Dihydro-10H-dibenz[b,e][1,4]diazepin-10-yl)carbonyl]-2-pyridinyl]pyridine-3-carboxamide

EXAMPLE 268

N-[5-[(5,11-Dihydro-10H-dibenz[b,e][1,4]diazepin-10-yl)carbonyl]-2-pyridinyl]-2-pyridinecarboxamide

EXAMPLE 269

N-[5-[(5,11-Dihydro-10H-dibenz[b,e][1,4]diazepin-10-yl)carbonyl]-2-pyridinyl]-2-methyl-5-fluorobenzamide

EXAMPLE 270

N-[5-[(5,11-Dihydro-10H-dibenz[b,e][1,4]diazepin-10-yl)carbonyl]-2-pyridinyl]-2-chlorobenzamide

EXAMPLE 271

N-[5-[(5,11-Dihydro-10H-dibenz[b,e][1,4]diazepin-10-yl)carbonyl]-2-pyridinyl]-2-chloro-5-fluorobenzamide

EXAMPLE 272

N-[5-[(5,11-Dihydro-10H-dibenz[b,e][1,4]diazepin-10-yl)carbonyl]-2-pyridinyl]-2-methylbenzamide

EXAMPLE 273

N-[5-[(5,11-Dihydro-10H-dibenz[b,e][1,4]diazepin-10-yl)carbonyl]-2-pyridinyl]-2,5-dimethylbenzamide

EXAMPLE 274

N-[5-[(5,11-Dihydro-10H-dibenz[b,e][1,4]diazepin-10-yl)carbonyl]-2-pyridinyl]-2-chloro-4-fluorobenzamide

EXAMPLE 275

N-[5-[(5,11-Dihydro-10H-dibenz[b,e][1,4]diazepin-10-yl)carbonyl]-2-pyridinyl]-2-chloro-6-fluorobenzamide

EXAMPLE 276

N-[5-[(5,11-Dihydro-10H-dibenz[b,e][1,4]diazepin-10-yl)carbonyl]-2-pyridinyl]-2-methyl-3-fluorobenzamide

EXAMPLE 277

N-[5-[(5,11-Dihydro-10H-dibenz[b,e][1,4]diazepin-10-yl)carbonyl]-2-pyridinyl]-2-hydroxybenzamide

EXAMPLE 278

N-[5-[(5,11-Dihydro-10H-dibenz[b,e][1,4]diazepin-10-yl)carbonyl]-2-pyridinyl]-2-acetyloxybenzamide

EXAMPLE 279

N-[5-[(5,11-Dihydro-10H-dibenz[b,e][1,4]diazepin-10-yl)carbonyl]-2-pyridinyl]-2-aminobenzamide

EXAMPLE 280

N-[5-[(5,11-Dihydro-10H-dibenz[b,e][1,4]diazepin-10-yl)carbonyl]-2-pyridinyl]-2-(methylamino)benzamide

EXAMPLE 281

N-[5-[(5,11-Dihydro-10H-dibenz[b,e][1,4]diazepin-10-yl)carbonyl]-2-pyridinyl]-2-(aminomethyl)benzamide

EXAMPLE 282

N-[5-[(5,11-Dihydro-10H-dibenz[b,e][1,4]diazepin-10-yl)carbonyl]-2-pyridinyl]-2-(dimethylamino)benzamide

EXAMPLE 283

N-[5-[(5,11-Dihydro-10H-dibenz[b,e][1,4]diazepin-10-yl)carbonyl]-2-pyridinyl]-2-chloropyridine-3-carboxamide

EXAMPLE 284

N-[5-[(5,11-Dihydro-10H-dibenz[b,e][1,4]diazepin-10-yl)carbonyl]-2-pyridinyl]-2-fluoropyridine-3-carboxamide

EXAMPLE 285

N-[5-[(5,11-Dihydro-10H-dibenz[b,e][1,4]diazepin-10-yl)carbonyl]-2-pyridinyl]-2-methoxypyridine-3-carboxamide

EXAMPLE 286

N-[5-[(5,11-Dihydro-10H-dibenz[b,e][1,4]diazepin-10-yl)carbonyl]-2-pyridinyl]-2-(methylthio)pyridine-3-carboxamide

EXAMPLE 287

N-[5-[(5,11-Dihydro-10H-dibenz[b,e][1,4]diazepin-10-yl)carbonyl]-2-pyridinyl]-2-aminopyridine-3-carboxamide

EXAMPLE 288

N-[5-[(5,11-Dihydro-10H-dibenz[b,e][1,4]diazepin-10-yl)carbonyl]-2-pyridinyl]-2-(methylamino)pyridine-3-carboxamide

EXAMPLE 289

N-[5-[(5,11-Dihydro-10H-dibenz[b,e][1,4]diazepin-10-yl)carbonyl]-2-pyridinyl]-2-(dimethylamino)pyridine-3-carboxamide

EXAMPLE 290

N-[5-[(5,11-Dihydro-10H-dibenz[b,e][1,4]diazepin-10-yl)carbonyl]-2-pyridinyl]-2-methylthiophene-3-carboxamide

EXAMPLE 300

N-[5-[(5,11-Dihydro-10H-dibenz[b,e][1,4]diazepin-10-yl)carbonyl]-2-pyridinyl]-3-methylthiophene-2-carboxamide

EXAMPLE 301

N-[4-[(6,11-Dihydro-5H-dibenz[b,e]azepin-5-yl)carbonyl]-phenyl][1,1'-biphenyl]-2-carboxamide A mixture of 6,11-dihydro-5H-dibenz[b,e]azepine (0.195 g), 4-[([1,1'-biphenyl]-2-carbonyl)amino]benzoyl chloride (0.41 g) and 0.155 g of N,N-diisopropylethylamine in 12 ml of dichloromethane is stirred at room temperature for 3 hours. The mixture is poured into water and extracted with dichloromethane. The extract is washed with $H_2O$, saturated $NaHCO_3$, $H_2O$, brine and dried ($Na_2SO_4$). The solution is filtered through a thin pad of hydrous magnesium silicate and the filter pad washed with dichloromethane. The filtrate is concentrated to dryness to give 0.66 g of a yellow l, solid. Chromatography on thick layer silica gel plates with hexane-ethyl acetate (1.5:1) gives crystals (0.165 g) (from dichloromethane-ethyl acetate), m.p. 224° C.–225° C.

EXAMPLE 302

N-[4-[(6,11-Dihydro-5H-dibenz[b,e]azepin-5-yl)carbonyl]-3-chlorophenyl][1,1'-biphenyl]-2-carboxamide A mixture of 0.195 g of 6,11-dihydro-5H-dibenz[b,e]azepine, 0.444 g of 4-[([1,1'-biphenyl]-2-carbonyl)amino]-2-chlorobenzoyl chloride and 0.155 g of N,N-diisopropylethylamine is stirred at room temperature for 3 hours. The mixture is poured into water and extracted with dichloromethane. The extract is washed with $H_2O$, saturated $NaHCO_3$, $H_2O$, brine and dried ($Na_2SO_4$). The solvent is removed and the residue chromatographed on thick layer silica gel plates with solvent hexane-ethyl acetate (1.5:1) to give 0.32 g of crystals, m.p. 120° C.–125° C.

As described for Example 302, the following compounds can be prepared by reaction of 6,11-dihydro-5H-dibenz[b,e]azepine with the appropriate substituted or unsubstituted 4-[(arycarbonyl)amino]benzoyl chloride or the appropriate substituted or unsubstituted 6-[(arycarbonyl)amino]pyridine-3-carbonyl chloride

EXAMPLE 303

N-[4-[(6,11-Dihydro-5H-dibenz[b,e]azepin-5-yl)carbonyl]phenyl]-2-(2-thienyl)benzamide

EXAMPLE 304

N-[4-[(6,11-Dihydro-5H-dibenz[b,e]azepin-5-yl)carbonyl]phenyl]-2-(3-thienyl)benzamide

EXAMPLE 305

N-[4-[(6,11-Dihydro-5H-dibenz[b,e]azepin-5-yl)carbonyl]phenyl]-3,6-dichlorophenyl]-2-(2-thienyl)benzamide

EXAMPLE 306

N-[4-[(6,11-Dihydro-5H-dibenz[b,e]azepin-5-yl)carbonyl]-3-chlorophenyl]-2-(2-thienyl)benzamide

EXAMPLE 307

N-[4-[(6,11-Dihydro-5H-dibenz[b,e]azepin-5-yl)carbonyl]-3-chlorophenyl]-2-(3-thienyl)benzamide

EXAMPLE 308

N-[4-[(6,11-Dihydro-5H-dibenz[b,e]azepin-5-yl)carbonyl]-3-chloro-6-methylphenyl]-2-(2-thienyl)benzamide

EXAMPLE 309

N-[4-[(6,11-Dihydro-5H-dibenz[b,e]azepin-5-yl)carbonyl]-3-methylphenyl]-2-(2-thienyl)benzamide

EXAMPLE 310

N-[4-[(6,11-Dihydro-5H-dibenz[b,e]azepin-5-yl)carbonyl]-3,6-dimethylphenyl]-2-(2-thienyl)benzamide

EXAMPLE 311

N-[4-[(6,11-Dihydro-5H-dibenz[b,e]azepin-5-yl)carbonyl]-3-methylphenyl][1,1'-biphenyl]-2-carboxamide

EXAMPLE 312

N-[4-[(6,11-Dihydro-5H-dibenz[b,e]azepin-5-yl)carbonyl]-3,6-dimethylphenyl][1,1'-biphenyl]-2-carboxamide

EXAMPLE 313

N-[4-[(6,11-Dihydro-5H-dibenz[b,e]azepin-5-yl)carbonyl]-3-methyl-6-chlorophenyl][1,1'-biphenyl]-2-carboxamide

EXAMPLE 314

N-[4-[(6,11-Dihydro-5H-dibenz[b,e]azepin-5-yl)carbonyl]-3-chloro-6-methylphenyl][1,1'-biphenyl]-2-carboxamide

EXAMPLE 315

N-[4-[(6,11-Dihydro-5H-dibenz[b,e]azepin-5-yl)carbonyl]-2-methylphenyl][1,1'-biphenyl]-2-carboxamide

EXAMPLE 316

N-[4-[(6,11-Dihydro-5H-dibenz[b,e]azepin-5-yl)carbonyl]-2-chlorophenyl][1,1'-biphenyl]-2-carboxamide

EXAMPLE 317

N-[4-[(6,11-Dihydro-5H-dibenz[b,e]azepin-5-yl)carbonyl]phenyl]-2-(2-pyridinyl)benzamide

EXAMPLE 318

N-[4-[(6,11-Dihydro-5H-dibenz[b,e]azepin-5-yl)carbonyl]phenyl]-2-(3-pyridinyl)benzamide

EXAMPLE 319

N-[4-[(6,11-Dihydro-5H-dibenz[b,e]azepin-5-yl)carbonyl]phenyl]-2-(4-pyridinyl)benzamide

EXAMPLE 320

N-[4-[(6,11-Dihydro-5H-dibenz[b,e]azepin-5-yl)carbonyl]-3-chlorophenyl]-2-(2-pyridinyl)benzamide

EXAMPLE 321

N-[4-[(6,11-Dihydro-5H-dibenz[b,e]azepin-5-yl)carbonyl]-3-chlorophenyl]-2-(3-pyridinyl)benzamide

EXAMPLE 322

N-[4-[(6,11-Dihydro-5H-dibenz[b,e]azepin-5-yl)carbonyl]-3-methylphenyl]-2-(2-pyridinyl)benzamide

EXAMPLE 323

N-[4-[(6,11-Dihydro-5H-dibenz[b,e]azepin-5-yl)carbonyl]-3-methylphenyl]-2-(3-pyridinyl)benzamide

EXAMPLE 324

N-[4-[(6,11-Dihydro-5H-dibenz[b,e]azepin-5-yl)carbonyl]-3,6-dimethylphenyl]-2-(2-pyridinyl)benzamide

EXAMPLE 325

N-[4-[(6,11-Dihydro-5H-dibenz[b,e]azepin-5-yl)carbonyl]-3,6-dimethylphenyl]-2-(3-pyridinyl)benzamide

EXAMPLE 326

N-[4-[(6,11-Dihydro-5H-dibenz[b,e]azepin-5-yl)carbonyl]-3,6-dimethylphenyl]-2-(4-pyridinyl)benzamide

EXAMPLE 327

N-[4-[(6,11-Dihydro-5H-dibenz[b,e]azepin-5-yl)carbonyl]-3-chlorophenyl]-[3'-methylthio-1,1'-biphenyl]-2-carboxamide

EXAMPLE 328

N-[4-[(6,11-Dihydro-5H-dibenz[b,e]azepin-5-yl)carbonyl]-3-chlorophenyl]-[3'-methoxy-1,1'-biphenyl]-2-carboxamide

EXAMPLE 329

N-[4-[(6,11-Dihydro-5H-dibenz[b,e]azepin-5-yl)carbonyl]phenyl][4'-dimethylamino-1,1'-biphenyl]-2-carboxamide

EXAMPLE 330

N-[4-[(6,11-Dihydro-5H-dibenz[b,e]azepin-5-yl)carbonyl]-3-methylphenyl]-[3'-chloro-1,1'-biphenyl]-2-carboxamide

EXAMPLE 331

N-[4-[(6,11-Dihydro-5H-dibenz[b,e]azepin-5-yl)carbonyl]-3-chlorophenyl]-2-(3-furanyl)benzamide

EXAMPLE 332

N-[4-[(6,11-Dihydro-5H-dibenz[b,e]azepin-5-yl)carbonyl]phenyl]-2-(2-furanyl)benzamide

EXAMPLE 333

N-[4-[(6,11-Dihydro-5H-dibenz[b,e]azepin-5-yl)carbonyl]phenyl]-[3'-chloro-1,1'-biphenyl]-2-carboxamide

EXAMPLE 334

N-[4-[(6,11-Dihydro-5H-dibenz[b,e]azepin-5-yl)carbonyl]-3-chlorophenyl][3'-chloro-1,1'-biphenyl]-2-carboxamide

EXAMPLE 335

N-[4-[(6,11-Dihydro-5H-dibenz[b,e]azepin-5-yl)carbonyl]-3-methylphenyl][3'-chloro-1,1'-biphenyl]-2-carboxamide

EXAMPLE 336

N-[5-[(6,11-Dihydro-5H-dibenz[b,e]azepin-5-yl)carbonyl]-2-pyridinyl][3'-chloro-1,1'-biphenyl]-2-carboxamide

EXAMPLE 337

N-[4-[(6,11-Dihydro-5H-dibenz[b,e]azepin-5-yl)carbonyl]-3-chlorophenyl][4'-fluoro-1,1'-biphenyl]-2-carboxamide

EXAMPLE 338

N-[5-[(6,11-Dihydro-5H-dibenz[b,e]azepin-5-yl)carbonyl]-2-pyridinyl]-2-chloropyridine-3-carboxamide

EXAMPLE 339

N-[5-[(6,11-Dihydro-5H-dibenz[b,e]azepin-5-yl)carbonyl]-2-pyridinyl]-2-fluoropyridine-3-carboxamide

EXAMPLE 340

N-[5-[(6,11-Dihydro-5H-dibenz[b,e]azepin-5-yl)carbonyl]-2-pyridinyl]-2-aminopyridine-3-carboxamide

EXAMPLE 341

N-[5-[(6,11-Dihydro-5H-dibenz[b,e]azepin-5-yl)carbonyl]-2-pyridinyl]-2-(methylamino)pyridine-3-carboxamide

EXAMPLE 342

N-[5-[(6,11-Dihydro-5H-dibenz[b,e]azepin-5-yl)carbonyl]-2-pyridinyl]-2-(dimethylamino)pyridine-3-carboxamide

EXAMPLE 343

N-[5-[(6,11-Dihydro-5H-dibenz[b,e]azepin-5-yl)carbonyl]-2-pyridinyl]-3-methylthiophene-2-carboxamide

EXAMPLE 344

N-[5-[(6,11-Dihydro-5H-dibenz[b,e]azepin-5-yl)carbonyl]-2-pyridinyl]-2-methylthiophene-3-carboxamide

EXAMPLE 345

N-[5-[(6,11-Dihydro-5H-dibenz[b,e]azepin-5-yl)carbonyl]-2-pyridinyl]-2-chlorobenzamide

EXAMPLE 346

N-[5-[(6,11-Dihydro-5H-dibenz[b,e]azepin-5-yl)carbonyl]-2-pyridinyl]-2-chloro-5-fluorobenzamide

EXAMPLE 347

N-[5-[(6,11-Dihydro-5H-dibenz[b,e]azepin-5-yl)carbonyl]-2-pyridinyl]-2-chloro-6-fluorobenzamide

EXAMPLE 348

N-[5-[(6,11-Dihydro-5H-dibenz[b,e]azepin-5-yl)carbonyl]-2-pyridinyl]-2-methyl-3-fluorobenzamide

EXAMPLE 349

N-[5-[(6,11-Dihydro-5H-dibenz[b,e]azepin-5-yl)carbonyl]-2-pyridinyl]-2-(methylamino)benzamide

EXAMPLE 350

N-[5-[(6,11-Dihydro-5H-dibenz[b,e]azepin-5-yl)carbonyl]-2-pyridinyl]-2-hydroxybenzamide

EXAMPLE 351

N-[5-[(6,11-Dihydro-5H-dibenz[b,e]azepin-5-yl)carbonyl]-2-pyridinyl]-2-(aminomethyl)benzamide

EXAMPLE 352

N-[5-[(6,11-Dihydro-5H-pyrido[2,3-b][1,4]benzodiazepin-5-yl)carbonyl]-2-pyridinyl]-5-fluoro-2-methylbenzamide As described for Example 1, 6,11-dihydro-5H-pyrido[2,3-b][1,4]benzodiazepine (2 mmol) is reacted with 6-[(5-fluoro-2-methylbenzoyl)amino]pyridine-3-carbonyl chloride (2.1 mmol) in the presence of triethylamine (4 mmol) in dichloromethane to give the product as a solid, m.p. 102° C.–104° C.

EXAMPLE 353

N-[4-[(6,11-Dihydro-5H-pyrido[2,3-b][1,4]benzodiazepin-5-yl)carbonyl]-3-chlorophenyl][1,1'-biphenyl]-2-carboxamide As described for Example 134, 6,11-dihydro-5H-pyrido[2,3-b][1,4]benzodiazepine (0.197 g) is reacted with 4-[([1,1'-biphenyl]-2-carbonyl)amino]-2-chlorobenzoyl chloride (0.444 g) in the presence of N,N-diisopropylethylamine (0.155 g) in 12 ml of dichloromethane to give the product as a solid.

As described for Example 352, the following compounds can be prepared by reaction of 6,11-dihydro-5H-pyrido[2,3-b][1,4]benzodiazepine with the appropriate substituted or unsubstituted 4-[(arylcarbonyl)amino]benzoyl chloride or the appropriate substituted or unsubstituted 6-[(arylcarbonyl)amino]pyridine-3-carbonyl chloride

EXAMPLE 354

N-[4-[(6,11-Dihydro-5H-pyrido[2,3-b][1,4]benzodiazepin-5-yl)carbonyl]phenyl][1,1'-biphenyl]-2-carboxamide

EXAMPLE 355

N-[4-[(6,11-Dihydro-5H-pyrido[2,3-b][1,4]benzodiazepin-5-yl)carbonyl]phenyl]-2-(2-thienyl)benzamide

EXAMPLE 356

N-[4-[(6,11-Dihydro-5H-pyrido[2,3-b][1,4]benzodiazepin-5-yl)carbonyl]-3-methylphenyl][1,1'-biphenyl]-2-carboxamide

EXAMPLE 357

N-[4-[(6,11-Dihydro-5H-pyrido[2,3-b][1,4]benzodiazepin-5-yl)carbonyl]-3-methyl-6-chlorophenyl][1,1'-biphenyl]-2-carboxamide

EXAMPLE 358

N-[4-[(6,11-Dihydro-5H-pyrido[2,3-b][1,4]benzodiazepin-5-yl)carbonyl]-3,6-dimethylphenyl][1,1'-biphenyl]-2-carboxamide

EXAMPLE 359

N-[4-[(6,11-Dihydro-5H-pyrido[2,3-b][1,4]benzodiazepin-5-yl)carbonyl]-3-methylphenyl]-2-(2-thienyl)benzamide

EXAMPLE 360

N-[4-[(6,11-Dihydro-5H-pyrido[2,3-b][1,4]
benzodiazepin-5-yl)carbonyl]-3-chlorophenyl]-2-(2-
thienyl)benzamide

EXAMPLE 361

N-[4-[(6,11-Dihydro-5H-pyrido[2,3-b][1,4]
benzodiazepin-5-yl)carbonyl]phenyl]-2-(2-pyridinyl)
benzamide

EXAMPLE 362

N-[4-[(6,11-Dihydro-5H-pyrido[2,3-b][1,4]
benzodiazepin-5-yl)carbonyl]phenyl]-2-(3-pyridinyl)
benzamide

EXAMPLE 363

N-[4-[(6,11-Dihydro-5H-pyrido[2,3-b][1,4]
benzodiazepin-5-yl)carbonyl]-3-chlorophenyl]-2-(2-
pyridinyl)benzamide

EXAMPLE 364

N-[4-[(6,11-Dihydro-5H-pyrido[2,3-b][1,4]
benzodiazepin-5-yl)carbonyl]-3-chlorophenyl]-2-(3-
pyridinyl)benzamide

EXAMPLE 365

N-[4-[(6,11-Dihydro-5H-pyrido[2,3-b][1,4]
benzodiazepin-5-yl)carbonyl]-3-methylphenyl]-2-(2-
pyridinyl)benzamide

EXAMPLE 366

N-[4-[(6,11-Dihydro-5H-pyrido[2,3-b][1,4]
benzodiazepin-5-yl)carbonyl]-3,6-dimethylphenyl]-
2-(3-pyridinyl)benzamide

EXAMPLE 367

N-[4-[(6,11-Dihydro-5H-pyrido[2,3-b][1,4]
benzodiazepin-5-yl)carbonyl]phenyl]-2-(4pyridinyl)
benzamide

EXAMPLE 368

N-[4-[(6,11-Dihydro-5H-pyrido[2,3-b][1,4]
benzodiazepin-5-yl)carbonyl]phenyl]-2-
chloropyridine-3-carboxamide

EXAMPLE 369

N-[4-[(6,11-Dihydro-5H-pyrido[2,3-b][1,4]
benzodiazepin-5-yl)carbonyl]phenyl]-2-
fluoropyridine-3-carboxamide

EXAMPLE 370

N-[4-[(6,11-Dihydro-5H-pyrido[2,3-b][1,4]
benzodiazepin-5-yl)carbonyl]-3-chlorophenyl]-2-
chloropyridine-3-carboxamide

EXAMPLE 371

N-[4-[(6,11-Dihydro-5H-pyrido[2,3-b][1,4]
benzodiazepin-5-yl)carbonyl]phenyl]-2-
methoxypyridine-3-carboxamide

EXAMPLE 372

N-[4-[(6,11-Dihydro-5H-pyrido[2,3-b][1,4]
benzodiazepin-5-yl)carbonyl]-3-methylphenyl]-2-
(methylthio)pyridine-3-carboxamide

EXAMPLE 373

N-[4-[(6,11-Dihydro-5H-pyrido[2,3-b][1,4]
benzodiazepin-5-yl)carbonyl]-3-methylphenyl]-2-
chloropyridine-3-carboxamide

EXAMPLE 374

N-[4-[(6,11-Dihydro-5H-pyrido[2,3-b][1,4]
benzodiazepin-5-yl)carbonyl]phenyl]-2-
aminopyridine-3-carboxamide

EXAMPLE 375

N-[5-[(6,11-Dihydro-5H-pyrido[2,3-b][1,4]
benzodiazepin-5-yl)carbonyl]-2-pyridinyl][1,1'-
biphenyl]-2-carboxamide

EXAMPLE 376

N-[5-[(6,11-Dihydro-5H-pyrido[2,3-b][1,4]
benzodiazepin-5-yl)carbonyl]-2-pyridinyl]-2-(2-
thienyl)benzamide

EXAMPLE 377

N-[5-[(6,11-Dihydro-5H-pyrido[2,3-b][1,4]
benzodiazepin-5-yl)carbonyl]-2-pyridinyl]-2-(3-
thienyl)benzamide

EXAMPLE 378

N-[5-[(6,11-Dihydro-5H-pyrido[2,3-b][1,4]
benzodiazepin-5-yl)carbonyl]-2-pyridinyl]-2-(2-
pyridinyl)benzamide

EXAMPLE 379

N-[5-[(6,11-Dihydro-5H-pyrido[2,3-b][1,4]
benzodiazepin-5-yl)carbonyl]-2-pyridinyl]-2-(3-
pyridinyl)benzamide

EXAMPLE 380

N-[5-[(6,11-Dihydro-5H-pyrido[2,3-b][1,4]
benzodiazepin-5-yl)carbonyl]-2-pyridinyl]-2-(4-
pyridinyl)benzamide

EXAMPLE 381

N-[5-[(6,11-Dihydro-5H-pyrido[2,3-b][1,4]
benzodiazepin-5-yl)carbonyl]-2-pyridinyl]-2-(2-
furanyl)benzamide

EXAMPLE 382

N-[5-[(6,11-Dihydro-5H-pyrido[2,3-b][1,4]
benzodiazepin-5-yl)carbonyl]-2-pyridinyl]-2-(3-
furanyl)benzamide

EXAMPLE 383

N-[5-[(6,11-Dihydro-5H-pyrido[2,3-b][1,4]
benzodiazepin-5-yl) carbonyl]-2-pyridinyl]-2-
chlorobenzamide

EXAMPLE 384

N-[5-[(6,11-Dihydro-5H-pyrido[2,3-b][1,4]
benzodiazepin-5-yl)carbonyl]-2-pyridinyl]-2-chloro-
5-fluorobenzamide

EXAMPLE 385

N-[5-[(6,11-Dihydro-5H-pyrido[2,3-b][1,4]
benzodiazepin-5-yl)carbonyl]-2-pyridinyl]-2,5-
dimethylbenzamide

EXAMPLE 386

N-[5-[(6,11-Dihydro-5H-pyrido[2,3-b][1,4]
benzodiazepin-5-yl)carbonyl]-2-pyridinyl]-2-chloro-
6-fluorobenzamide

EXAMPLE 387

N-[5-[(6,11-Dihydro-5H-pyrido[2,3-b][1,4]
benzodiazepin-5-yl)carbonyl]-2-pyridinyl]-2-methyl-
3-fluorobenzamide

EXAMPLE 388

N-[5-[(6 11-Dihydro-5H-pyrido[2,3-b][1,4]
benzodiazepin-5-yl)carbonyl]-2-pyridinyl]-2-
hydroxybenzamide

EXAMPLE 389

N-[5-[(6,11-Dihydro-5H-pyrido[2,3-b][1,4]
benzodiazepin-5-yl)carbonyl]-2-pyridinyl]-2-
aminobenzamide

EXAMPLE 390

N-[5-[(6,11-Dihydro-5H-pyrido[2,3-b][1,4]
benzodiazepin-5-yl)carbonyl]-2-pyridinyl]-2-
(methylamino)benzamide

EXAMPLE 391

N-[5-[(6,11-Dihydro-5H-pyrido[2,3-b][1,4]
benzodiazepin-5-yl)carbonyl]-2-pyridinyl]-2-
(dimethylamino)benzamide

EXAMPLE 392

N-[5-[(6,11-Dihydro-5H-pyrido[2,3-b][1,4]
benzodiazepin-5-yl)carbonyl]-2pyridinyl]-2-
chloropyridine-3-carboxamide

EXAMPLE 393

N-[5-[(6,11-Dihydro-5H-pyrido[2,3-b][1,4]
benzodiazepin-5-yl)carbonyl]-2-pyridinyl]-2-
(dimethylamino)pyridine-3-carboxamide

EXAMPLE 394

N-[5-[(6,11-Dihydro-5H-pyrido[2,3-b][1,4]
benzodiazepin-5-yl)carbonyl]-2pyridinyl]-2-
methylthiophene-3-carboxamide

EXAMPLE 395

N-[5-[(6,11-Dihydro-5H-pyrido[2,3-b][1,4]
benzodiazepin-5-yl)carbonyl]-2-pyridinyl]-3-
methylthiophene-2-carboxamide

EXAMPLE 396

N-[4-[(4,5-Dihydropyrazolo[4,3-d][1]benzazepin-6
(1H)-yl)carbonyl]phenyl]1,1'-biphenyl]-2-
carboxamide A mixture of 0.278 g of 4,5-dihydropyrazolo[4,3-d][1]benzazepine, 1.11 g of 4-[([1,1'-biphenyl]-2-carbonyl)amino]benzoyl chloride and 0.426 g of N,N-diisopropylethylamine in 12 ml of dichloromethane-tetrahydrofuran (1:1) is stirred at room temperature overnight. The mixture is poured into water and extracted with dichloromethane. The extract is washed with 2N Na$_2$CO$_3$, H$_2$O, brine and dried (Na$_2$SO$_4$). The solvent is removed under vacuum to give 1.45 g of solid. To the preceding solid in 25 ml methanol-tetrahydrofuran (1:1) is added 2.78 ml of 2N NaOH and the solution stirred at room temperature for 3.5 hours. The solvent is removed under vacuum, water added to the residue and the mixture extracted with dichloromethane. The extract is washed with H$_2$O, 0.5N citric acid; H$_2$O, brine and dried (Na$_2$SO$_4$). The solution is passed through a thin pad of hydrous magnesium silicate and the filtrate concentrated to dryness. The residue (0.95 g) is triturated with ether-dichloromethane to give 0.27 g of crystals, m.p. 255° C.–260° C.; Anal. found for $C_{31}H_{24}N_4O_2 \cdot \frac{1}{2}H_2O$: C, 75.9; H, 5.1; N, 10.8.

EXAMPLE 397

N-[4-[(4,5-Dihydropyrazolo[4,3-d][1]benzazepin-6(1H)-yl)carbonyl]-3-chlorophenyl[1,1'-biphenyl]-2-carboxamide A mixture of 0.185 g of 4,5-dihydropyrazolo[4,3-d][1]benzazepine, 0.814 g of 4-[([1,1'-biphenyl]-2-carbonyl)amino]-2-chlorobenzoyl chloride and 0.284 g of N,N-diisopropylethylamine in 9 ml of dichloromethane-tetrahydrofuran (1:1) is stirred at room temperature overnight. The mixture is poured into water and extracted with dichloromethane. The extract is washed with 2N NaOH, H₂O, brine and dried (Na₂SO₄). The solvent is removed under vacuum to give 0.99 g of a solid. To the preceding solid in 15 ml of methanol-tetrahydrofuran (1:1) is added 1.75 ml of 2N NaOH and the solution stirred at room temperature for 2 hours. The volatiles are removed under vacuum and the mixture extracted with chloroform. The extract is washed with 1N citric acid, H₂O, brine and dried (Na₂SO₄). The solution is filtered through a thin pad of hydrous magnesium silicate and the filtrate concentrated to dryness. The residue (0.76 g) is chromatographed on thick layer silica gel plates with hexane-ethyl acetate (1:2) as solvent to give 0.37 g of white solid, m.p. 172°–202° C., Anal. found for ½ hydrate: C, 70.1; H, 5.0; N, 9.8; Cl, 6.4.

EXAMPLE 398

N-[5-[(4,5-Dihydropyrazolo[4,3-d][1]benzazepin-6(1H)-yl)carbonyl]-2-pyridinyl][1,1'-biphenyl]-2-carboxamide As described for Example 396, (0.1 mmol) of 4,5-dihydropyrazolo[4,3-d][1]benzazepine is reacted with (0.21 mmol) of 6-[([1,1'-biphenyl]-2-carbonyl)amino]pyridine-3-carbonyl chloride to give the product as a light tan solid. Recrystallized from ethyl acetate/hexane, m.p. 228° C.–234° C. as white crystals.

EXAMPLE 399

N-[5-[(4,5-Dihydropyrazolo[4,3-d][1]benzazepin-6(1H)-yl)carbonyl]-2-pyridinyl]-5-fluoro-2-methylbenzamide As described for Example 396, 0.10 mmol of 4,5-dehydropyrazolo[4,3-d][1]benzazepine is reacted with 0.21 mmol of 6-[(5-fluoro-2-methylbenzoyl)amino]-2-pyridine-3-carbonyl chloride to give the product as a tan solid, (0.15 g) m.p. 126° C.–176° C.: Mass Spec (FAB)-found 442(M⁺+H).

EXAMPLE 400

N-[5-(4H-Thieno[3,4-b][1,5]benzodiazepin-9(10H)-yl-2-pyridinyl]-5-fluoro-2-methylbenzamide As described by J. B. Press et al in *J. Med. Chem.*, 22, 725 (1979), 9,10-dihydro-4H-thieno[3,4-b][1,5]benzodiazepin-10(9H)-one is prepared. This intermediate (4.8 g) is dissolved in tetrahydrofuran under nitrogen and 4.2 g of lithium aluminum hydride (LAH) is added portionwise with stirring. The mixture is refluxed for 18 hours and quenched by the dropwise addition of water. The mixture is extracted with chloroform and the extract is filtered through diatomaceous earth. The organic layer is washed with water (200 ml), dried (Na₂SO₄) and the solvent removed. The residual oil is chromatographed on thick layer silica gel plates with chloroform as eluent to give 1.2 g of 9,10-dihydro-4H-thieno[3,4-b][1,5]benzodiazepine as a solid. The proceeding compound (0.5 g) is reacted with 1.06 g of 6-[(5-fluoro-2-methylbenzoyl)amino]pyridine-3-carbonyl chloride, hydrochloride in dichloromethane which contains 7 ml of N,N-diisopropylethylamine. The mixture is stirred at room temperature for 16 hours and then is washed with water, 1N HCl, saturated sodium bicarbonate solution, water and dried (Na₂SO₄). The solvent is removed and the residue purified by chromatography on silica gel with ethyl acetate-hexane (1:3) to give 1.1 g of a solid, m.p. 89° C.–92° C.

EXAMPLE 401

N-[4-(4H-Thieno[3,4-b]1,5]benzodiazepin-9(10H)-yl)-phenyl][1,1'-biphenyl]-2-carboxamide As described for Example 400, 9,10-dihydro-4H-thieno[3,4-b][1,5]benzodiazepine is reacted with 4-[([1,1'-biphenyl]-2-carbonyl)amino]benzoyl chloride to give the product as a solid.

EXAMPLE 402

N-[4-(4H-Thieno[3,4-b][1,5]benzodiazepin-9(10H)-yl)-3-chlorophenyl][1,1'-biphenyl]-2-carboxamide As described for Example 400, 9,10-dihydro-4H-thieno[3,4-b][1,5]benzodiazepine is reacted with 4-[([1,1'-biphenyl]-2-carbonyl)amino]-2-chlorobenzoyl chloride to give the product as a solid.

EXAMPLE 403

N-[5-(4H-Thieno[3,4-b][1,5]benzodiazepin-9(10H)-yl)-2-pyridinyl][1,1'-biphenyl]-2-carboxamide As described for Example 400, 9,10-dihydro-4H-thieno[3,4-b][1,5]benzodiazepine is reacted with 6-[([1,1'-biphenyl]-2-carbonyl)amino]-pyridine-3-carbonyl chloride to give the product as a solid.

EXAMPLE 404

5,11-Dihydro-10-[4-(2-thienyl)benzoyl]-10H-dibenz[b,e][1,4]diazepine

A mixture of 3 g of 4-(2-thienyl)benzoic acid and 30 ml of sulfonyl chloride is refluxed for 45 minutes and the solvent removed. The residue is dissolved in carbon tetrachloride and the solvent removed under vacuum (2-times) to give 4-(2-thienyl) benzoyl chloride. To a cooled (0° C.) solution of 2.0 g of 5,11-dihydro-10H-dibenz[b,e][1,4]diazepine and 7 ml of N,N-diisopropylethylamine in 30 ml of dichloromethane is added dropwise a solution of 3.15 g of 4-(2-thienyl)benzoyl chloride in 30 ml of dichloromethane. The mixture is stirred at room temperature for 16 hours and diluted with 50 ml of chloroform. The solution is washed with 30 ml each of water, 2N HCl, saturated NaHCO₃, water and dried (Na₂SO₄). The solvent is removed under vacuum and the residue (3.1 g) chromatographed on silica gel (column) with hexane-ethyl acetate (2:1) as eluent to give 1.8 g of solid, m.p. 114° C.–116° C.

EXAMPLE 405

5,11-Dihydro-10-[4-(3-thienyl)benzoyl]-10H-dibenz[b,e][1,4]diazepine

To a mixture of 2.0 g of 5,11-dihydro-10H-dibenz[b,e][1,4]diazepine and 7 ml of N,N- diisopropylethylamine in 30 ml of dichloromethane is added dropwise a solution of 3.15 g of 4-(3-thienyl)benzoyl chloride in 30 ml of dichloromethane. The mixture is stirred 16 hours at room temperature and diluted with dichloromethane (50 ml). The solution is washed with 30 ml each of $H_2O$, 2N HCl, saturated $NaHCO_3$, water and dried ($Na_2SO_4$). The solvent is removed under vacuum and the residue purified by chromatography on silica gel with hexane-ethyl acetate as eluent to give a solid.

Binding Assay to Rat Hepatic $V_1$ Receptors

Rat liver plasma membranes expressing the vasopressin $V_1$ receptor subtypes are isolated by sucrose density gradient according to the method described by Lesko et al., (1973). These membranes are quickly suspended in 50.0 mM Tris.HCl buffer, pH 7.4, containing 0.2% bovine serum albumin (BSA) and 0.1 mM phenylmethylsulfonylfluoride (PMSF) and kept frozen at $-70°$ C. until used in subsequent binding experiments. For binding experiments, the following is added to the wells of a ninety-six well format microtiter plate: 100 ml of 100.0 ml Tris.HCl buffer containing 10.0 mM $MgCl_2$, 0.2% heat inactivated BSA and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 ml of [phenylalanyl-3,4,5, $-^3H$] vasopressin (S.A. 45.1 Ci/mmole) 0.8 mM, and the reaction initiated by the addition of 80 ml of tissue membranes containing 20 mg of tissue protein. The plates are kept undisturbed on the bench top at room temperature for 120 min. to reach equilibrium. Non-specific samples are assayed in the presence of 0.1 mM of the unlabeled antagonist phenylalanylvasopressin, added in 20.0 ml volume.

For test compounds, these are solubilized in 50% dimethylsulfoxide (DMSO) and added in 20.0 ml volume to a final incubation volume of 200 ml. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, OH) and displayed in Table I.

Binding Assay to Rat Kidney Medullary $V_2$ Receptors

Medullary tissues from rat kidneys are dissected out, cut into small pieces and soaked in a 0.154 mM sodium chloride solution containing 1.0 mM EDTA with many changes of the liquid phase, until the solution is clear of blood. The tissue is homogenized in a 0.25M sucrose solution containing 1.0 mM EDTA with many changes of the liquid phase, until the solution is clear of blood. The tissue is homogenized in a 0.25M sucrose solution containing 1.0 mM EDTA and 0.1 mM PMSF using a Potter-Elvehjem homogenizer with a teflon pestle. The homogenate is filtered through several layers (4 layers) of cheese cloth. The filtrate is rehomogenized using a dounce homogenizer, with a tight fitting pestle. The final homogenate is centrifuged at 1500×g for 15 min. The nuclear pellet is discarded and the supernatant fluid recentrifuged at 40,000×g for 30 min. The resulting pellet formed contains a dark inner part with the exterior, slightly pink. The pink outer part is suspended in a small amount of 50.0 mM Tris.HCl buffer, pH 7.4. The protein content is determined by the Lowry's method (Lowry et al., *J. Biol. Chem.,* 1953). The membrane suspension is stored at $-70°$ C., in 50.0 mM Tris.HCl, containing 0.2% inactivated BSA and 0.1 mM PMSF in aliquots of 1.0 ml containing 10.0 mg protein per ml of suspension until sue in subsequent binding experiments.

For binding experiments, the following is added in ml volume to wells of a 96 well format of a microtiter plate: 100.0 ml of 100.0 mM Tris.HCl buffer containing 0.2% heat inactivated BSA, 10.0 mM $MgCL_2$ and a mixture of protease inhibitors: leupeptin, 1.0 mg %; aprotinin, 1.0 mg % 1,10-phenanthroline, 2.0 mg %; trypsin inhibitor, and 0.1 mM PMSF, 20.0 ml of [$^3H$] Arginine$^8$, vasopressin (S.A. 75.0 Ci/mmole) at 0.8 nM and the reaction initiated by the addition of 80.0 ml of tissue membranes (200.0 mg tissue protein). The plates are left undisturbed on the bench top for 120 minutes to reach equilibrium. Non-specific binding is assessed in the presence of 1.0 mM of unlabeled ligand, added in 20 ml volume. For test compounds, these are solubilized in 50% dimethylsulfoxide (DMSO) and added in 20.0 ml volume to a final incubation volume of 200 ml. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Parkard LS Counter, with an efficiency of 65% for tritium. The data are analyzed for $IC_{50}$ values by the LUNDON-2 program for competition (LUNDON SOFTWARE, OH) and displayed in Table I.

Radioligand Binding Experiments with Human Platelet Membranes (a) Platelet Membrane Preparation Frozen platelet rich plasma (PRP), received from the Hudson Valley Blood Services, are thawed to room temperature. (Platelet Source: Hudson Valley Blood Services, Westchester Medical Center, Valhalla, N.Y.). The tubes containing the PRP are centrifuged at 16,000×g for 10 minutes at 4° C. and the supernatant fluid discarded. The platelets resuspended in an equal volume of 50.0 mM Tris.HCL, pH 7.5 containing 120 mM NaCl and 20.0 mM EDTA. The suspension is recentrifuged at 16,000×g for 10 minutes. This washing step is repeated one more time. The wash discarded and the lysed pellets homogenized in low ionic strength buffer of Tris. HCl, 5.0 m, pH 7.5 containing 5.0 mM EDTA. The homogenate is centrifuged at 39,000×g for 10 minutes. The resulting pellet is resuspended in Tris.HCl buffer, 70.0 mM, pH 7.5 and recentrifuged at 39,000×g for 10 minutes. The final pellet is resuspended in 50.0 mM Tris.HCI buffer pH 7.4 containing 120 mM NaCl and 5.0 mM KCl to give 1.0–2.0 mg protein per ml of suspension.

(b) Binding to Vasopressin $V_1$ receptor subtype in Human Platelet Membranes

In wells of a 96 well format microtiter plate, add 100 ml of 50.0 mM Tris. HCl buffer containing 0.2% BSA and a mixture of protease inhibitors (aprotinin, leupeptin etc.) Then add 20 ml of [$^3H$]Ligand (Manning or Arg$^8$Vasopressin), to give final concentrations ranging from 0.01 to 10.0 nM. Initiate the binding by adding 80.0 ml of platelet suspension (approx. 100 mg protein). Mix all reagents by pipetting the mixture up and down a few times. Non specific binding is measured in the presence of 1.0 mM of unlabeled ligand (Manning or Arg$^8$Vasopressin). Let the mixture stand undisturbed at room temperature for ninety (90) minutes. Upon this time, rapidly filter off the incubate under vacuum suction over GF/B filters, using a Brandel Harvester. The radioactivity caught on the filter disks is determined by the addition of liquid scintillant and counting in a liquid scintillator.

Binding to Membranes of Mouse Fibroblast Cell Line (LV-2) Transfected with the cDNA Expressing the Human $V_2$ Vasopressin Receptor (a) Membrane Preparation Flasks of 175 ml capacity, continuing attached cells grown to confluence, are cleared of culture medium by aspiration. The flasks containing the attached cells are rinsed with 2×5 ml of phosphate buffered saline (PBS) and the liquid aspirated off each time. Finally, 5 ml of an enzyme free dissociation Hank's based solution (Specialty Media, Inc., Lafayette, N.J. is added and the flasks are left undisturbed for 2 minutes. The content of all flasks is poured into a centrifuge tube and the cells pelleted at 300×g for 15 minutes. The Hank's based solution is aspirated off and the cells homogenized with a polytron at setting #6 for 10 sec in 10.0 mM Tris.HCl buffer, pH 7.4 containing 0.25M sucrose and 1.0 mM EDTA. The homogenate is centrifuged at 1500×g for 10 minutes to remove ghost membranes. The supernatant fluid is centrifuged at 100,000×g for 60 minutes to pellet the receptor protein. Upon completion, the pellet is resuspended in a small volume of 50.0 mM Tris.HCl buffer, pH 7.4. The protein content is determined by the Lowry method and the receptor membranes are suspended in 50.0 mM Tris.HCl buffer containing 0.1 mM phenylmethylsulfonylfluoride (PMSF) and 0.2% bovine serum albumin (BSA) to give 2.5 mg receptor protein per ml of suspension.

(b) Receptor Binding

For binding experiments, the following is added in ml volume to wells of a 96 well format of a microtiter plate: 100.0 ml of 100.0 mM Tris.HCl buffer containing 0.2% heat inactivated BSA, 10.0 mM $MgCl_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF., 20.0 ml of [$^3$H] Arginine$^8$, vasopressin (S.A. 75.0 Ci/mmole) at 0.8 nM and the reaction initiated by the addition of 80.0 ml of tissue membranes (200.0 mg tissue protein). The plates are left undisturbed on the bench top for 120 minutes to reach equilibrium. Non specific binding is assessed in the presence of 1.0 mM of unlabeled ligand, added in 20 ml volume. For test compounds, these are solubilized in 50% dimethylsulfoxide (DMSO) and added in 20.0 ml volume to a final incubation volume of 200 ml. Upon completion of biding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, OH) and the data is displayed in Table I.

Vasopressin $V_2$ Antagonist Activity in Conscious Hydrated Rats

Conscious hydrated rats are treated with compounds under study from 0.1 to 100 mg/kg orally or vehicle. Two to four rats are used for each compound. One hour later, arginine vasopressin (AVP, antidiuretic Hormone, ADH) dissolved in peanut oil is administered at 0.4 mg/kg intraperitoneally. Two rats in each test would not receive arginine vasopressin but only the vehicle (peanut oil) to serve as water-loading control. Twenty minutes later each rat is given 30 mL/kg of deionized water orally by gavage and is placed individually in a metabolic cage equipped with a funnel and a graduated glass cylinder to collect urine for four hours. Urine volume is measure and osmolality analyzed by use of a Fiske One-Ten osmometer (Fiske Assoc., Norwood, Mass., USA). Urinary sodium, potassium, and chloride are analyzed by use of ion-specific electrodes in a Beckman E3 (Electrolye 3) Analyzer. In the following results, decreased urine volume and decreased osmolality relative to AVP-control indicates activity.

Vasopressin $V_1$ Antagonist Activity in Conscious Rats

Conscious rats are restrained in a supine position with elastic tape. The area at the base of the tail is locally anesthetized by subcutaneous infiltration with 2% procaine (0.2 ml). Using aseptic technique to the ventral caudal tail artery is isolated and a cannula made of PE 10 and 20 (heat-fused) tubing is passed into the lower abdominal aorta. The cannula is secured, heparinized (1000 iu/cc), sealed and the wound closed with one or two stitches of Dexon 4-0. The caudal vein is also cannulated in the same manner for intravenous drug administration. The duration of the surgery is approximately 5 minutes. Additional local anesthesia (2% procaine or lidocaine) is provided as needed.

The animals are placed in plastic restraining cages in an upright position. The cannula is attached to a Statham P23Db pressure transducer and pulsatile blood pressure is recorded. Increase of systolic blood pressure responses to arginine vasopressin 0.01 and 0.2 international unit (I.U.) (350 I.U.=1 mg) injections are recorded prior to any drug (compound) administration, after which each rat is dosed orally with compounds under study 0.1–100 mg/kg (10 cc/kg) or intravenously 0.1–30 mg/kg (1 cc/kg). The vasopressin injections are repeated 30,60,90,120,180,240 and 300 minutes later. Percentage of antagonism by the compound is calculated using the pre-drug vasopressin vasopressor response as 100%.

Oxytocin Receptor Binding (a) Membrane Preparation

Female Sprague-Dawley rats weighing approximately 200–250 g are injected intramuscularly (i.m.) with 0.3 mg/kg of body weight of diethylstilbestrol (DES). The rats are sacrificed 18 hours later under pentobarbital anesthesia. The uteri are dissected out, cleaned of fat and connective tissues and rinsed in 50 ml of normal saline. The tissue pooled from six rats is homogenized in 50 ml of 0.01 mM Tris. HCl, containing 0.5 mM dithiothreitol and 1.0 mM EDTA, adjusted to pH 7.4, using a polytron at setting 6 with three passes of 10 sec each. The homogenate is passed through two (2) layers of cheesecloth and the filtrate centrifuged at 1000×g for 10 minutes. The clear supernatant is removed and recentrifuged at 165,000×g for 30 minutes. The resulting pellet containing the oxytocin receptors is resuspended in 50.0 mM Tris.HCl containing 5.0 mM $MgCl_2$ at pH 7.4, to give a protein concentration of 2.5 mg/ml of tissue suspension. This preparation is used in subsequent binding assays with [$^3$H]oxytocin.

(b) Radioligand Binding

Binding of 3,5-[$^3$H]Oxytocin ([$^3$H]OT) to its receptors is done in microtiter plates using [$^3$H]OT, at various concentrations, in an assay buffer of 50.0 mM Tris.HCl, pH 7.4 and containing 5.0 mM $MgCl_2$, and a mixture of protease inhibitors: BSA, 0.1 mg; aprotinin, 1.0 mg; 1,10-phenanthroline, 2.0 mg; trypsin, 10.0 mg; and PMSF, 0.3 mg per 100 ml of buffer solution. Non-specific binding is determined in the presence of 1.0 uM unlabeled OT. The binding reaction is terminated after 60 minutes, at 22° C., by rapid filtration through glass fiber filters using a Brandel® cell harvester (Biomedical Research and Development Laboratories, Inc., Gaithersburg, Md.). Competition experiments are conducted at equilibrium using 1.0 nM [$^3$H]OT and varying the concentration of the displacing agents. The concentrations of agent displacing 50% of [$^3$H]OT at its sites ($IC_{50}$) are calculated by a computer assisted LUNDON-2 program (LUNDON SOFTWARE INC., Ohio, USA).

Binding Assay to Rat Hepatic $V_1$ Receptors and Rat Kidney Medullary $V_2$ Receptors or *Binding to $V_1$ Receptor Subtype in Human Platelet and **Binding to membranes of Mouse Fibroblast Cell Line (LV-2) Transfected with the cDNA Expressing the Human $V_2$ Receptor

TABLE I

| Ex. No. | Structure | $V_1$ IC$_{50}$(μM) | $V_2$ IC$_{50}$(μM) |
|---|---|---|---|
| 1 | 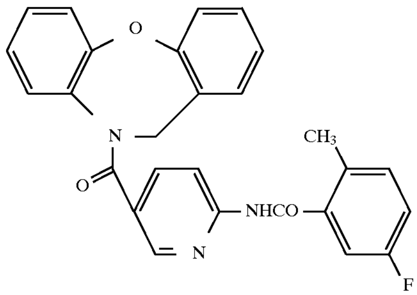 | 0.24 | 0.054 |
| 2 | 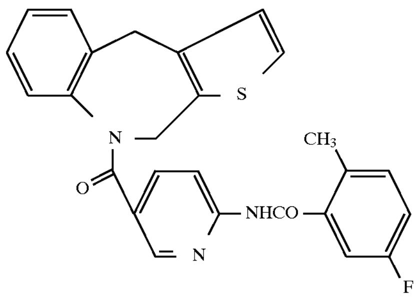 | 0.059 | 0.029 |
| 4 | 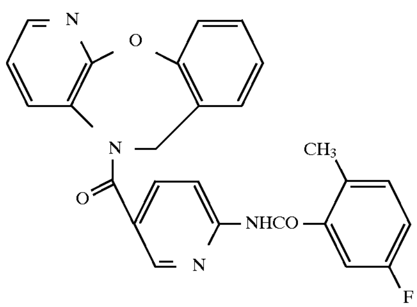 | 44% at 10 μM | 20% at 10 μM |
| 12 | 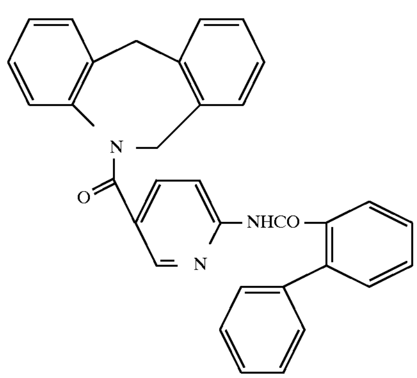 | 100% at 1 μM | 90% at μM |
| 24 | 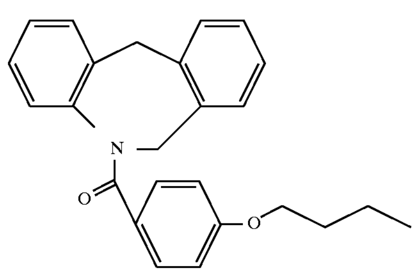 | *72% (μM) | **26% (10 μM) |

TABLE I-continued

| Ex. No. | Structure | $V_1$ IC$_{50}$(μM) | $V_2$ IC$_{50}$(μM) |
|---|---|---|---|
| 25 | 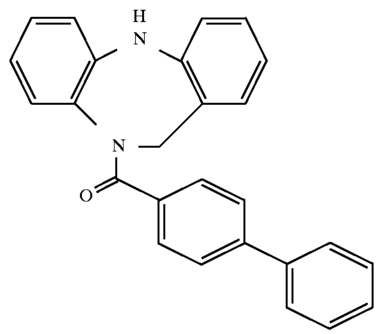 | 100% (1 μM) | 39% (1 μM) |
| 26 | 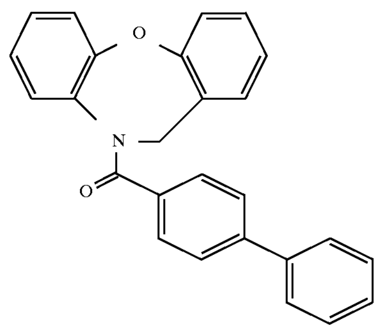 | 46% (1 μM) | 29% (10 μM) |
| 27 | 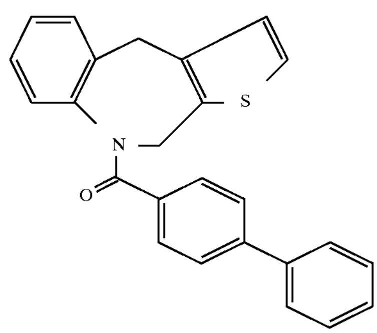 | *0.014 | **1.8 |
| 32 | 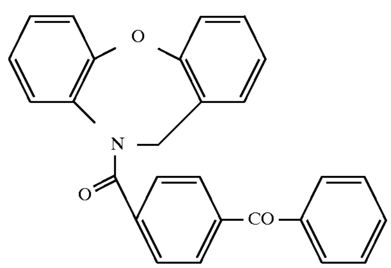 | 53% (10 μM) | 33% (10 μM) |
| 33 | 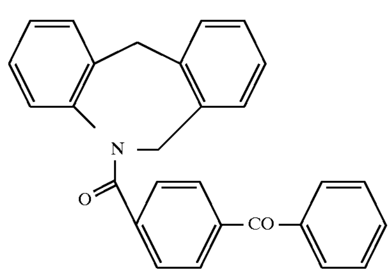 | 10% (10 μM) | 16% (10 μM) |

TABLE I-continued

| Ex. No. | Structure | $V_1$ $IC_{50}(\mu M)$ | $V_2$ $IC_{50}(\mu M)$ |
|---|---|---|---|
| 45 | (structure) | 34% (10 $\mu$M) | 62% (10 $\mu$M) |

TABLE II

Vasopressin $V_2$ Antagonist Activity In Conscious Hydrated Rats

| Ex. No. | Dose (mg/kg) | N | Urine Volume (ml/4 hrs) | Osmolality (MOsm/kg) |
|---|---|---|---|---|
| * | | 78 | 13.3 ± 0.3 | 229 ± 6 |
| ** | | 6 | 12.1 ± 1 | 497 ± 53 |
| | | 4 | 12.4 ± 0.8 | 361 ± 30 |
| *** | | 76 | 2 ± 0.2 | 1226 ± 58 |
| 26 | 10 | 2 | 4.5 | 1058 |
| 45 | 10 | 2 | 6.6 | 979 |
| 4 | 10 | 2 | 6.8 | 878 |
| 2 | 10 | 2 | 16.5 | 591 |
| 32 | 10 | 2 | 9.3 | 726 |
| 2 | 10 | 2 | 16.5 | 591 |
| 24 | 10 | 2 | 4.3 | 1492 |
| 27 | 10 | 2 | 3.3 | 1317 |

\* Water-load control
\*\* Water-load Control + DMSO (10%) (20%)
\*\*\* AVP-control Vasopressin Antidiuretic ($V_2$) Response in Conscious Rats with Free Access to Water Drinking Before But Not During the Experiment Male or female normotensive Sprague-Dawley rats (Charles River Laboratories, Inc., Kingston, N.Y.) of 400–450 g of body weight were supplied with Laboratory Rodent Feed #5001 (PMI Feeds, Inc., Richmond, Ind.) and water ad libitum. On the day of test, rats were placed individually into metabolic cages equipped with stainless steel screens (to separate the feces from the urine) and funnels for collection of urine. Compounds, vehicle, or reference agent was given at various oral doses. During the test, rats were provided with no water or food. After dosing, urine was collected in graduated cylinders for four hours. Urine volume was measured. Urinary osmolality was determined using a Fiske One-Ten Osmometer (Fiske Associates, Norwood, Mass. 02062). An aliquot of each urine collection was analyzed for $Na^+$, $K^+$ and $Cl^-$ using ion specific electrodes a in Beckman E3 (Electrolyte 3) analyzer. The vehicle used for testing compounds was 20% dimethylsulfoxide (DMSO) in 2.5% preboiled starch.

Table IV list results with compounds tested by this procedure.

TABLE IV

Vasopressin $V_2$ Antagonist Activity in Conscious Rats

| Ex. No. | Dose (mg/Kg) | N | Urine Volume (ml/4 hrs) | Osmolality (MOsm/kg) |
|---|---|---|---|---|
| * | | 16 | 7–10 ± 2 | 981 ± 34 |
| 47 | 10 | 2 | 22.0 | 394 |
| 66 | 10 | 2 | 17.0 | 442 |
| 67 | 10 | 2 | 21.5 | 402 |
| 134 | 10 | 2 | 40.5 | 333 |
| | 3 | 2 | 28 | 396 |
| | 1 | 2 | 18.2 | 596 |
| 133 | 10 | 2 | 27.5 | 234 |
| 135 | 10 | 2 | 39.5 | 284 |
| | 3 | 2 | 26.8 | 391 |
| | 1 | 2 | 19.5 | 526 |
| 176 | 10 | 2 | 12.8 | 567 |
| 218 | 10 | 2 | 34 | 222 |
| 257 | 10 | 2 | 22.5 | 317 |
| 301 | 10 | 2 | 41.5 | 363 |
| 302 | 10 | 2 | 40 | 356 |
| 352 | 10 | 2 | 9.3 | 779 |
| 396 | 10 | 2 | 21.8 | 238 |
| 397 | 10 | 2 | 29.8 | 288 |
| 398 | 10 | 2 | 20.5 | 316 |
| 399 | 10 | 2 | 17.0 | 404 |
| 400 | 10 | 2 | 24.8 | 270 |
| 404 | 10 | 2 | 6 | 909 |

\* Control DMSO (20%) - 2.5% corn starch

Compounds were dissolved in DMSO and then diluted in 2.5% corn starch (final concentration of DMSO was 20%). All rats were orally dosed with this mixture at 10 mV kg, by gavage.

TABLE III

Oxytocin Binding Assay

| Ex. No. | Dose ($\mu$M) | % Inhibition | $IC_{50}$ ($\mu$M) |
|---|---|---|---|
| 1 | 1 | 12 | — |
| 2 | 10 | 86 | 1.1 |
| 4 | 10 | 20 | — |
| 12 | 10 | 76 | 0.61 |
| 24 | 10 | 97 | 1.8 |
| 25 | 10 | 94 | 0.113 |
| 26 | 10 | 73 | 2.5 |
| 27 | 1 | 83 | — |
| 32 | 10 | 88 | 1.8 |
| 33 | 1 | 37 | — |
| 45 | 1 | 54 | — |

The compounds of the present invention can be used in the form of salts derived from pharmaceutically or physiologically acceptable acids or bases. These salts include, but are not limited to, the following: salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium or with organic bases. The compounds can also be used in the form of esters, carbamates and other conventional "pro-drug" forms, which, when administered in such form, convert to the active moiety in vivo.

When the compounds are employed for the above utilities, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The new tricyclic non-peptide vasopressin antagonists of this invention are useful in treating conditions where decreased vasopressin levels are desired, such as in congestive heart failure, in disease conditions with excess renal water reabsorption and in conditions with increased vascular resistance and coronary vasoconstriction.

In particular, the vasopressin antagonists of this invention are therapeutically useful in the treatment and/or prevention of hypertension, cardiac insufficiency, coronary vasospasm, cardiac ischemia, renal vasospasm, liver cirrhosis, congestive heart failure, nephritic syndrome, brain edema, cerebral ischemia, cerebral hemorrhage-stroke, thrombosis-bleeding and abnormal states of water retention.

In particular, the oxytocin antagonists of this invention are useful in the prevention of preterm labor and premature birth which is a significant cause of infant health problems and infant mortality.

We claim:

1. A compound selected from those of Formula I:

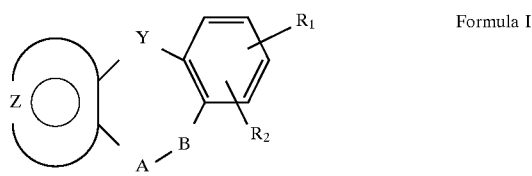

Formula I wherein Y is selected from NH, NCOCH$_3$, or N-lower alkyl (C$_1$–C$_3$);

A—B is selected from

R$_1$ is hydrogen, halogen (—Cl, —Br, —F, —I), —OH, —S-lower alkyl(C$_1$–C$_3$), —SH, —SO-lower alkyl (C$_1$–C$_3$), —SO$_2$-lower alkyl(C$_1$–C$_3$), —CO-lower alkyl(C$_1$–C$_3$), —CF$_3$, lower alkyl(C$_1$–C$_3$), —O-lower alkyl(C$_1$–C$_3$), —NO$_2$, —NH$_2$, —NHCO-lower alkyl (C$_1$–C$_3$), —N-[lower alkyl(C$_1$–C$_3$)]$_2$, —SO$_2$NH$_2$, —SO$_2$NH-lower alkyl (C$_1$–C$_3$), or —SO$_2$N[lower alkyl(C$_1$–C$_3$)]$_2$;

R$_2$ is hydrogen, —Cl, —Br, —F, —I, —OH, -lower alkyl(C$_1$–C$_3$), —O-lower alkyl(C$_1$–C$_3$), or R$_1$ and R$_2$ taken together are methylenedioxy or ethylenedioxy;

$R_3$ is the moiety

wherein Ar is a moiety selected from the group:

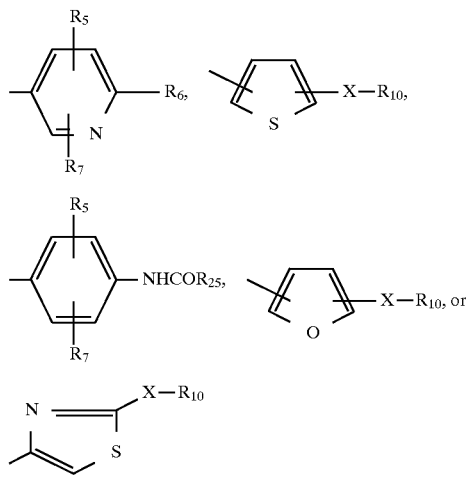

and X is O, S, —NCH$_3$ or —NH, —NCH$_3$,

or a chemical bond;

$R_5$ and $R_7$ are selected from the group of hydrogen, ($C_1$–$C_3$) lower alkyl, ($C_1$–$C_3$)lower alkoxy or halogen;

$R_6$ is selected from:

(a) moieties of the formula:

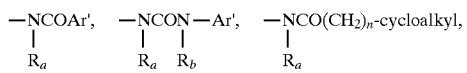

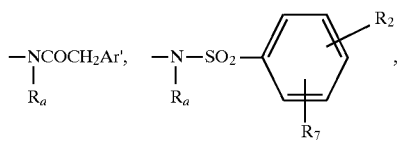

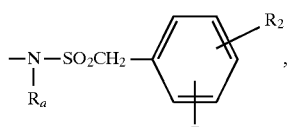

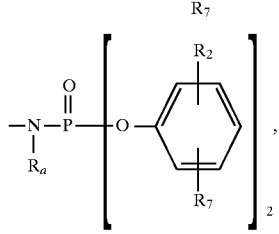

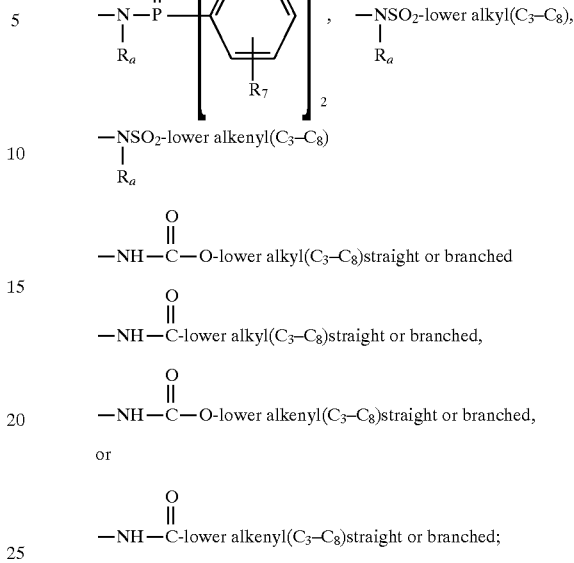

wherein cycloalkyl is defined as $C_3$ to $C_6$ cycloalkyl, cyclohexenyl or cyclopentenyl;

n is an integer from 0 to 2;

Ar' is selected from the group:

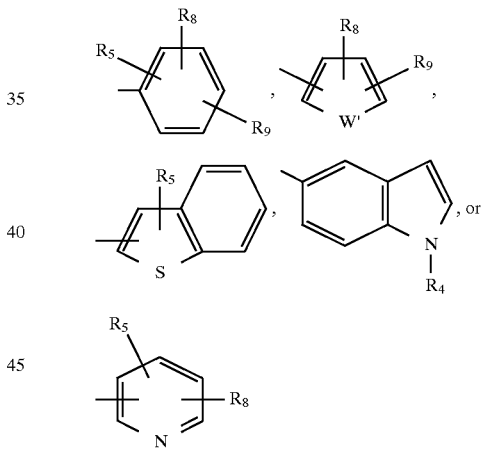

$R_a$ is hydrogen, CH$_3$, C$_2$H$_5$, moieties of the formulae:

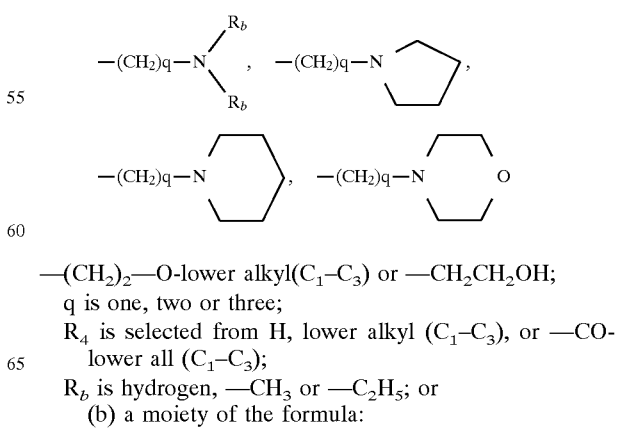

—(CH$_2$)$_2$—O-lower alkyl(C$_1$–C$_3$) or —CH$_2$CH$_2$OH;

q is one, two or three;

$R_4$ is selected from H, lower alkyl ($C_1$–$C_3$), or —CO-lower all ($C_1$–$C_3$);

$R_b$ is hydrogen, —CH$_3$ or —C$_2$H$_5$; or (b) a moiety of the formula:

—X—R$_{10}$ wherein

X is O, S, NH, NCH$_3$,

or a chemical bond;

R$_{10}$ is, lower alkenyl(C$_3$-C$_8$), —(CH$_2$)p-cycloalkyl (C$_3$-C$_6$),

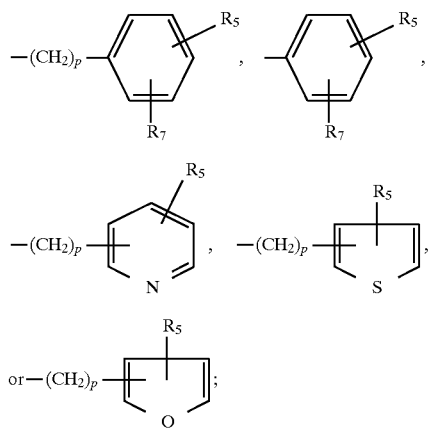

and p is zero to three;

and R$_5$ and R$_7$ are as previously defined; or
(c) a moiety of the formula:

wherein J is R$_a$, -lower alkyl (C$_3$-C$_8$) branched or unbranched, -lower alkenyl(C$_3$-C$_8$) branched or unbranched, —O-lower alkyl(C$_3$-C$_8$) branched or unbranched, —O-lower alkenyl(C$_3$-C$_8$) branched or unbranched, tetrahydrofuran, tetahydrothiophene, the moieties

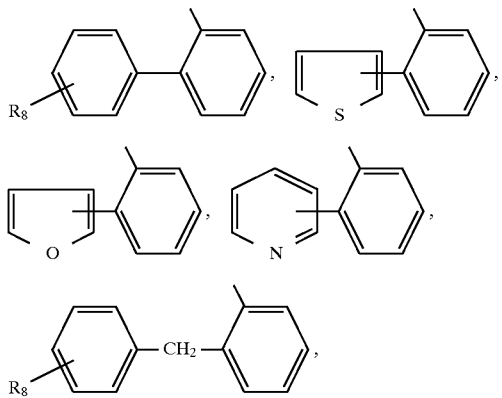

or —CH$_2$—K', wherein K' is halogen, —OH, tetrahydrofuran, tetrahydrothiophene or the heterocyclic ring moiety:

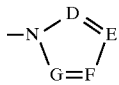

wherein D, E, F and G are selected from carbon or nitrogen and wherein the carbon atoms may be optionally substituted with halogen, (C$_1$-C$_3$) lower alkyl, hydroxy, —CO-lower alkyl(C$_1$-C$_3$), CHO, (C$_1$-C$_3$)lower alkoxy, —CO$_2$-lower alkyl(C$_1$-C$_3$), R$_8$ is selected from hydrogen, lower alkyl (C$_1$-C$_3$), —O-lower alkyl(C$_1$-C$_3$), —S-lower alkyl(C$_1$-C$_3$), —CF$_3$, —CN, —OH, —SCF$_3$, —OCF$_3$, halogen, —NO$_2$, amino, —NH-lower alkyl(C$_1$-C$_3$); —N-[lower alkyl(C$_1$-C$_3$)]$_2$, or —N(R$_b$)(CH$_2$)$_q$—N(R$_b$)$_2$;

R$_a$ and R$_b$ are as hereinbefore defined; or
(d) a moiety selected from those of the formulae:

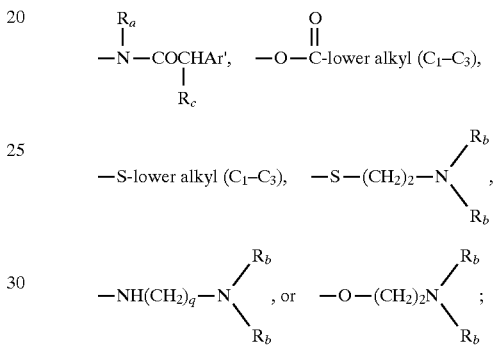

wherein R$_c$ is selected from halogen, (C$_1$-C$_3$)lower alkyl, —O-lower alkyl(C$_1$-C$_3$) and OH;

Ra and Rb are as hereinbefore defined;

q and Ar' are as defined above;

R$_8$ and R$_9$ are independently hydrogen, lower alkyl (C$_1$-C$_3$), —O-lower alkyl(C$_1$-C$_3$), —S-lower alkyl (C$_1$-C$_3$), —CF$_3$, —CN, —OH, —SCF$_3$, —OCF$_3$, halogen, —NO$_2$, amino, —NH-lower alkyl(C$_1$-C$_3$); —N-[lower alkyl(C$_1$-C$_3$)]$_2$, or —N(R$_b$)(CH$_2$)$_q$—N (R$_b$)$_2$;

W' is selected from O, S, NH N-lower alkyl (C$_1$-C$_3$), —NCO-lower alkyl(C$_1$-C$_3$), or NSO$_2$-lower alkyl (C$_1$-C$_3$);

R$_{25}$ is selected from the moieties

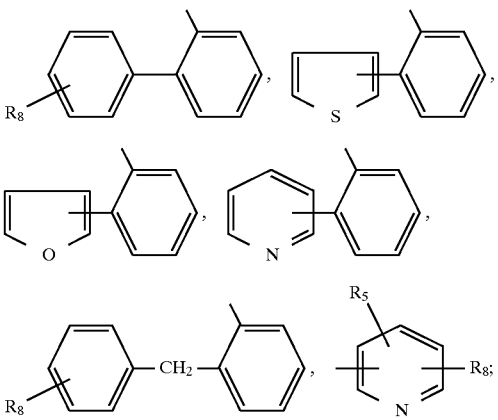

the moiety:

represents:

(1) phenyl or substituted phenyl optionally substituted by one or two substituents selected from $(C_1-C_3)$lower alkyl, halogen, amino, $(C_1-C_3)$lower alkoxy, or $(C_1-C_3)$lower alkylamino;

(2) a 5-membered aromatic (unsaturated) heterocyclic ring having one heteroatom selected from O, N or S;

(3) a 6-membered aromatic (unsaturated) heterocyclic ring having one nitrogen atom;

(4) a 5 or 6-membered aromatic (unsaturated) heterocyclic ring having two nitrogen atoms;

(5) a 5-membered aromatic (unsaturated) heterocyclic ring having one nitrogen atom together with either one oxygen or one sulfur atom;

wherein the 5 or 6-membered heterocyclic rings are optionally substituted by $(C_1-C_3)$lower alkyl, formyl, a moiety of the formula:

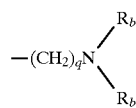

halogen or $(C_1-C_3)$lower alkoxy;

wherein q and $R_b$ are as hereinbefore defined;

and the pharmaceutically acceptable salts thereof.

2. A compound of claim 1 wherein the moiety:

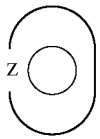

represents phenyl or substituted phenyl optionally substituted by one or two substituents selected from $(C_1-C_3)$lower alkyl, halogen, amino, $(C_1-C_3)$lower alkoxy, or $(C_1-C_3)$ lower alkylamino or a pharmaceutically acceptable salt thereof.

3. A compound of claim 1 wherein the moiety:

presents a 5-membered aromatic (unsaturated) heterocyclic ring having one heteroatom selected from O, N or S, the heterocyclic ring being optionally substituted by $(C_1-C_3)$ lower alkyl, formyl, a moiety of the formula:

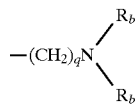

halogen or $(C_1-C_3)$lower alkoxy;

wherein q and $R_b$ are as defined in claim 1;

or a pharmaceutically acceptable salt thereof.

4. A compound of claim 1 wherein the moiety:

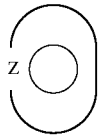

represents a 6-membered aromatic (unsaturated) heterocyclic ring having one nitrogen atom, the heterocyclic ring being optionally substituted by $(C_1-C_3)$lower alkyl, formyl, a moiety of the formula:

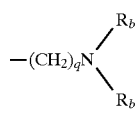

halogen or $(C_1-C_3)$lower alkoxy;

wherein q and $R_b$ are as defined in claim 1;

or a pharmaceutically acceptable salt thereof.

5. A compound of claim 1 wherein the moiety:

represents a 5 or 6-membered aromatic (unsaturated) heterocyclic ring having two nitrogen atoms, the heterocyclic ring being optionally substituted by $(C_1-C_3)$lower alkyl, formyl, a moiety of the formula:

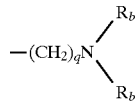

halogen or $(C_1-C_3)$lower alkoxy;

wherein q and $R_b$ are as defined in claim 1;

or a pharmaceutically acceptable salt thereof.

6. A compound of claim 1 wherein the moiety:

represents a 5-membered aromatic (unsaturated) heterocyclic ring having one nitrogen atom together with either one oxygen or one sulfur atom, the heterocyclic ring being optionally substituted by $(C_1-C_3)$lower alkyl, formyl, a moiety of the formula:

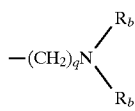

halogen or (C$_1$–C$_3$)lower alkoxy;

wherein q and R$_b$ are as defined in claim 1;

or a pharmaceutically acceptable salt thereof.

7. A compound of claim 1 having the formula:

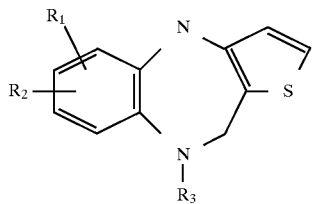

wherein R$_3$ is the moiety:

Ar is selected from the moieties:

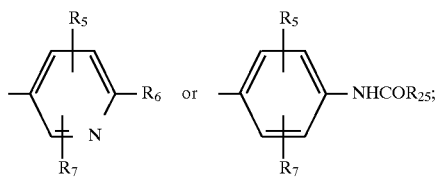

and R$_1$, R$_2$, R$_3$, R$_5$, R$_6$, R$_7$ and R$_{25}$ are as defined in claim 1;

or a pharmaceutically acceptable salt thereof.

8. A pharmaceutical composition useful for treating diseases characterized by excess renal reabsorption of water as well as congestive heart failure, liver cirrhosis, nephrotic syndrome, central nervous system injuries, lung disease and hyponatremia in a mammal comprising a suitable pharmaceutical carrier and an effective amount of a compound of claim 1.

9. A method of treating diseases characterized by excess renal reabsorption of water as well as congestive heart failure, liver cirrhosis, nephrotic syndrome, central nervous system injuries, lung disease and hyponatremia in a mammal comprising administering a compound of claim 1 to said mammal in an amount effective to alleviate the disease.

10. A compound selected from Formula I:

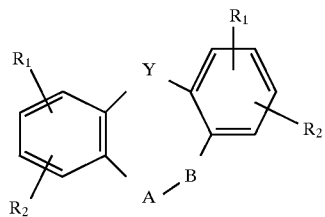

wherein;

Y is selected from NH or

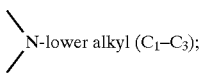

A—B is

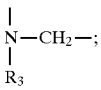

R$_1$ is H, halogen (chlorine, fluorine, bromine, iodine), OH, —S-lower alkyl (C$_1$–C$_3$), —SH, —SO-lower allyl (C$_1$–C$_3$), —SO$_2$-lower alkyl (C$_1$–C$_3$), —CO-lower alkyl (C$_1$–C$_3$), —CHF$_3$, lower alkyl (C$_1$–C$_3$), —O-lower alkyl (C$_1$–C$_3$), —NO$_2$, —NH$_2$, —NHCO-lower alkyl (C$_1$–C$_3$), —N-[lower alkyl (C$_1$–C$_3$)]$_2$, SO$_2$NH$_2$, —SO$_2$NH-lower alkyl (C$_1$–C$_3$), or —SO$_2$N [lower alkyl (C$_1$–C$_3$)]$_2$;

R$_2$ is H, Cl, Br, I, F, —OH, lower allyl (C$_1$–C$_3$), —O-lower alkyl (C$_1$–C$_3$); or R$_1$ and R$_2$ taken together are methylenedioxy or ethylenedioxy;

R$_3$ is the moiety

wherein Ar is a moiety selected from the group

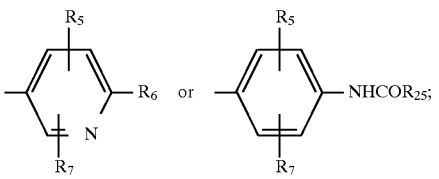

R$_5$ and R$_7$ are independently selected from H, lower alkyl (C$_1$–C$_3$), lower alkoxy (C$_1$–C$_3$), or halogen;

R$_6$ is selected from:

(a) the moieties of the formulae:

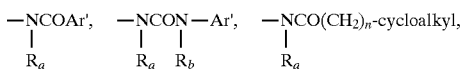

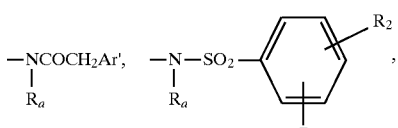

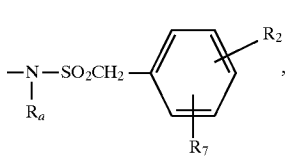

-continued

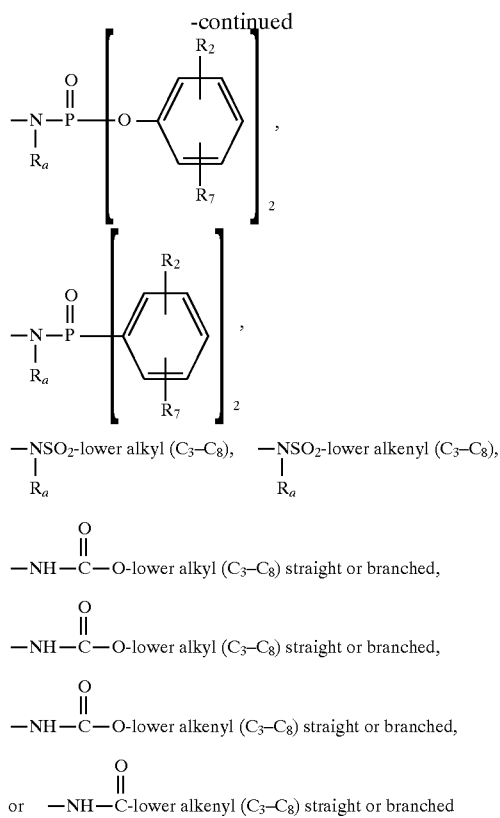

—NSO₂-lower alkyl (C₃–C₈),  —NSO₂-lower alkenyl (C₃–C₈),
    |                           |
    R_a                         R_a

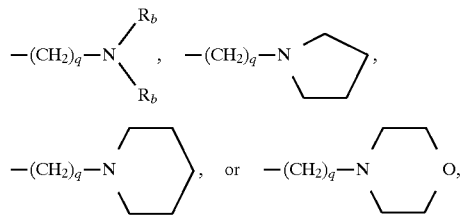

or —NH—C(=O)-lower alkenyl (C₃–C₈) straight or branched wherein n is 0–2;

cycloalkyl is defined as $C_3$–$C_6$ cycloalkyl, cyclohexenyl or cyclopentenyl;

$R_a$ is hydrogen, $CH_3$, $C_2H_5$, moieties of the formulae:

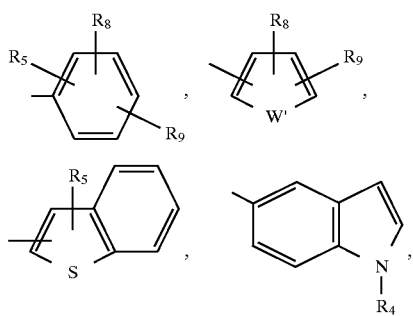

—$(CH_2)_2$—O-lower alkyl ($C_1$–$C_3$) or —$CH_2CH_2OH$;

q is one, two or three;

$R_b$ is hydrogen, —$CH_3$ or —$C_2H_5$;

Ar' is selected from the group:

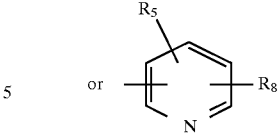

-continued

$R_4$ is selected from H, lower alkyl ($C_1$–$C_3$), or —CO-lower alkyl ($C_1$–$C_3$);

$R_8$ and $R_9$ are independently hydrogen, lower alkyl ($C_1$–$C_3$), —O-lower alkyl ($C_1$–$C_3$), S-lower alkyl ($C_1$–$C_3$), —$CF_3$, —CN, —OH, —$SCF_3$, —$OCF_3$, halogen, $NO_2$, amino, —NH-lower alkyl ($C_1$–$C_3$), —N-[lower alkyl ($C_1$–$C_3$)]$_2$, or —N($R_b$)($CH_2$)$_q$—N($R_b$)$_2$;

W' is selected from O, S, NH, N-lower alkyl ($C_1$–$C_3$), —NCO-lower alkyl ($C_1$–$C_3$), or NSO$_2$-lower alkyl ($C_1$–$C_3$);

(b) a moiety of the formula:

—X—$R_{10}$ wherein:

X is a bond, O, S, NH,

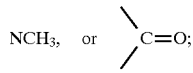

$R_{10}$ is selected from the group of lower alkyl ($C_3$–$C_8$), lower alkenyl ($C_3$–$C_8$), —$(CH_2)_p$-cycloalkyl ($C_3$–$C_6$),

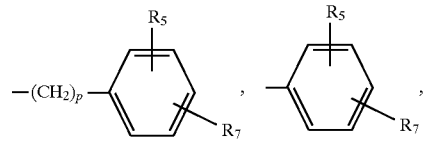

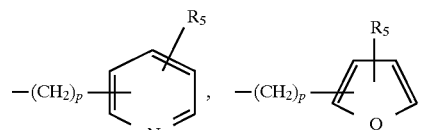

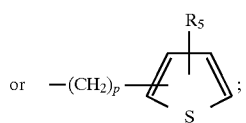

p is an integer from 0 to 3;

$R_5$ and $R_7$ are independently selected from H, lower alkyl ($C_1$–$C_3$), lower alkoxy ($C_1$–$C_3$), or halogen;

(c) a moiety of the formula:

wherein

J is $R_a$, lower alkyl ($C_1$–$C_8$) branched or unbranched, lower alkenyl ($C_2$–$C_8$) branched or unbranched, —O-lower alkyl ($C_1$–$C_8$) branched or unbranched, —O-lower alkenyl ($C_2$–$C_8$) branched or unbranched, tetrahydrofuran, tetrahydrothiophene, the moieties:

143

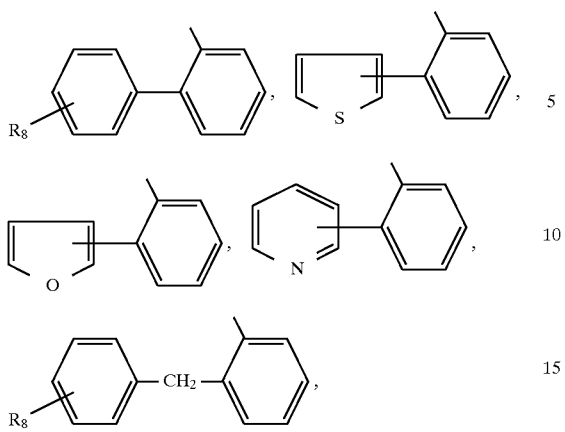

or —CH₂—K' wherein K is halogen, —OH, tetrahydrofuran, tetrahydrothiophene or the heterocyclic ring moiety:

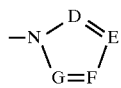

wherein D, E, F and G are selected from carbon or nitrogen and wherein the carbon atoms may be optionally substituted with halogen, ($C_1$–$C_3$)lower alkyl, hydroxy, —CO-lower alkyl ($C_1$–$C_3$), CHO, ($C_1$–$C_3$)lower alkoxy, or —CO₂-lower alkyl ($C_1$–$C_3$);

$R_8$, $R_a$ and $R_b$ are as hereinbefore defined; or (d) a moiety selected from those of the formulae:

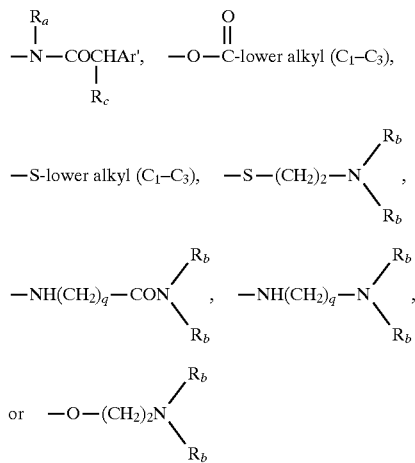

$R_c$ is selected from halogen, ($C_1$–$C_3$) lower alkyl, —O-lower alkyl ($C_1$–$C_3$) or OH;

$R_a$, $R_b$, q, Ar', $R_4$, $R_8$, $R_9$ and W' are as described above;

$R_{25}$ is selected from the moieties:

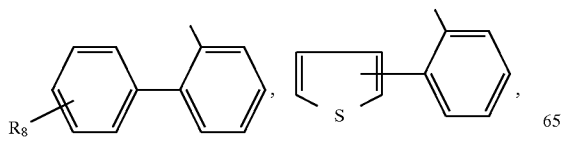

144

-continued

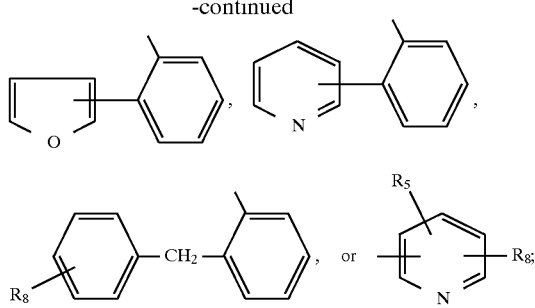

or a pharmaceutically acceptable salt thereof.

11. The compound according to claim 9, N-[4-[(5,11-dihydro-10H-dibenz[b,e][1,4]diazepin-10-yl)carbonyl]-3-chlorophenyl][1,1'-biphenyl]-2-carboxamide.

12. The compound according to claim 9, N-[4-[(5,11-dihydro-10H-dibenz[b,e][1,4]diazepin-10-yl)carbonyl]-phenyl][1,1'-biphenyl]-2-carboxamide.

13. The compound according to claim 9, N-[4-[(5,11-dihydro-10H-dibenz[b,e][1,4]diazepin-10-yl)carbonyl]-3-methylphenyl][1,1'-biphenyl]-2-carboxamide.

14. The compound according to claim 9, N-[4-[(5,11-dihydro-10H-dibenz[b,e][1,4]diazepin-10-yl)carbonyl]-2-methylphenyl][1,1'-biphenyl]-2-carboxamide.

15. The compound according to claim 9, N-[4-[(5,11-dihydro-10H-dibenz[b,e][1,4]diazepin-10-yl)carbonyl]-2-chlorophenyl][1,1'-biphenyl]-2-carboxamide.

16. A pharmaceutical composition useful for treating diseases characterized by excess renal reabsorption of water as well as congestive heart failure, liver cirrhosis, nephrotic syndrome, central nervous system injuries, lung disease and hyponatremia in a mammal comprising a suitable pharmaceutical carrier and an effective amount of a compound of claim 9.

17. A method of treating diseases characterized by excess renal reabsorption of water as well as congestive heart failure, liver cirrhosis, nephrotic syndrome, central nervous system injuries, lung disease and hyponatremia in a mammal comprising administering a compound of claim 9 to said mammal in an amount effective to alleviate the disease.

18. The compound according to claim 9, 5,11-dihydro-10-[4-(2-thienyl)benzoyl]-10H-dibenz[b,e][1,4]diazepine.

19. The compound according to claim 9, 5,11-dihydro-10-[4-(3-thienyl)benzoyl]-10H-dibenz[b,e][1,4]diazepine.

20. A compound selected from those of Formula I:

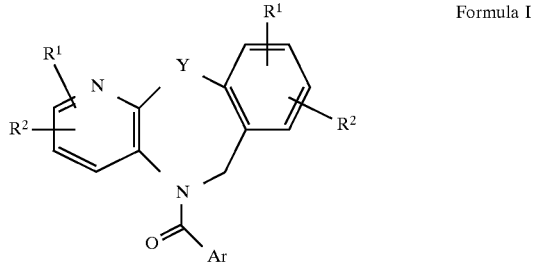

Formula I wherein:

Y is selected from NH, NCOCH₃, or N-lower alkyl ($C_1$–$C_3$);

$R_1$ is hydrogen, halogen (—Cl, —Br, —F, —I), —OH, —S-lower alkyl($C_1$–$C_3$), —SH, —SO-lower alkyl ($C_1$–$C_3$), —SO₂-lower alkyl($C_1$–$C_3$), —CO-lower alkyl($C_1$–$C_3$), —CF₃, lower alkyl($C_1$–$C_3$), —O-lower alkyl($C_1$–$C_3$), —NO₂, —NH₂, —NHCO-lower alkyl ($C_1$–$C_3$), —N-[lower alkyl($C_1$–$C_3$)]$_2$, —SO$_2$NH$_2$, —SO$_2$NH-lower alkyl ($C_1$–$C_3$), or —SO$_2$N[lower alkyl($C_1$–$C_3$)]$_2$;

$R_2$ is hydrogen, —Cl, —Br, —F, —I, —OH, -lower alkyl($C_1$–$C_3$), —O-lower alkyl($C_1$–$C_3$), or $R_1$ and $R_2$ taken together are methylenedioxy or ethylenedioxy;

Ar is selected from the moieties:

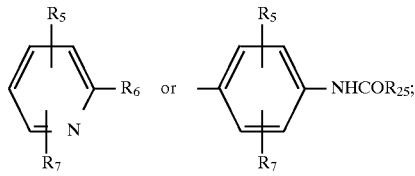

$R_5$ and $R_7$ are independently selected from H, lower alkyl ($C_1$–$C_3$), lower alkoxy ($C_1$–$C_3$), or halogen;

$R_6$ is selected from:
(a) the moieties of the formulae:

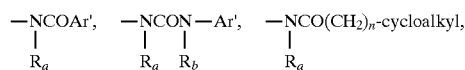

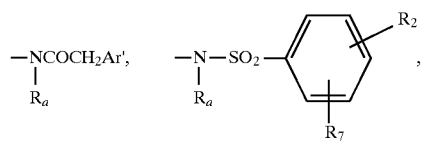

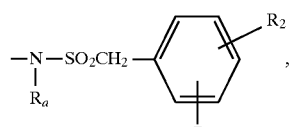

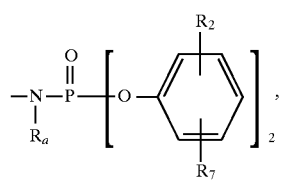

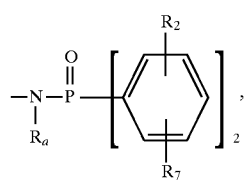

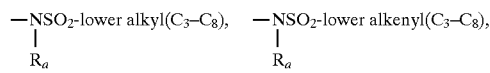

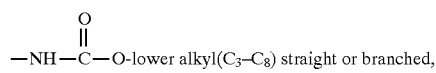

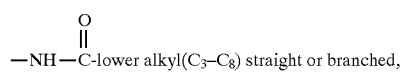

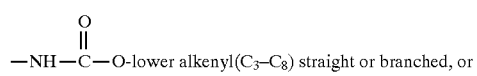

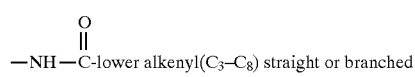

wherein
n is 0–2, cycloalkyl is defined as $C_3$–$C_6$ cycloalkyl, cyclohexenyl or cyclopentenyl;

$R_a$ is hydrogen, CH$_3$, C$_2$H$_5$, moieties of the formulae:

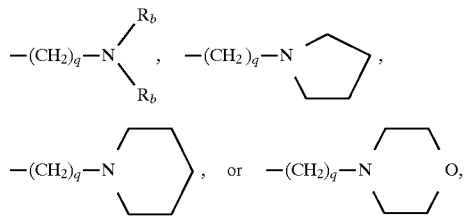

—(CH$_2$)$_2$-O-lower alkyl ($C_1$–$C_3$) or —CH$_2$CH$_2$OH;

q is one, two or three;

$R_b$ is hydrogen, —CH$_3$ or —C$_2$H$_5$;

Ar' is selected from the group:

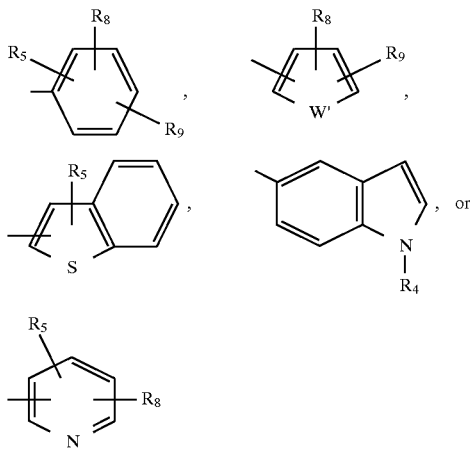

$R_4$ is selected from H, lower alkyl ($C_1$–$C_3$), or —CO-lower alkyl ($C_1$–$C_3$);

$R_5$ and $R_7$ are independently selected from H, lower alkyl ($C_1$–$C_3$), lower alkoxy ($C_1$—$C_3$), or halogen;

$R_8$ and $R_9$ are independently hydrogen, lower alkyl ($C_1$–$C_3$), —O-lower alkyl ($C_1$–$C_3$), S-lower alkyl ($C_1$–$C_3$), —CF$_3$, —CN, —OH, —SCF$_3$, —OCF$_3$, halogen, NO$_2$, amino, —NH-lower alkyl ($C_1$–$C_3$), —N-[lower alkyl ($C_1$–$C_3$)]$_2$, or —N($R_b$)(CH$_2$)$_q$—N ($R_b$)$_2$;

W' is selected from O, S, NH, N-lower alkyl ($C_1$–$C_3$), —NCO-lower alkyl ($C_1$–$C_3$), or NSO$_2$-lower allyl ($C_1$–$C_3$); or (b) a moiety of the formula:

—X—$R_{10}$ 

wherein:

X is a bond, O, S, NH, NCH$_3$, or

$R_{10}$ is selected from the group of lower alkyl ($C_3$–$C_8$), lower alkenyl ($C_3$–$C_8$), —(CH$_2$)$_p$-cycloalkyl ($C_3$–$C_6$),

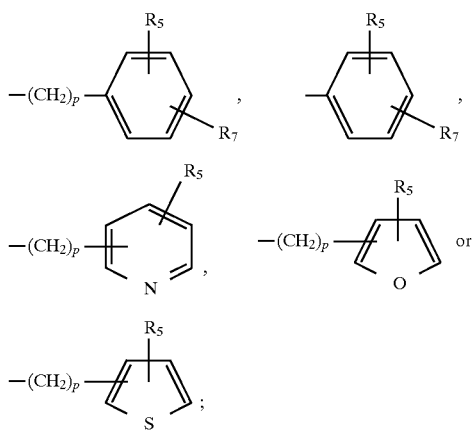

p is an integer from 0 to 3;
R$_5$ and R$_7$ are as defined above; or
(c) a moiety of the formula:

wherein

J is R$_a$, lower alkyl (C$_1$–C$_8$) branched or unbranched, lower alkenyl (C$_2$–C$_8$) branched or unbranched, —O-lower alkyl (C$_1$–C$_8$) branched or unbranched, —O-lower alkenyl (C$_2$–C$_8$) branched or unbranched, tetrahydrofuran, tetrahydrothiophene, the moieties:

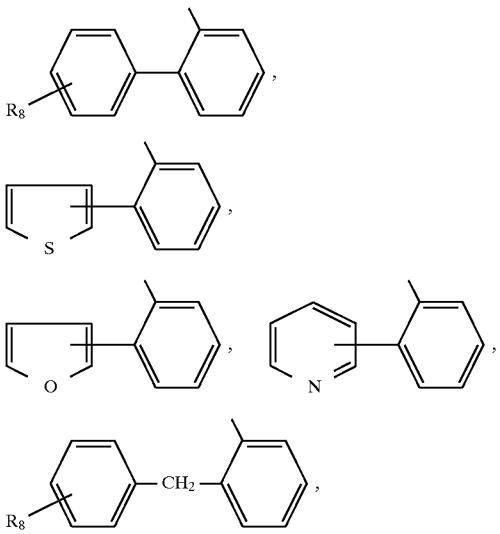

or —CH$_2$—K' wherein K is halogen, —OH, tetrahydrofuran, tetrahydrothiophene or the heterocyclic ring moiety:

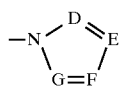

wherein D, E, F and G are selected from carbon or nitrogen and wherein the carbon atoms may be optionally substituted with halogen, (C$_1$–C$_3$) lower alkyl, hydroxy, —CO-lower alkyl (C$_1$–C$_3$), CHO, (C$_1$–C$_3$) lower alkoxy, or —CO$_2$-lower alkyl (C$_1$–C$_3$);

R$_8$, R$_a$ and R$_b$ are as hereinbefore defined; or (d) a moiety selected from those of the formulae:

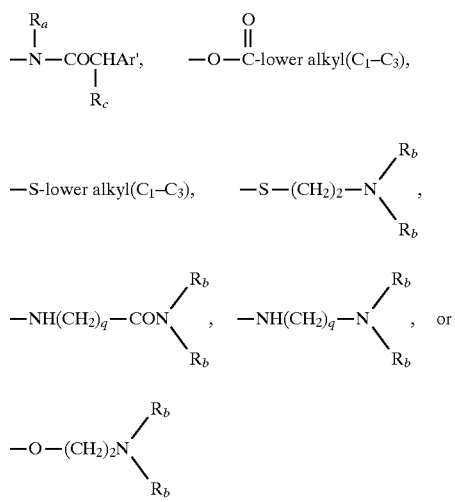

R$_c$ is selected from halogen, (C$_1$–C$_3$) lower alkyl, —O-lower alkyl (C$_1$–C$_3$) or OH;

R$_b$, q, Ar', R$_4$, R$_8$, R$_9$ and W' are as defined above;

R$_{25}$ is selected from the moieties:

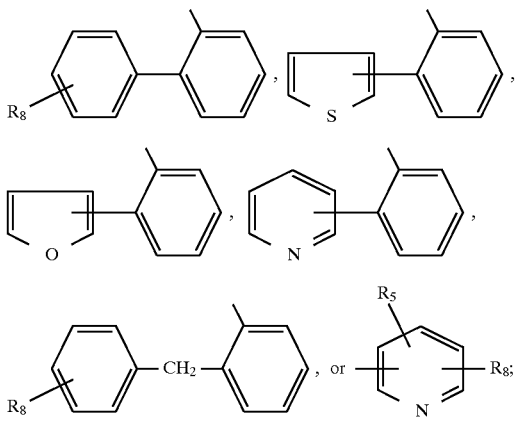

or a pharmaceutically acceptable salt thereof.

21. A pharmaceutical composition useful for treating diseases characterized by excess renal reabsorption of water as well as congestive heart failure, liver cirrhosis, nephrotic syndrome, central nervous system injuries, lung disease and hyponatremia in a mammal comprising a suitable pharmaceutical carrier and an effective amount of a compound of claim 20.

22. A method of treating diseases characterized by excess renal reabsorption of water as well as congestive heart failure, liver cirrhosis, nephrotic syndrome, central nervous system injuries, lung disease and hyponatremia in a mammal comprising administering a compound of claim 20 to said mammal in an amount effective to alleviate the disease.

23. A compound selected from those of Formula I:

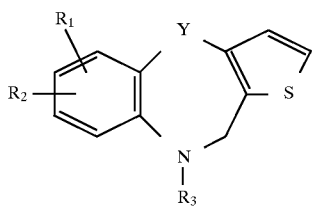

Formula I wherein:

Y is selected from NH or N-lower alkyl ($C_1$–$C_3$);

$R_1$ is hydrogen, halogen (—Cl, —Br, —F, —I), —OH, —S-lower alkyl($C_1$–$C_3$), —SH, —SO-lower alkyl ($C_1$–$C_3$), —$SO_2$-lower alkyl($C_1$–$C_3$), —CO-lower alkyl($C_1$–$C_3$), —$CF_3$, lower alkyl($C_1$–$C_3$), —O-lower alkyl($C_1$–$C_3$), —$NO_2$, —$NH_2$, —NHCO-lower alkyl ($C_1$–$C_3$), —N-[lower alkyl($C_1$–$C_3$)]$_2$, —$SO_2NH_2$, —$SO_2$NH-lower alkyl ($C_1$–$C_3$), or —$SO_2$N[lower alkyl($C_1$–$C_3$)]$_2$;

$R_2$ is hydrogen, —Cl, —Br, —F, —I, —OH, -lower alkyl($C_1$–$C_3$), —O-lower alkyl($C_1$–$C_3$), or $R_1$ and $R_2$ taken together are methylenedioxy or ethylenedioxy;

$R_3$ is the moiety:

Ar is selected from the moieties:

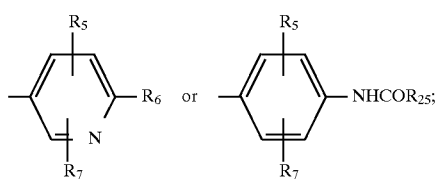

$R_5$ and $R_7$ are independently selected from H, lower alkyl ($C_1$–$C_3$), lower alkoxy ($C_1$–$C_3$), or halogen;

$R_6$ is selected from (a) the moieties of the formulae:

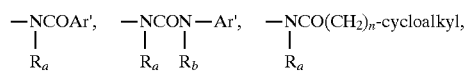

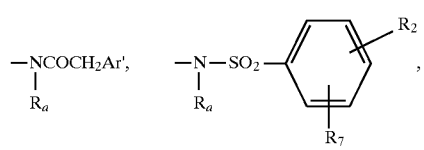

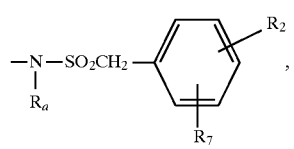

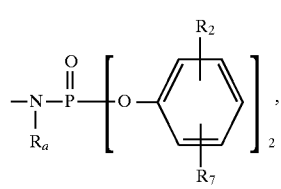

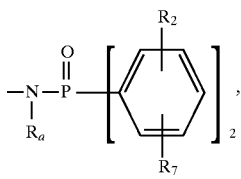

—$NSO_2$-lower alkyl($C_3$–$C_8$), —$NSO_2$-lower alkenyl($C_3$–$C_8$),
|
$R_a$

—NH—C(=O)—O-lower alkyl($C_3$–$C_8$) straight or branched,

—NH—C(=O)-lower alkyl($C_3$–$C_8$) straight or branched,

—NH—C(=O)—O-lower alkenyl($C_3$–$C_8$) straight or branched, or

—NH—C(=O)-lower alkenyl($C_3$–$C_8$) straight or branched wherein n is 0–2;

cycloalkyl is defined as $C_3$–$C_6$ cycloalkyl, cyclohexenyl or cyclopentenyl;

$R_a$ is hydrogen, $CH_3$, $C_2H_5$, moieties of the formulae:

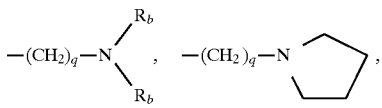

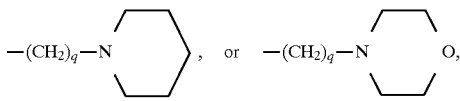

—$(CH_2)_2$—O-lower alkyl ($C_1$–$C_3$) or —$CH_2CH_2OH$;

q is one, two or three;

$R_b$ is hydrogen, —$CH_3$ or —$C_2H_5$;

Ar' is selected from the group;

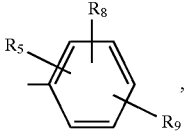 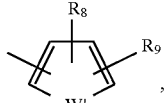

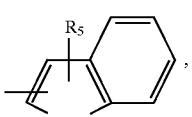 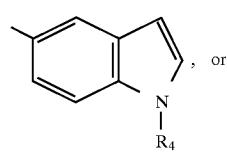

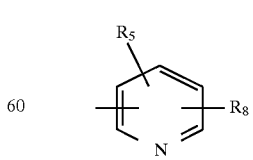

$R_4$ is selected from H, lower alkyl ($C_1$–$C_3$), or —CO-lower alkyl ($C_1$–$C_3$);

$R_8$ and $R_9$ are independently hydrogen, lower alkyl ($C_1$–$C_3$), —O-lower alkyl ($C_1$–$C_3$), S-lower alkyl ($C_1$–$C_3$), —$CF_3$, —CN, —OH, —$SCF_3$, —$OCF_3$, halogen, $NO_2$, amino, —NH-lower alkyl ($C_1$–$C_3$), —N-[lower alkyl ($C_1$–$C_3$)]$_2$, or —N($R_b$)($CH_2$)$_q$—N($R_b$)$_2$;

W' is selected from O, S, NH, N-lower alkyl ($C_1$–$C_3$), —NCO-lower alkyl ($C_1$–$C_3$), or $NSO_2$-lower alkyl ($C_1$–$C_3$); or (b) a moiety of the formula:

wherein:

X is a bond, O, S, NH,

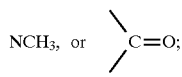

$R_{10}$ is selected from the group of lower alkyl ($C_3$–$C_8$), lower alkenyl ($C_3$–$C_8$), —($CH_2$)-cycloalkyl ($C_3$–$C_6$),

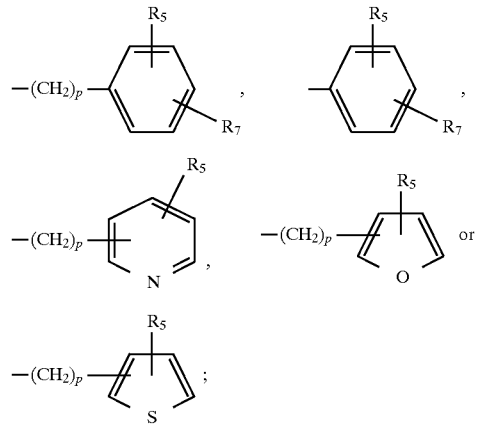

p is an integer from 0 to 3;

$R_5$ and $R_7$ are independently selected from H, lower alkyl ($C_1$–$C_3$), lower alkoxy ($C_1$–$C_3$), or halogen; or (c) a moiety of the formula:

wherein

J is $R_a$, lower alkyl ($C_1$–$C_8$) branched or unbranched, lower alkenyl ($C_2$–$C_8$) branched or unbranched, —O-lower alkyl ($C_1$–$C_8$) branched or unbranched, —O-lower alkenyl ($C_2$–$C_8$) branched or unbranched, tetrahydrofuran, tetrahydrothiophene, the moieties:

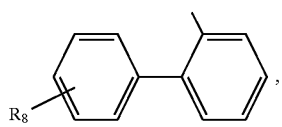

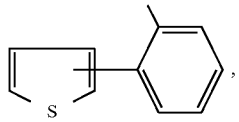

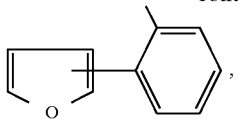

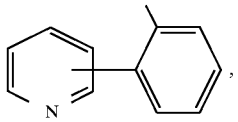

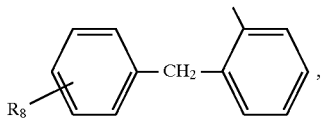

or —$CH_2$—K' wherein K is halogen, —OH, tetrahydrofuran, tehydrothiophene or the heterocyclic ring moiety:

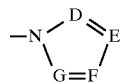

wherein D, E, F and G are selected from carbon or nitrogen and wherein the carbon atoms may be optionally substituted with halogen, ($C_1$–$C_3$)lower alkyl, hydroxy, —CO-lower alkyl ($C_1$–$C_3$), CHO, ($C_1$–$C_3$)lower alkoxy, or —$CO_2$-lower alkyl ($C_1$–$C_3$);

$R_8$, $R_a$ and $R_b$ are as hereinbefore defined; or (d) a moiety selected from those of the formulae:

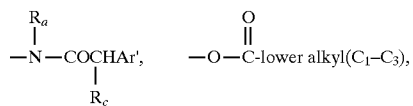

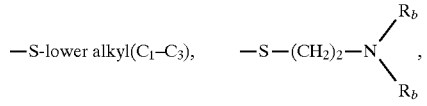

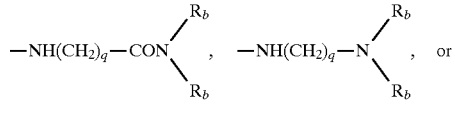

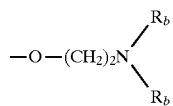

$R_c$ is selected from halogen, ($C_1$–$C_3$) lower alkyl, —O-lower alkyl ($C_1$–$C_3$) or OH;

$R_b$, q, Ar', $R_4$, $R_8$, $R_9$ and W' are as defined above;

$R_{25}$ is selected from the moieties:

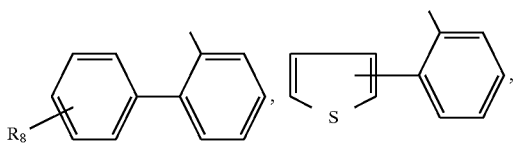

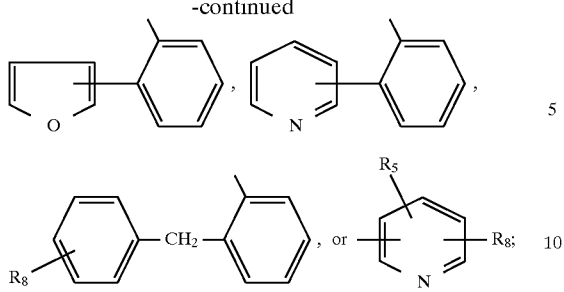

or a pharmaceutically acceptable salt thereof.

24. A pharmaceutical composition useful for treating diseases characterized by excess renal reabsorption of water as well as congestive heart failure, liver cirrhosis, nephrotic syndrome, central nervous system injuries, lung disease and hyponatremia in a mammal comprising a suitable pharmaceutical carrier and an effective amount of a compound of claim 23.

25. A method of treating diseases characterized by excess renal reabsorption of water as well as congestive heart failure, liver cirrhosis, nephrotic syndrome, central nervous system injuries, lung disease and hyponatremia in a mammal comprising administering a compound of claim 23 to said mammal in an amount effective to alleviate the disease.

26. A compound selected from those of Formula I:

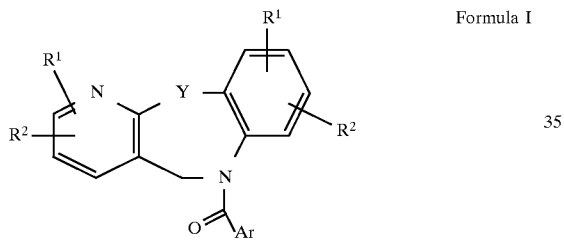

Formula I wherein:

Y is selected from NH;

$R_1$ is hydrogen, halogen (—Cl, —Br, —F, —I), —OH, —S-lower alkyl($C_1$–$C_3$), —SH, —SO-lower alkyl ($C_1$–$C_3$), —$SO_2$-lower alkyl($C_1$–$C_3$), —CO-lower alkyl($C_1$–$C_3$), —$CF_3$, lower alkyl($C_1$–$C_3$), —O-lower alkyl($C_1$–$C_3$), —$NO_2$, —$NH_2$, —NHCO-lower alkyl ($C_1$–$C_3$), —N-[lower alkyl($C_1$–$C_3$)]$_2$, —$SO_2NH_2$, —$SO_2$NH-lower alkyl ($C_1$–$C_3$), or —$SO_2$N[lower alkyl($C_1$–$C_3$)]$_2$;

$R_2$ is hydrogen, —Cl, —Br, —F, —I, —OH, -lower alkyl($C_1$–$C_3$), —O-lower alkyl($C_1$–$C_3$), or $R_1$ and $R_2$ taken together are methylenedioxy or ethylenedioxy;

Ar is selected from the moieties:

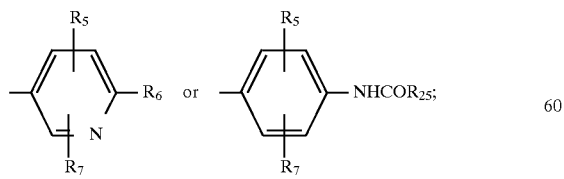

$R_5$ and $R_7$ are independently selected from H, lower alkyl ($C_1$–$C_3$), lower alkoxy ($C_1$–$C_3$), or halogen;

$R_6$ is selected from (a) the moieties of the formulae:

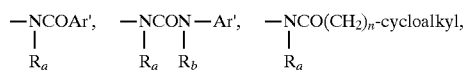

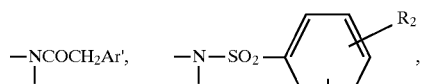

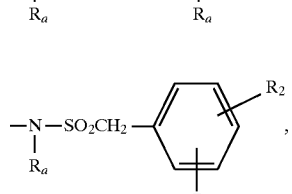

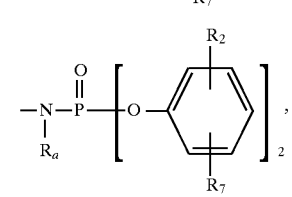

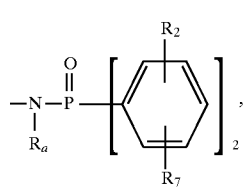

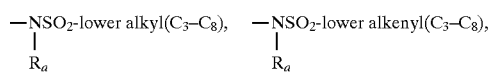

$$-NH-\overset{O}{\underset{\|}{C}}-O\text{-lower alkyl}(C_3-C_8) \text{ straight or branched,}$$

$$-NH-\overset{O}{\underset{\|}{C}}\text{-lower alkyl}(C_3-C_8) \text{ straight or branched,}$$

$$-NH-\overset{O}{\underset{\|}{C}}-O\text{-lower alkenyl}(C_3-C_8) \text{ straight or branched, or}$$

$$-NH-\overset{O}{\underset{\|}{C}}\text{-lower alkenyl}(C_3-C_8) \text{ straight or branched}$$

wherein n is 0—2;

cycloalkyl is defined as $C_3$–$C_6$ cycloalkyl, cyclohexenyl or cyclopentenyl;

$R_a$ is hydrogen, $CH_3$, $C_2H_5$, moieties of the formulae:

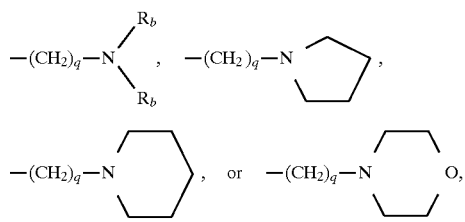

—$(CH_2)_2$—O-lower alkyl ($C_1$–$C_3$) or —$CH_2CH_2OH$;

q is one, two or three;

$R_b$ is hydrogen, —$CH_3$ or —$C_2H_5$;

Ar' is selected from the group:

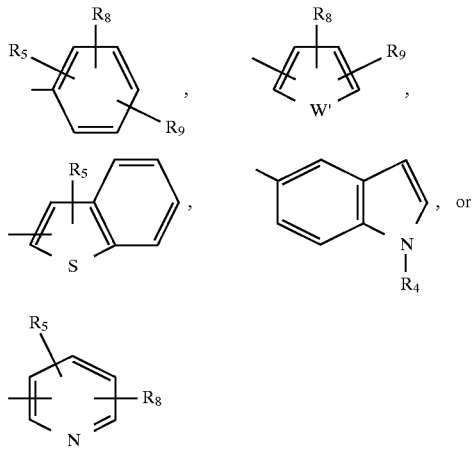

$R_4$ is selected from H, lower alkyl ($C_1$–$C_3$), or —CO-lower alkyl ($C_1$–$C_3$);

$R_8$ and $R_9$ are independently hydrogen, lower alkyl ($C_1$–$C_3$), —O-lower alkyl ($C_1$–$C_3$), S-lower alkyl ($C_1$–$C_3$), —$CF_3$, —CN, —OH, —$SCF_3$, —$OCF_3$, halogen, $NO_2$, amino, —NH-lower alkyl ($C_1$–$C_3$), —N-[lower alkyl ($C_1$–$C_3$)]$_2$, or —N($R_b$)($CH_2$)$_q$—N ($R_b$)$_2$;

W' is selected from O, S, NH, N-lower alkyl ($C_1$–$C_3$), —NCO-lower alkyl ($C_1$–$C_3$), or $NSO_2$-lower alkyl ($C_1$–$C_3$); or (b) a moiety of the formula:

wherein:

X is a bond, O, S, NH,

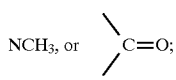

$R_{10}$ is selected from the group of lower alkyl ($C_3$–$C_8$), lower alkenyl ($C_3$–$C_8$), —($CH_2$)$_p$-cycloalkyl ($C_3$–$C_6$),

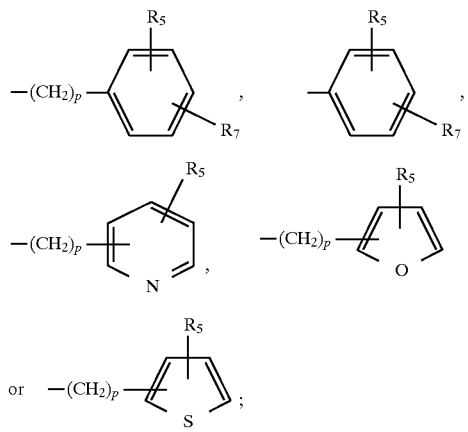

p is an integer from 0 to 3;

$R_5$ and $R_7$ are independently selected from H, lower alkyl ($C_1$–$C_3$), lower alkoxy ($C_1$–$C_3$), or halogen; or (c) a moiety of the formula:

wherein

J is $R_a$, lower alkyl ($C_1$–$C_8$) branched or unbranched, lower alkenyl ($C_2$–$C_8$) branched or unbranched, —O-lower allyl ($C_1$–$C_8$) branched or unbranched, —O-lower alkenyl ($C_2$–$C_8$) branched or unbranched, tetrahydrofuran, tetrahydrothiophene, the moieties:

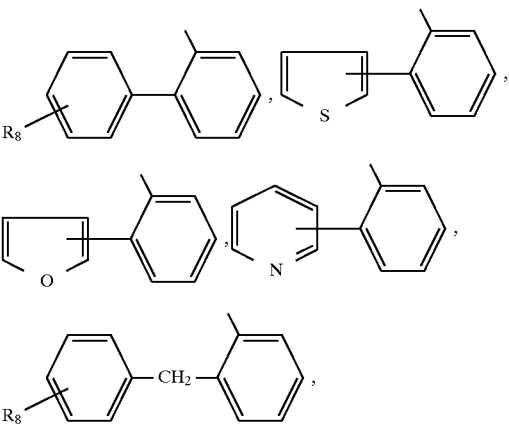

or —$CH_2$—K' wherein K is halogen, —OH, tetrahydrofuran, tetrahydrothiophene or the heterocyclic ring moiety:

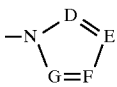

wherein D, E, F and G are selected from carbon or nitrogen and wherein the carbon atoms may be optionally substituted with halogen, ($C_1$–$C_3$)lower alkyl, hydroxy, —CO-lower alkyl ($C_1$–$C_3$), CHO, ($C_1$–$C_3$)lower alkoxy, or —$CO_2$-lower alkyl ($C_1$–$C_3$);

$R_8$, $R_a$ and $R_b$ are as hereinbefore defined; or (d) a moiety selected from those of the formulae:

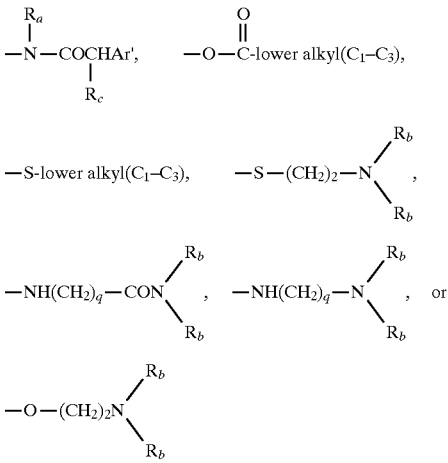

$R_c$ is selected from halogen, ($C_1$–$C_3$) lower alkyl, —O-lower alkyl ($C_1$–$C_3$) or OH;

$R_b$, q, Ar', $R_4$, $R_8$, $R_9$, and W' are as defined above;

$R_{25}$ is selected from the moieties:

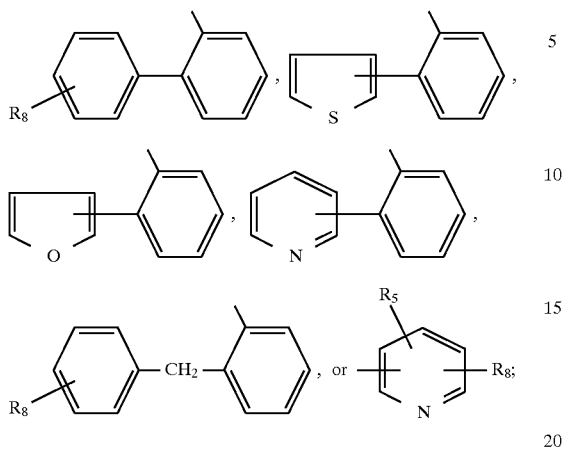

or a pharmaceutically acceptable salt thereof.

27. The compound according to claim 26, N-[5-[(6,11-dihydro-5H-pyrido[2,3-b][1,4]benzodiazepin-5-yl)carbonyl]-2-pyridinyl]-5-fluoro-2-methylbenzamide.

28. The compound according to claim 26, N-[4-[(6,11-dihydro-5H-pyrido[2,3-b][1,4]benzodiazepin-5-yl)carbonyl]-3-chlorophenyl][1,1'-biphenyl]-2-carboxamide.

29. The compound according to claim 26, N-[4-[(6,11-dihydro-5H-pyrido[2,3-b][1,4]benzodiazepin-5-yl)carbonyl]phenyl][1,1'-biphenyl]-2-carboxamide.

30. The compound according to claim 26, N-[4-[(6,11-dihydro-5H-pyrido[2,3-b][1,4]benzadiazepin-5-yl)carbonyl]-3-methylphenyl][1,1'-biphenyl]-2-carboxamide.

31. The compound according to claim 26, N-[4-(6,11-dihydropyrido [2,3-b][1,5]benzodiazepin-6(5H)-ylcarbonyl)-phenyl][1,1'-biphenyl]-2-carboxamide.

32. The compound according to claim 26, N-[4-(6,11-dihydropyrido [2,3-b][1,5]benzodiazepin-6(5H)-ylcarbonyl)-3-chlorophenyl][1,1'-biphenyl]-2-carboxamide.

33. The compound according to claim 26, N-[4-(6,11-dihydro-pyrido[2,3-b][1,5]benzodiazepin-6(5H-ylcarbonyl)-phenyl][1,1'-biphenyl]-2-carboxamide, hydrochloride.

34. A compound selected from those of Formula I:

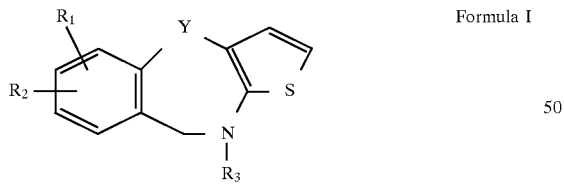

Formula I wherein:

Y is selected from NH or N-lower alkyl ($C_1$–$C_3$);

$R_1$ is hydrogen, halogen (—Cl, —Br, —F, —I), —OH, —S-lower alkyl($C_1$–$C_3$), —SH, —SO-lower alkyl($C_1$–$C_3$), —SO$_2$-lower alkyl($C_1$–$C_3$), —CO-lower alkyl($C_1$–$C_3$), —CF$_3$, lower alkyl($C_1$–$C_3$), —O-lower alkyl($C_1$–$C_3$), —NO$_2$, —NH$_2$, —NHCO-lower alkyl ($C_1$–$C_3$), —N-[lower alkyl($C_1$–$C_3$)]$_2$, —SO$_2$NH$_2$, —SO$_2$NH-lower alkyl ($C_1$–$C_3$), or —SO$_2$N[lower alkyl($C_1$–$C_3$)]$_2$;

$R_2$ is hydrogen, —Cl, —Br, —F, —I, —OH, -lower alkyl($C_1$–$C_3$), —O-lower alkyl($C_1$–$C_3$), or $R_1$ and $R_2$ taken together are methylenedioxy or ethylenedioxy;

$R_3$ is the moiety:

Ar is selected from the moieties:

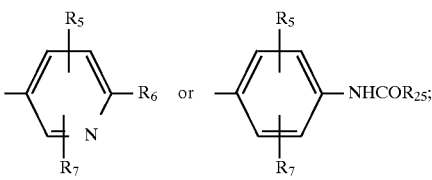

$R_5$ and $R_7$ are independently selected from H, lower alkyl ($C_1$–$C_3$), lower alkoxy ($C_1$–$C_3$), or halogen;

$R_{25}$ is selected from the moieties:

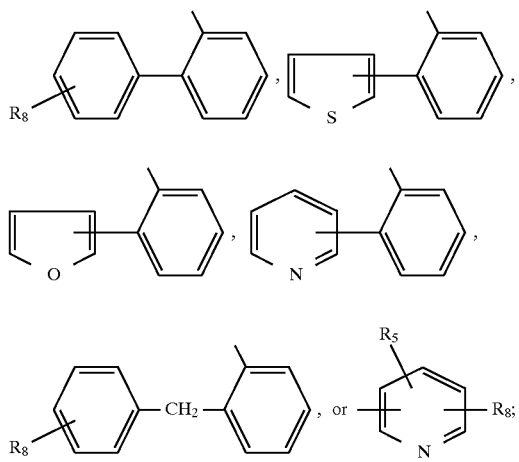

$R_6$ is selected from:

(a) the moieties of the formulae:

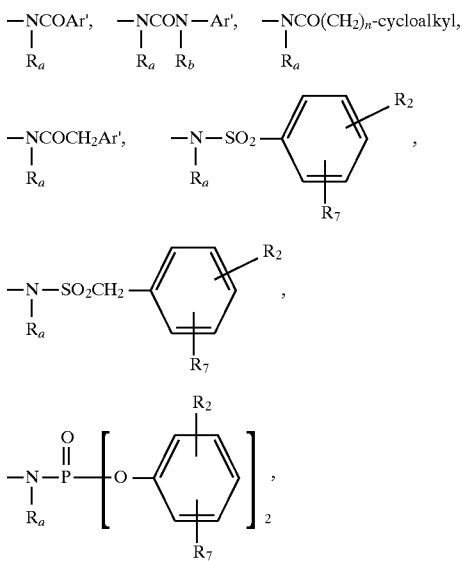

-continued

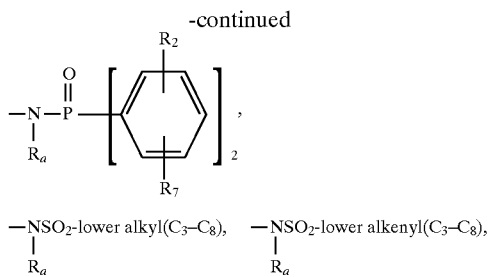

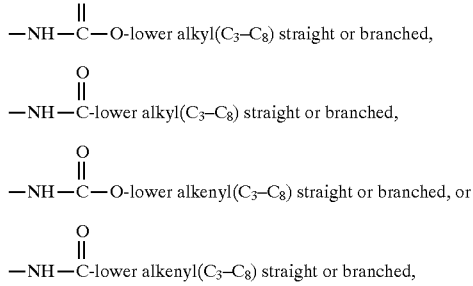

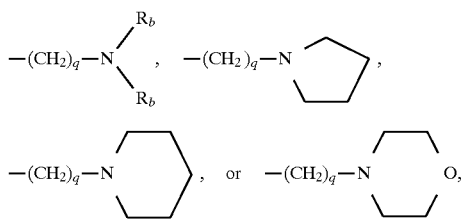

wherein
n is 0–2;
cycloalkyl is defined as $C_3$–$C_6$ cycloalkyl, cyclohexenyl or cyclopentenyl;
$R_a$ is hydrogen, $CH_3$, $C_2H_5$, moieties of the formulae:

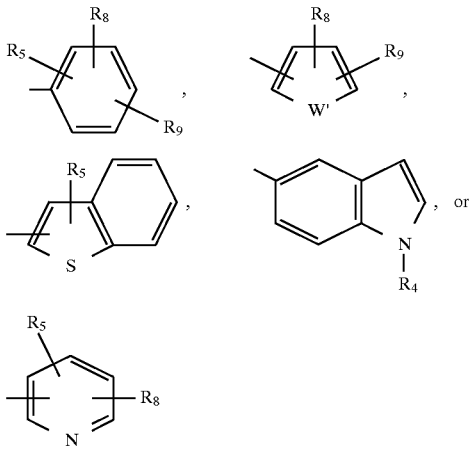

—$(CH_2)_2$—O-lower alkyl ($C_1$–$C_3$) or —$CH_2CH_2OH$;
q is one, two or three;
$R_b$ is hydrogen, —$CH_3$ or —$C_2H_5$;
Ar' is selected from the group:

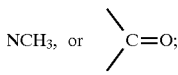

$R_4$ is selected from H, lower alkyl ($C_1$–$C_3$), or —CO-lower alkyl ($C_1$–$C_3$);
$R_8$ and $R_9$ are independently hydrogen, lower alkyl ($C_1$–$C_3$), —O-lower alkyl ($C_1$–$C_3$), S-lower alkyl ($C_1$–$C_3$), —$CF_3$, —CN, —OH, —$SCF_3$, —$OCF_3$, halogen, $NO_2$, amino, —NH-lower alkyl ($C_1$–$C_3$), —N-[lower alkyl ($C_1$–$C_3$)]$_2$, or —$N(R_b)(CH_2)_q$—N $(N_b)_2$;

W' is selected from O, S, NH, N-lower alkyl ($C_1$–$C_3$), —NCO-lower alkyl ($C_1$–$C_3$), or $NSO_2$-lower alkyl ($C_1$–$C_3$); or (b) a moiety of the formula:

—X—$R_{10}$ wherein:
X is a bond, O, S, NH,

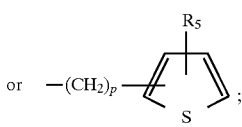

$R_{10}$ is selected from the group of lower alkyl ($C_3$–$C_8$), lower alkenyl ($C_3$–$C_8$), —$(CH_2)_p$-cycloalkyl ($C_3$–$C_6$),

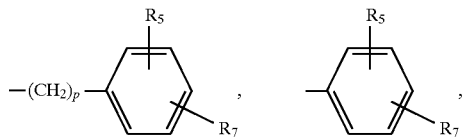

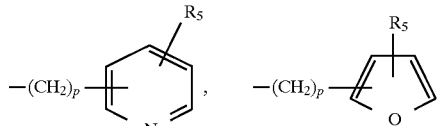

p is an integer from 0 to 3;
$R_5$ and $R_7$ are independently selected from H, lower alkyl ($C_1$–$C_3$), lower alkoxy ($C_1$–$C_3$), or halogen;
(c) a moiety of the formula:

—N—COJ wherein
J is $R_a$, lower alkyl ($C_1$–$C_8$) branched or unbranched, lower alkenyl ($C_2$–$C_8$) branched or unbranched, —O-lower alkyl ($C_1$–$C_8$) branched or unbranched, —O-lower alkenyl ($C_2$–$C_8$) branched or unbranched, tetrahydrofuran, tetrahydrothiophene, the moieties:

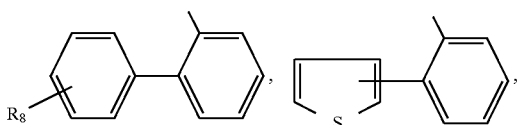

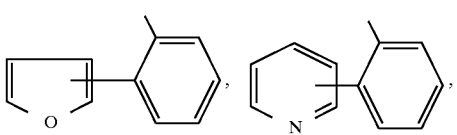

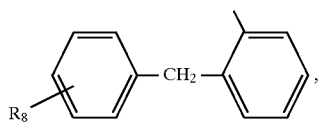

or —CH₂—K' wherein K is halogen, —OH, tetrahydrofuran, tetrahydrothiophene or the heterocyclic ring moiety:

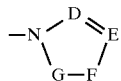

wherein D, E, F and G are selected from carbon or nitrogen and wherein the carbon atoms may be optionally substituted with halogen, $(C_1-C_3)$ lower alkyl, hydroxy, —CO-lower alkyl $(C_1-C_3)$, CHO, $(C_1-C_3)$ lower alkoxy, or —CO₂-lower alkyl $(C_1-C_3)$, and $R_a$ and $R_b$ are as hereinbefore defined; or (d) a moiety selected from those of the formulae:

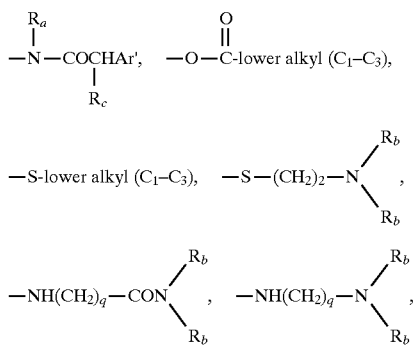

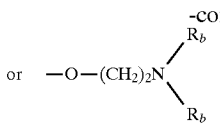

$R_c$ is selected from halogen, $(C_1-C_3)$ lower alkyl, —O-lower alkyl $(C_1-C_3)$ or OH;

$R_b$ is as hereinbefore defined;

q, Ar', $R_4$, $R_8$, $R_9$ and W' are as described above;

or a pharmaceutically acceptable salt thereof.

35. The compound according to claim 34, N-[5-(4H-thieno[3,4-b][1,5]benzodiazepin-9(10H)-yl)-2-pyridinyl]-5-fluoro-2-methylbenzamide.

36. The compound according to claim 34, N-[4-(4H-thieno[3,4-b][1,5]benzodiazepin-9(10H)-yl)-phenyl][1,1'-biphenyl]-2-carboxamide.

37. The compound according to claim 34, N-[4-(4H-thieno[3,4-b][1,5]benzodiazepin-9(10H)-yl)-3-chlorophenyl][1,1'-biphenyl]-2-carboxamide.

38. The compound according to claim 34, N-[5-(4H-thieno[3,4-b][1,5]benzodiazepin-9(10H)-yl)-2-pyridinyl][1,1'-biphenyl]-2-carboxamide.

39. A pharmaceutical composition useful for treating diseases characterized by excess renal reabsorption of water as well as congestive heart failure, liver cirrhosis, nephrotic syndrome, central nervous system injuries, lung disease and hyponatremia in a mammal comprising a suitable pharmaceutical carrier and an effective amount of a compound of claim 34.

40. A method of treating diseases characterized by excess renal reabsorption of water as well as congestive heart failure, liver cirrhosis, nephrotic syndrome, central nervous system injuries, lung disease and hyponatremia in a mammal comprising administering a compound of claim 34 to said mammal in an amount effective to alleviate the disease.

* * * * *